United States Patent [19]

Suzuki et al.

[11] Patent Number: 5,126,362
[45] Date of Patent: Jun. 30, 1992

[54] OXIME DERIVATIVE AND FUNGICIDE FOR AGRICULTURAL AND HORTICULTURAL USE

[75] Inventors: Hideo Suzuki; Takeshi Mita; Toshiaki Takeyama, all of Funabashi; Masami Hanaue, Saitama; Masao Nishikubo, Saitama; Kazuhiro Yamagishi, Saitama, all of Japan

[73] Assignee: Nissan Chemical Industries, Ltd., Tokyo, Japan

[21] Appl. No.: 412,220

[22] Filed: Sep. 25, 1989

[30] Foreign Application Priority Data

Jun. 19, 1988 [JP] Japan .................................. 1-156079
Sep. 24, 1988 [JP] Japan ................................. 63-239538
Jun. 14, 1989 [JP] Japan .................................. 1-151055

[51] Int. Cl.$^5$ ................. C07D 409/12; C07D 407/12; C07D 231/12; A01N 43/56
[52] U.S. Cl. ..................................... 514/406; 548/374; 548/378
[58] Field of Search ................. 548/374, 378; 514/406

[56] References Cited

U.S. PATENT DOCUMENTS 5,039,694 8/1991 Suzuki et al. .................... 548/374

Primary Examiner—Joseph Paul Brust
Assistant Examiner—M. S. H. Gabilan
Attorney, Agent, or Firm—Oliff & Berridge

[57] ABSTRACT

An oxime derivative represented by the general formula [1]:

$$A-CONHCH-C=NO-Y \quad [1]$$
$$\phantom{A-CONHCH-}| \phantom{-}|$$
$$\phantom{A-CONHCH-}B \phantom{-}W$$

wherein A, B, Y and W represent each a specified group, and an optically active isomer thereof and a fungicide for agricultural and horticultural use for containing said derivative or an optically active isomer thereof as an active ingredient are disclosed.

4 Claims, No Drawings

OXIME DERIVATIVE AND FUNGICIDE FOR AGRICULTURAL AND HORTICULTURAL USE

BACKGROUND OF THE INVENTION

This invention relates to a novel oxime derivative and a fungicide for agricultural and horticultural use containing said derivative as an active ingredient.

Disease damage caused by plant pathogenic fungi belonging to the class phycomycetes including downy mildew and phytophthora rot is one of serious problems in agricultural production. The specific physiological and morphological properties of these fungi make it difficult to prevent the disease damage caused thereby. Thus it has been urgently required to develop an effective fungicide. Downy mildew and phytophthora rot seriously damage various crops.

Known fungicides which are widely used at present against the disease damage caused by plant pathogenic fungi belonging to the class phycomycetes include captan (common name), captafol (common name), dithiocarbamate fungicides such as zineb and chlorotalonil (common name). However these fungicides mostly exert not therapeutic but preventive effects. Thus they have a serious disadvantage that no satisfactory effect can be achieved when they are used after the occurrence of the disease damage. On the other hand, fungicides comprising acylalanine compounds such as metharaxyl (common name), which have been recently developed and put into practical use, exert both of preventive and therapeutic effects. However strains resistant thereto have already appeared, which considerably lowers the effects of these fungicides.

Prior arts comprising a compound whose structure is somewhat similar to that of the compound of the present invention include European Patent Laid-Open No. 0268892 which has been filed by the present inventors.

The present invention aims at providing a fungicide which simultaneously exerts both of preventive and therapeutic effects on disease caused by plant pathogenic fungi belonging to the class Phycomycetes without giving any chemical damage to useful crops. There has been urgently required to develop such an excellent fungicide as described above.

SUMMARY OF THE INVENTION

It is an object of the present invention to provide a novel oxime derivative.

It is another object of the present invention to provide a fungicide containing said oxime derivative as an active ingredient.

Further, it is another object of the present invention to provide a fungicide which exerts both of preventive and therapeutic effects on disease caused by plant pathogenic fungi belonging to the class Pycomycetes without giving any chemical damage to useful crops.

It is still another object of the present invention to provide an intermediate for the preparation of the abovementioned fungicide.

DETAILED DESCRIPTION OF THE INVENTION

The present inventors have conducted extensive studies in order to overcome the above problems. As a result, they have found that compounds represented by the following general formula [1] simultaneously exert both of preventative and therapeutic effects on phytophthora rot and downy mildew of various plants while causing little chemical damage to crops, thus completing the present invention.

The compound of the present invention, which is an active ingredient of a fungicide for agricultural and horticultural use, is a novel one which has never been found in any report so far.

Compared with compounds described in the European Patent Laid-Open No. 0268892, which has been filed by the present inventors, the compound of the present invention is highly advantageous in that the chemical damage to crops is further lowered.

Accordingly, the present invention relates to an oxime derivative represented by the following general formula [1]:

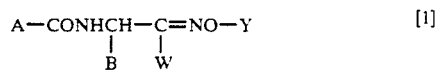

wherein A represents an optionally substituted aryl group or an optionally substituted heterocyclic group, B represents an optionally substituted phenyl group, an optionally substituted furyl group, an optionally substituted thienyl group, an optionally substituted pyrazolyl group, an alkenyl group having 2 to 10 carbon atoms, a halogenated alkenyl group having 2 to 10 carbon atoms, an alkoxy group having 1 to 10 carbon atoms, an alkenyloxy group having 2 to 10 carbon atoms, an alkynyloxy group having 2 to 10 carbon atoms or an alkylthio group having 1 to 10 carbon atoms, Y represents a hydrogen atom, an alkyl group, an alkenyl group, an alkynyl group, an optionally substituted phenyl group, an alkylcarbonyl group, an optionally substituted phenylcarbonyl group, an optionally substituted heterocyclic carbonyl group, an alkylaminocarbonyl group, an optionally substituted phenylaminocarbonyl group, an optionally substituted heterocyclic aminocarbonyl group, an alkylaminothiocarbonyl group or an alkoxycarbonyl group, W represents a hydrogen atom, a halogen atom, an amino group, an alkylamino group, an optionally substituted phenylamino group, an optionally substituted heterocyclic amino group, an alkylsulfonyl group, an optionally substituted phenylsulfonyl group or a dialkylaminosulfonyl group, an optically active isomer thereof and a fungicide for agricultural and horticultural use containing one or more of these compounds as active ingredients(s).

Particular examples of the group A in the above general formula [1] are as follows.

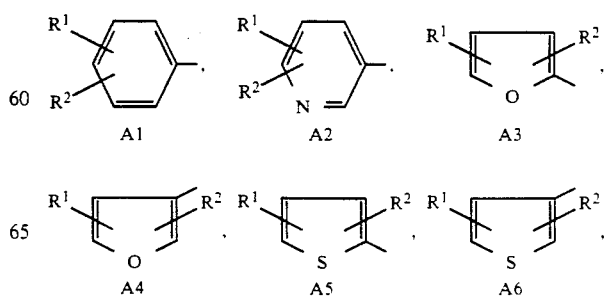

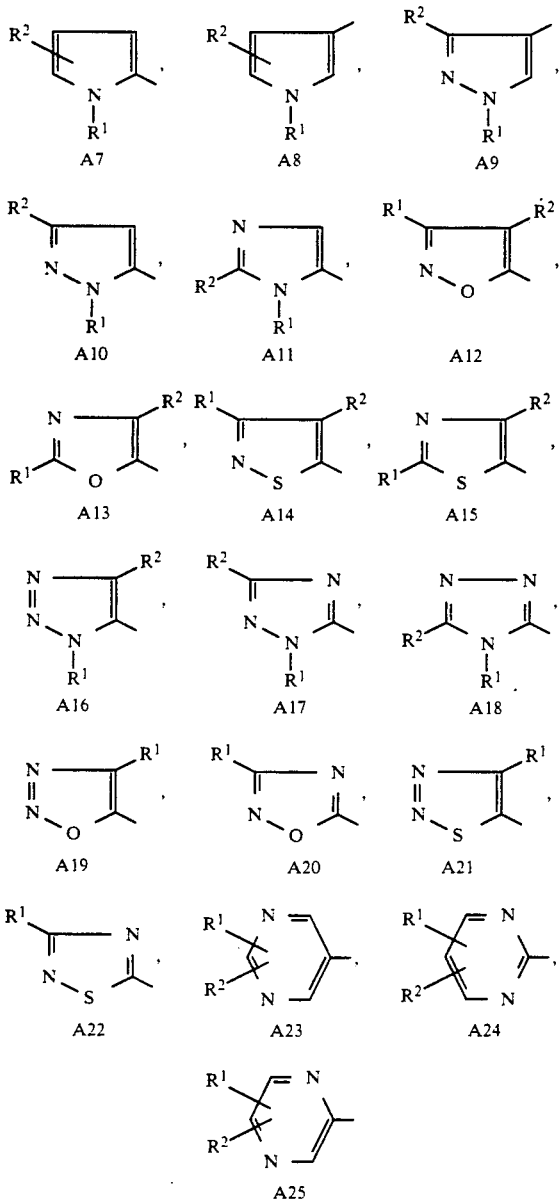

In the above definition of the group A, the substituents $R^1$ and $R^2$ independently represent each a hydrogen atom, a halogen atom, an alkyl group having 1 to 10 carbon atoms, an alkenyl group having 2 to 10 carbon atoms, an alkynyl group having 2 to 10 carbon atoms, an alkenyl group having 3 to 10 carbon atoms, a halogenated alkyl group having 1 to 10 carbon atoms, an alkoxy group having 1 to 10 carbon atoms, an alkylsulfoxide group having 1 to 6 carbon atoms, an alkylsulfone group having 1 to 6 carbon atoms, an alkylcarbonyl group having 2 to 6 carbon atoms, an alkoxyalkylcarbonyl group having 3 to 6 carbon atoms, an N,N-dialkylaminocarbonyl group having 3 to 6 carbon atoms, an alkoxycarbonyl group having 2 to 6 carbon atoms, an alkoxycarbonylalkyl group having 3 to 6 carbon atoms, a cyanoalkyl group having 2 to 6 carbon atoms, a hydroxyalkyl group having 1 to 6 carbon atoms, a hydroxyl group, an amino group, an alkylamino group having 1 to 6 carbon atoms, a phenyl group optionally substituted with a halogen atom or an alkyl group having 1 to 4 carbon atoms, an alkoxyalkyl group having 2 to 10 carbon atoms, an optionally substituted cycloalkyl group having 3 to 10 carbon atoms, an optionally substituted cycloalkylalkyl group having 4 to 10 carbon atoms, a cycloalkenyl group having 3 to 10 carbon atoms, an optionally substituted epoxy having 2 to 10 carbon atoms, an optionally substituted oxetyl having 3 to 10 carbon atoms, an optionally substituted tetrahydrofuryl having 4 to 10 carbon atoms, an optionally substituted tetrahydrothienyl having 4 to 10 carbon atoms, an optionally substituted epoxyalkyl group having 3 to 10 carbon atoms, an optionally substituted oxetylalkyl group having 4 to 10 carbon atoms, an optionally substituted tetrahydrofurylalkyl group having 5 to 10 carbon atoms or an optionally substituted 1,3-dioxolylalkyl group having 4 to 10 carbon atoms.

The compounds of the present invention represented by the general formula [I] may be present in the form of syn-anti isomers. The present invention involves these isomers.

Among the compounds of the present invention represented by the general formula [I], those satisfying the following requirements are particularly preferable from the viewpoints of, for example, effects. Namely, A represents an optionally substituted pyrazolyl group, an optionally substituted pyridyl group, an optionally substituted phenyl group, an optionally substituted thiazolyl group or an optionally substituted oxazolyl group; B represents an optionally substituted furyl group, an optionally substituted thienyl group, an optionally substituted pyrazolyl group, an alkenyl group having 2 to 10 carbon atoms or an alkoxy group having 1 to 10 carbon atoms; Y represents a hydrogen atom, an alkyl group, an alkenyl group, an optionally substituted phenylcarbonyl group, an alkylaminocarbonyl group, a phenylaminocarbonyl group, an alkylaminothiocarbonyl group or an alkoxycarbonyl group; and W represents a hydrogen atom, a halogen atom, an amino group or an alkyl amino group.

Particularly preferable compounds are those represented by the general formula [I] wherein A is an optionally substituted pyrazolyl group; B is an optionally substituted furyl group, an optionally substituted thienyl group or an alkenyl group having 2 to 10 carbon atoms; Y is a hydrogen atom; and W is a hydrogen atom, a halogen atom, an amino group or an alkylamino group.

Particular examples of these preferable compounds are those having the following numbers in Tables 1 to 4 which will be given hereinafter. Compound No.: 13, 25, 26, 27, 100, 101, 104, 156, 157, 158, 159, 173, 175, 176, 179, 180, 181, 182, 306, 311, 316, 317, 321, 343, 439, 448, 1007, 1013, 1023, 1024, 1028, 1033, 1034, 1035, 1037, 1038, 1039, 1040, 1042, 1043 and 1539. More particularly, the following compounds may be cited.

No. 316 (1)

α-(1-cyclobutyl-3-methylpyrazole-5-yl-carbonylamino)-(2-thienyl)acetoamidoxime

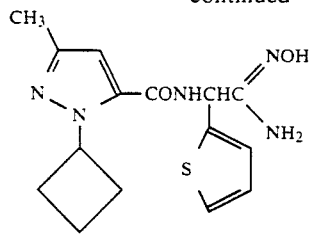

No. 311 (2)

α-(1-cyclobutyl-3-methylpyrazole-5-yl-carbonyl-amino)-(3-furyl)acetoamidoxime

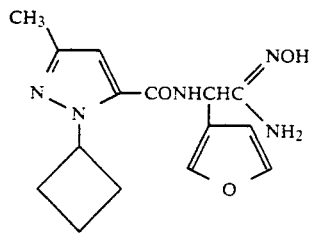

No. 158 (3)

α-(1,3-dimethylpyrazole-5-yl-carbonylamino)-(2-thienyl)actoamidoxime

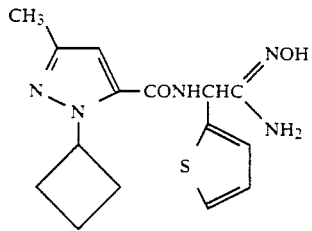

No. 175 (4)

α-(1-ethyl-3-methylpyrazole-5-yl-carbonyl-amino)-(2-thienyl)actoamidoxime

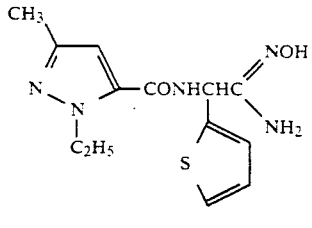

No. 1007 (5)

α-(1-cyclopropylmethyl-3-methylpyrazole-5-yl-carbonylamino)-(2-thienyl)actoamidoxime

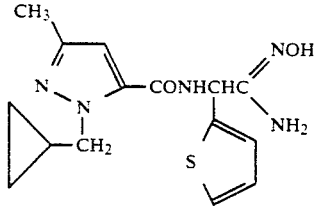

No. 306 (6)

α-(1-cyclobutyl-3-methylpyrazole-5-yl-carbonyl-amino)-(2-furyl)acetoamidoxime

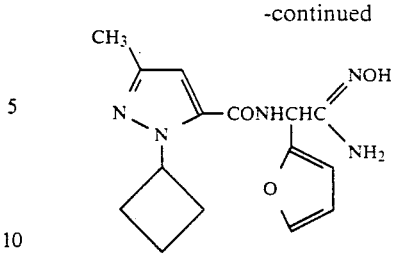

No. 173 (7)

α-(1-ethyl-3-methylpyrazole-5-yl-carbonylamino)-(2-furyl)actoamidoxime

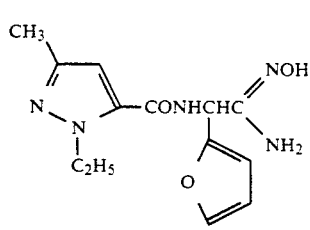

No. 321 (8)

α-(1-cyclobutyl-3-methylpyrazole-5-yl-carbonyl-amino)-(3-thienyl)actoamidoxime

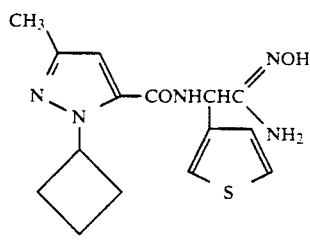

No. 181 (9)

α-(1-isopropyl-3-methylpyrazole-5-yl-carbonyl-amino)-(2-thienyl)actoamidoxime

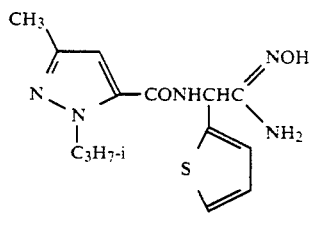

No. 182 (10)

α-(1-isopropyl-3-methylpyrazole-5-yl-carbonyl-amino)-(3-thienyl)actoamidoxime

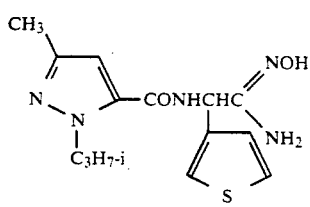

No. 315 (11)

α-(1-cyclopropyl-3-methylpyrazole-5-yl-carbonyl-amino)-(2-thienyl)acetoamidoxime

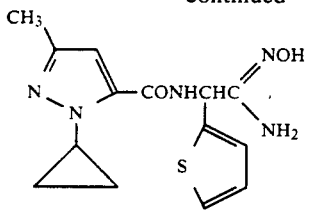

No. 320

α-(1-cyclopropyl-3-methylpyrazole-5-yl-carbonyl-amino)-(3-thienyl)actoamidoxime

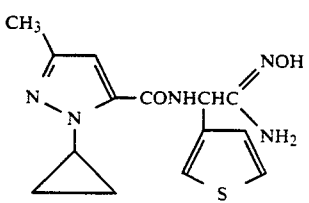

No. 305

α-(1-cyclopropyl-3-methylpyrazole-5-yl-carbonyl-amino)-(2-furyl)actoamidoxime

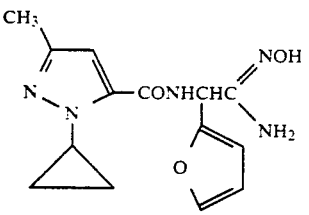

No. 310

α-(1-cyclopropyl-3-methylpyrazole-5-yl-carbonyl-amino)-(3-furyl)actoamidoxime

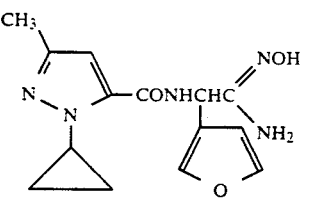

Now processes for the preparation of the compounds of the present invention will be described by referring to the reaction schemes.

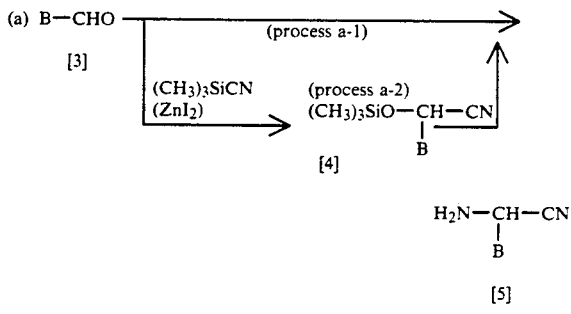

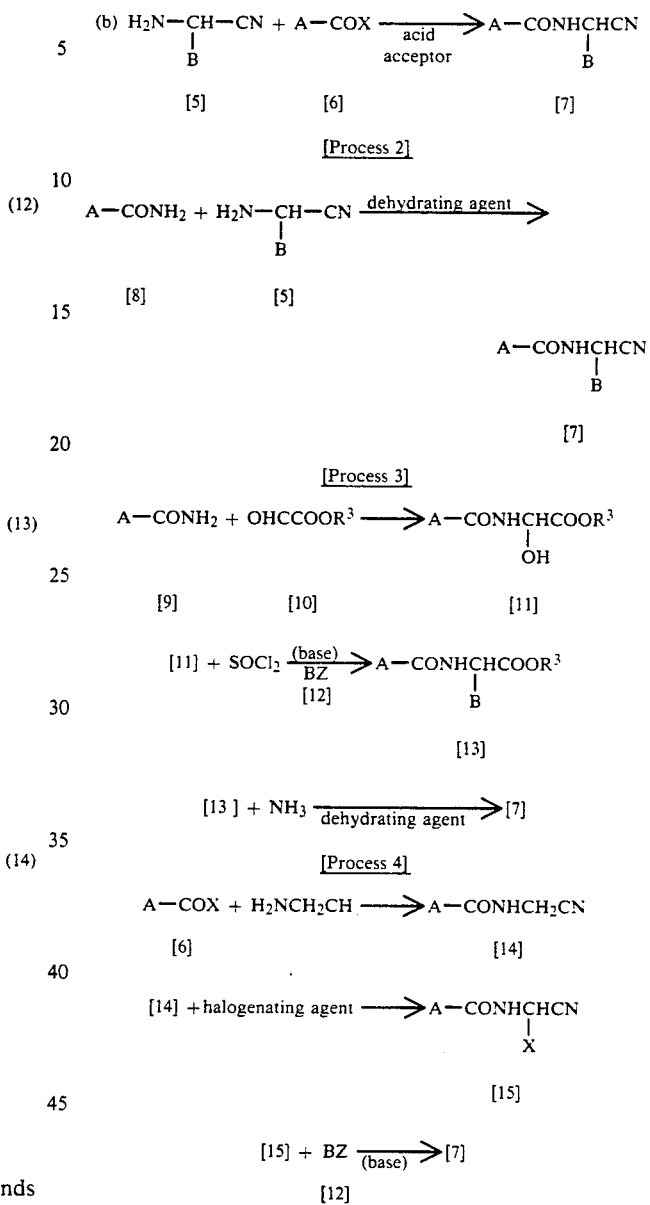

In the above reaction scheme, A and B are as defined above, $R^3$ represents an alkyl group having 1 to 4 carbon atoms, Z represents a hydrogen atom or an alkali metal such as lithium, sodium or potassium, and X represents a halogen atom.

DESCRIPTION OF PROCESS 1

In the first step, an aminoacetonitrile derivative [5] may be synthesized by two methods.

In the process a-1, the aimed compound is obtained through Strecker's reaction. Namely, an aldehyde [3], which is the starting material, is reacted with aqueous ammonia and/or ammonium chloride and an alkali cyanide such as sodium or potassium cyanide in a binary solvent system comprising an ether such as ethyl ether or tetrahydrofuran or an aromatic hydrocarbon such as benzene or toluene and water. The reaction may be preferably carried out at 0° to 100 °C.

In the process a-2, the starting aldehyde [3] is reacted with trialkylsilylnitrile such as trimethylsilylnitrile in the presence of, if required, a catalytic amount of a Lewis acid such as zinc iodide to thereby give an intermediate [4]. Next, the compound [4] is reacted with ammonia dissolved in a solvent such as methanol or ethanol, thus the aimed aminoacetonitrile derivative [5] is obtained.

The obtained aminoacetonitrile derivative [5] may be purified and isolated by, for example, forming a salt together with a hydrogen halide such as hydrogen chloride in an ether solvent such as diethyl ether.

In the second step, the aminoacetonitrile derivative [5] obtained in the first step is reacted with an acid halide represented by the general formula [6] in the presence of an acid acceptor.

Examples of the acid acceptor include organic bases such as triethylamine, dimethylaniline and pyridine and inorganic bases such as ammonia, potassium carbonate, sodium carbonate, ammonium hydrogencarbonate, sodium hydroxide and ammonium carbonate.

This reaction may be preferably conducted in the presence of a solvent. Examples of the solvent include ethers such as diethyl ether, tetrahydrofuran and diisopropyl ether, esters such as methyl acetate and ethyl acetate, halogenated hydrocarbons such as methylene chloride, chloroform and 1,2-dichloroethane, and acetonitrile. It is desirable to conduct this reaction, which is an exothermic one, under cooling, i.e., at a temperature of $-30°$ to $50°$ C., still preferably $-20°$ to $30°$ C. Thus the aimed amide-substituted acetonitrile derivative can be obtained.

DESCRIPTION OF PROCESS 2

In this process, a carboxylic acid derivative [8], which is a starting material, is dehydrated and condensed with the aminoacetonitrile derivative [5] obtained in Process 1 in the presence of a dehydrating agent to thereby give an amide-substituted acetonitrile derivative.

Preferable examples of the dehydrating agent include carbodiimides such as dicyclohexylcarbodiimide (DCC) and 1-ethyl-3-(3-dimethylaminopropyl)carbodiimide and inorganic ones such as silicon tetrachloride.

DESCRIPTION OF PROCESS 3

It is preferable that an amide derivative [9] is reacted with a glyoxylate in an ester solvent such as ethyl acetate or isobutyl acetate or acetone under heating to $50°$ to $100°$ C.

The resulting hydroxycompound [11] is reacted with an excessive amount of thionyl chloride below or around room temperature to thereby give a chlorinated compound. After the completion of the reaction, the excessive thionyl chloride is distilled off and the residue is reacted with a compound represented by the general formula BZ [12] in a solvent in the presence of, if required, a base. Thus an ester [13] is obtained.

Examples of the solvent to be used above include esters such as ethyl acetate and isobutyl acetate, ethers and acetonitrile. Examples of the base include organic bases such as triethylamine and pyridine and inorganic ones such as sodium carbonate and ammonium carbonate.

Next, the ester [13] is reacted with ammonia to thereby give an amide. This reaction may be preferably conducted in a solvent such as an alcohol, e.g., methanol or ethanol or an ether, e.g., diethyl ether or tetrahydrofuran at $-50°$ C. to room temperature. The amide may be further reacted in an organic amine such as pyridine by using a dehydrating agent such as absolute trifluoroacetic acid, in an amide solvent such as N,N-dimethylformamide (DMF) by using a dehydrating agent such as phosphorus oxychloride or by using a dehydrating agent such as polyphosphoric acid (PPA), a polyphosphoric acid alkyl ester (PPE) or a polyphosphoric acid alkylsilyl ester (PPSE) to thereby give an amide derivative 7.

DESCRIPTION OF PROCESS 4

An acylaminoacetonitrile derivative [14] may be readily obtained by reacting aminoacetonitrile with an acid chloride [6] under condensation conditions commonly used in the art. It is generally preferable to use a base in this reaction. Examples of the base include inorganic bases such as sodium carbonate and ammonium carbonate and organic ones such as triethylamine and pyridine.

The acylaminoacetonitrile derivative [14] may be converted into a halide [15] by using a halogenating agent. Preferable examples of the halogenating agent include chlorine, bromine, N-chlorosuccinimide and N-bromosuccinimide. Since this halogenated intermediate is unstable to heat, it is neither isolated nor purified but subjected to the subsequent step as such. After the completion of the halogenation, namely, the halogenated intermediate [15] is reacted with BZ [12] in a solvent in the presence of, if required, a base to thereby give an amide derivative [7].

This reaction may be conducted under the same conditions as those described in Process 3.

Reaction scheme II
(synthesis of oxime derivative)

[Process 5]

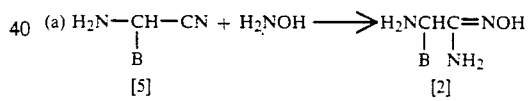

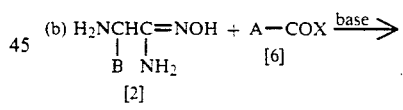

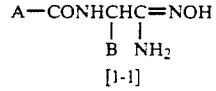

[Process 6]

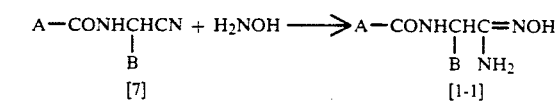

[Process 7]

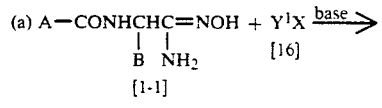

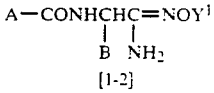

-continued
Reaction scheme II
(synthesis of oxime derivative)

(b) A—CONHCHC=NOH + Y$^1$COX $\xrightarrow{\text{base}}$
          |     |                    [17]
          B    NH$_2$
         [1-1]

$\quad\quad$ A—CONHCHC=NOCOY$^1$
                |     |
                B    NH$_2$
               [1-3]

[Process 8]

(a) A—CONHCHC=NOH + Y$^1$NCO $\longrightarrow$
          |     |                    [18]
          B    NH$_2$
         [1-1]

$\quad\quad$ A—CONHCHC=NOCONHY$^1$
                |     |
                B    NH$_2$
               [1-4]

(b) A—CONHCHC=NOH + Y$^1$NCS $\longrightarrow$
          |     |                    [19]
          B    NH$_2$
         [1-1]

$\quad\quad$ A—CONHCHC=NOCSNHY$^1$
                |     |
                B    NH$_2$
               [1-5]

[Process 9]

(a) A—CONHCHC=NOH + NaNO$_2$ + HX $\longrightarrow$
          |     |                    [20]
          B    NH$_2$
         [1-1]

$\quad\quad$ A—CONHCHC=NOH
                |     |
                B     X
               [1-6]

(b) A—CONHCHC=NOH + NaNO$_2$ + HX $\xrightarrow{\text{H}_3\text{PO}_2}$
          |     |                    [20]
          B    NH$_2$
         [1-1]

$\quad\quad$ A—CONHCHC=NOH
                |     |
                B     H
               [1-7]

[Process 10]

(a) A—CONHCHC=NOH + W$^1$—NH $\xrightarrow{\text{[base]}}$
          |     |              |
          B     X             W$^2$
         [1-6]              [21]

$\quad\quad$ A—CONHCHC=NOH
                |     |
                B    NW$^1$W$^2$
               [1-8]

(b) A—CONHCHC=NOH + W$^1$SO$_2$Z $\longrightarrow$
          |     |                [22]
          B     X
         [1-6]

-continued
Reaction scheme II
(synthesis of oxime derivative)

$\quad\quad$ A—CONHCHC=NOH
                |     |
                B    SO$_2$W$^1$
               [1-9]

In the above reaction scheme, A, B, W, X, Y and Z are as defined above, Y$^1$ represents an alkyl, an alkenyl, an alkynyl, an optionally substituted phenyl, an optionally substituted heterocyclic or an alkoxycarbonyl group, and W$^1$ and W$^2$ independently represent each an alkyl, an alkenyl, an alkynyl, an optionally substituted phenyl or an optionally substituted heterocyclic group.

DESCRIPTION OF PROCESS 5

(a) An aminoacetamidoxime derivative or an inorganic or organic acid salt thereof [2] can be readily obtained by reacting the aminoacetonitrile derivative [5] obtained in Process 1 with hydroxylamine or an inorganic or organic acid salt thereof in a solvent such as methanol or ethanol. It is preferable to conduct this reaction at 0 ° C. to room temperature. The reaction is completed within 2 to 10 hours.

(b) When the aminoacetamidoxime derivative obtained in the above step (a) is an inorganic or organic acid salt, it may be neutralized with a base such as triethylamine or sodium methoxide and then reacted with an acid chloride [6] in the presence of a base such as triethylamine or pyridine. thus the aimed acetamidoxime derivative [1—1] of the present invention can be obtained. Preferable examples of the solvent to be used in the above reaction include nitriles such as acetonitrile, ethers such as tetrahydrofuran and halogenated hydrocarbons such as chloroform.

The reaction may be preferably conducted at −20 ° C. to room temperature. The reaction is completed within 2 to 5 hours.

DESCRIPTION OF PROCESS 6

The aimed acetamidoxime derivative [1—1] of the present invention may be readily obtained by reacting the amide-substituted acetonitrile derivative [7] obtained by the above Processes 1 to 4 with hydroxylamine.

In the above reaction, a solvent such as methanol or ethanol is used. The reaction may be preferably conducted at the reflux temperature of the employed solvent. The reaction is completed within 2 to 10 hours.

In addition to the above reactions, processes which are generally known for the preparation of amidoxime derivatives, e.g., the following reactions (1) to (3) may be employed in the present invention.

(1) E—C=NH or E—C=S + H$_2$NOH $\longrightarrow$ E—C=NOH
       |           |                              |
      OG         NH$_2$                          NH$_2$ (2) E—C=NOH or E—C=NOH + NH$_3$ $\longrightarrow$ E—C=NOH
       |            |                              |
       Cl          OG                            NH$_2$ (3) E—C=NOH + H$_2$S $\longrightarrow$ E—C=NOH
       |                                |
      NO                              NH$_2$ wherein E and G represent each an organic group.

In the above reaction (1), an iminoether or a thioamide is reacted with hydroxylamine. In the above reaction (2), a hydroxyimino acid chloride or a hydroxyimino ether is reacted with ammonia. In the reaction (3), a nitroso oxime is reduced with hydrogen sulfide.

DESCRIPTION OF PROCESS 7

(a) The aimed oxime derivative [1-2] may be obtained by reacting the oxime derivative [1—1] with a halide [16] in the presence of a base. Preferable examples of the base include alcholate such as sodium methoxide and potassium tertbutoxide and metal hydrides such as sodium hydride and potassium hydride.

(b) The aimed oxime derivative [1-3] may be obtained by reacting the oxime derivative [1—1] with a carboxylic acid halide [17] in the presence of a base. Preferable examples of the base include organic bases such as triethylamine and pyridine and inorganic ones such as sodium carbonate and ammonium carbonate.

DESCRIPTION OF PROCESS 8

(a) The aimed oxime derivative [1-4] may be obtained by reacting the oxime derivative [1—1] with an isocyanate.

(b) The aimed oxime derivative [1-5] may be obtained by reacting the oxime derivative [1—1] with a thioisocyanate [19].

DESCRIPTION OF PROCESS 9

(a) The aimed halide [1-6] may be obtained by reacting the amidoxime derivative [1—1] with sodium nitrite in a mineral acid amidoxime derivative [1—1] with sodium nitrite in a mineral acid to thereby form a diazonium salt and then neutralizing the obtained diazonium salt with a base such as sodium hydrogencarbonate to a pH value of 3 to 4.

As the mineral acid, hydrofluoric, hydrochloric, hydrobromic or hydriodic acid may be selected to thereby give the corresponding halide.

(b) The diazonium salt obtained in the above step (a) is treated with hypophosphorous acid to thereby give a hydride (oxime derivative) [1-7].

DESCRIPTION OF PROCESS 10

(a) The halide [1-6] obtained in the above Process 9-(a) is reacted with an amine (21), preferably in the presence of a base, to thereby give the aimed oxime derivative [1-8]).

(b) The halide [1-6) obtained in the above Process 9-(a) is reacted with a sulfinic acid metal salt [22] to thereby give the aimed oxime derivative [1-9].

To further illustrate the present invention, and not by way of limitation, the following Examples will be given.

EXAMPLE 1

Synthesis of compound No. 26

-continued
Synthesis of compound No. 26

To 10 g of 3-furylaldehyde and 11 g of trimethylsilyl cyanide was added a catalytic amount (50 mg) of zinc iodide under ice-cooling. The obtained mixture was stirred at room temperature for one hour. Next, 80 ml of ammonia-saturated methanol was added thereto and the mixture was stirred at 40 °C. for two hours. The reaction mixture was concentrated, extracted with ethyl acetate and then dried. After distilling off the solvent, 11.6 g of α-(3-furyl)aminoacetonitrile was obtained.

2.3 g of the α-(3-furyl)aminoacetonitrile and 4.1 g of triethylamine were dissolved in 100 ml of THF. Then 3.6 g of nicotinic acid chloride hydrochloride was added thereto under ice-cooling. The obtained mixture was stirred for one hour and then at room temperature for six hours. After filtering the solid matter thus formed, the solvent was distilled off. The obtained oily substance was purified by column chromatography to thereby give 2.7 g of α-(nicotinylamino)-(3-furyl) acetonitrile in the form of crystals.

m.p.: 80°-82° C.

Next, 1.4 g of hydroxylamine hydrochloride was neutralized in 30 ml of methanol with 1.2 g of sodium methoxide. Subsequently 4.6 g of the α-(nicotinylamino)-(3-furyl)-acetonitrile was added thereto followed by stirring.

After 15 minutes, the mixture was heated under reflux for two hours.

After the completion of the reaction, the solid matter thus formed was filtered and the solvent was distilled off. The resulting solid substance was purified by column chromatography and recrystallized from a solvent mixture of ethyl acetate with diethyl ether. Thus 4.2 g of the aimed N-(3-pyridylcarbonyl)α-(3-furyl)acetamidoxime was obtained in the form of crystals.

EXAMPLE 2

Synthesis of novel intermediate

-continued
Synthesis of novel intermediate

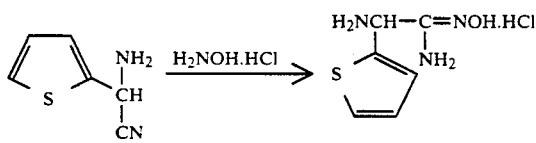

To 7.7 g of ammonium chloride and 4.9 g of potassium cyanide was added 80 ml of aqueous ammonia under ice-cooling. After stirring, 8.0 g of 2-thienylaldehyde dissolved in 80 ml of diethyl ether was added thereto and the obtained mixture was stirred at room temperature for 20 hours.

After the completion of the reaction, the diethyl ether phase was recovered while the aqueous phase was extracted with diethyl ether thrice. These diethyl ether phases were combined, dehydrated and dried. Then the solvent was distilled off to thereby give 7.8 g of α-(2-thienyl)aminoacetonitrile.

5.6 g of the -(2-thienyl)aminoacetonitrile thus obtained was dissolved in 30 ml of methanol and 2.8 g of hydroxylamine hydrochloride was added thereto in a water bath. After stirring for a while, the mixture began to crystallize while showing slight heat generation. The mixture was stirred at room temperature for several hours thereafter. After the completion of the reaction, the reaction mixture was concentrated and the solvent was distilled off. After recrystallizing from ethanol, 7.6 g of the aimed α-(2-thienyl)aminoacetamidoxime hydrochloride was obtained.

The following Table 1 shows physical data of novel amidoxime derivatives each obtained in a manner similar to the one described in Example 2.

TABLE 1

Compounds represented by the general formula:

$$\begin{array}{c} NH_2-CH-C=NOH \\ | \quad \quad | \\ B \quad \quad NH_2 \end{array} \cdot HCl.$$

| Ex. | B | m.p. (°C.) | $^1$H-NMR (reference material: TMS) (solvent: DMSO d-6 + CDCl$_3$) δ ppm |
|---|---|---|---|
| 2 | 2-thienyl (S) | 225–230 (decomp.) | 5.32(s, 1H), 6.95–7.17(m, 1H), 7.30–7.75(m, 2H), 8.17(brs, 2H), 8.85(brs, 2H) |
| 3 | 2-furyl (O) | 173–175 (decomp.) | 5.05(s, 1H), 5.90(brs, 2H), 6.40–6.60(m, 1H), 6.60–6.80(m, 1H), 7.65–7.80(m, 1H), 9.15(brs, 2H) |
| 4 | 3-thienyl (S) | 186–188 (decomp.) | 5.00(s, 1H), 5.88(brs, 2H), 7.27–7.90(m, 3H), 8.85(brs, 2H) |
| 5 | 3-furyl (O) | 185–187 (decomp.) | 4.90(s, 1H), 5.85(brs, 2H), 6.68–6.85(m, 1H), 7.60–7.75(m, 1H), 7.80–7.95(m, 1H), 8.50(brs, 2H) |

EXAMPLE 6

Synthesis of compound No. 1001

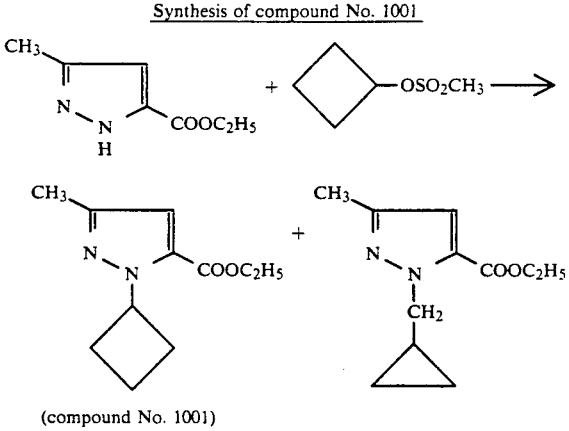

(compound No. 1001)

A mixture comprising 2.1 g of ethyl 3-methyl-1H-pyrazole-5-carboxylate, 2.1 g of cyclobutyl methanesulfonate and 2.6 g of tri-n-butylamine was allowed to react at 110° C. for three hours without using any solvent. Then the reaction mixture was allowed to cool and diethyl ether was added thereto. The obtained mixture was successively washed with 1 N hydrochloric acid, an aqueous solution of sodium hydrogencarbonate and a saturated aqueous solution of common salt and then dried over anhydrous sodium sulfate. The solvent was distilled off under reduced pressure and the obtained residue was purified by column chromatography (eluent: hexane : ethyl acetate = 14 : 1). Thus 0.5 g of the aimed ethyl 1-cyclobutyl-3-methyl-1H-pyrazole-5-carboxylate (compound No. 1001) (yield: 17.6 %) and 1.54 g of ethyl 1-cyclopropylmethyl-3-methyl-1H-pyrazole-5-carboxylate(yield: 54.3 %) were obtained.

EXAMPLE 7

Synthesis of Compound No. 1001

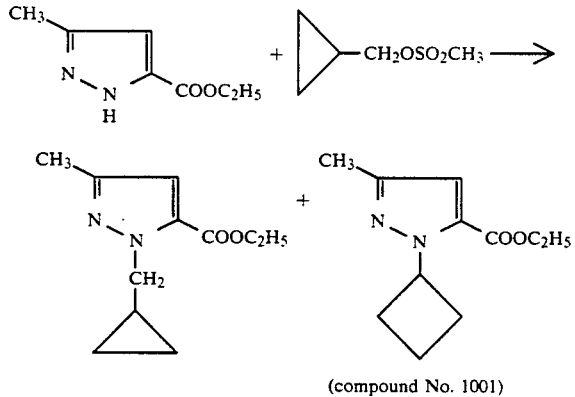

(compound No. 1001)

A mixture comprising 3.8 g of ethyl 3-methyl-1H-pyrazole-5-carboxylate, 3.8 g of cyclopropylmethyl methanesulfonate and 4.6 g of tri-n-butylamine was allowed to react at 110° C. for three hours without using any solvent. Then the reaction mixture was allowed to cool and diethyl ether was added thereto. The obtained mixture was successively washed with 1 N hydrochloric acid, an aqueous solution of sodium hydrogencarbonate and a saturated aqueous solution of common salt and then dried over anhydrous sodium sulfate. The solvent was distilled off under reduced pressure and the obtained residue was purified by column chromatography (eluent: hexane:ethyl acetate = 14 : 1). Thus 0.62 g of the aimed ethyl 1-cyclobutyl-3-methyl-1H-pyrazole-5-carboxylate (compound No. 1001) (yield: 12.1 %) and 2.45 g of ethyl 1-cyclopropylmethyl-3-methyl-1H-pyrazole-5-carboxylate (yield: 54.3 %) were obtained.

EXAMPLE 8

Synthesis of Compound No. 1002

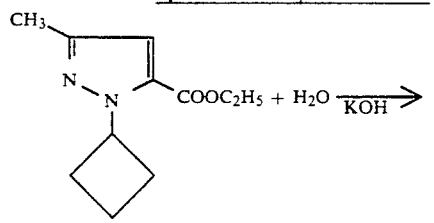

6.0 g of ethyl 1-cyclobutyl-3-methyl-1H-pyrazole-5-carboxylate was added to a mixture of 60 ml of a 1 N aqueous solution of potassium hydroxide with 80 ml of ethanol.

The mixture was allowed to react at room temperature for two hours. Then the ethanol was distilled off under reduced pressure and ethyl acetate was added to the residue. The pH value of the mixture was adjusted to 1.0 with 1 N hydrochloride and the organic phase was recovered, washed with a saturated aqueous solution of common salt and dried over anhydrous sodium sulfate. The solvent was distilled off under reduced pressure and thus 4.78 g of 1-cyclobutyl-3-methyl-1H-pyrazole-5-carboxylic acid was obtained in the form of white crystals (yield: 91.6 %).

EXAMPLE 9

Synthesis of compound No. 1003

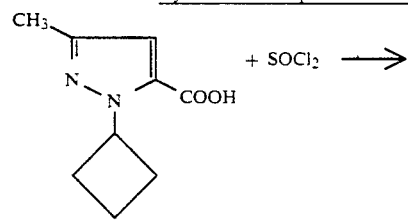

To 3.02 g of 1-cyclobutyl-3-methyl-1H-pyrazole-5-carboxylic acid were added 60 ml of benzene and 10 ml of thionyl chloride. The mixture was refluxed for two hours. Then the solvent was distilled off under reduced pressure and thus 3.2 g of 1-cyclobutyl-3-methyl-1H-pyrazole-5-carboxylic acid chloride was obtained (yield: 96.1%).

The following Table 2 shows the physical properties of the compounds No. 1001 to 1003.

TABLE 2

| Cpd. No. | Solvent | $^1$H-NMR data and m.p. $^1$H-NMR δppm (reference: TMS) m.p. (°C.) |
|---|---|---|
| 1001 | CDCl$_3$ | 1.32(t, 3H, J=7.2H$_z$), 1.53~2.18(m, 2H), 2.25(s, 3H), 2.18~3.04(m, 4H), oil 4.25(q, 2H, J=7.2H$_z$), 5.53 (quint, 1H, J=8.4H$_z$), 6.48(s, 1H) |
| 1002 | CDCl$_3$ | 1.47~2.16(m, 2H), 2.30(s, 3H), 2.16~3.07(m, 4H), 150~151 5.58 (quint, 1H, J=8.4H$_z$), 6.62(s, 1H), 12.37(s, 1H) |
| 1003 | CDCl$_3$ | 1.47~2.11(m, 2H), 2.26(s, 3H), 2.11~3.01(m, 4H), oil 5.21(quint, 1H, J=7.8H$_z$), 6.74(s, 1H) |

EXAMPLE 10

Synthesis of compound No. 316

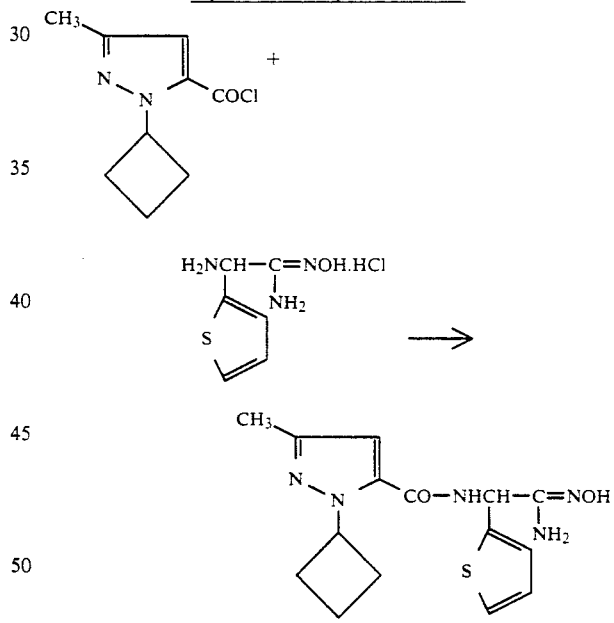

6.3 g (0.03 mol) of the α-(2-thienyl)aminoacetamidoxime hydrochloride obtained in Example 2 was neutralized in 80 ml of acetonitrile with 6.7 g (0.066 mol) of triethylamine. Then the solution was ice-cooled and 6.0 g (0.03 mol) of 1-cyclobutyl-3-methyl-1H-pyrazole-5-carboxylic acid chloride was added thereto dropwise. After stirring under ice-cooling for two hours, the mixture was further stirred at room temperature for three hours.

After the completion of the reaction, the reaction mixture was concentrated and the residue was dispersed in a solution comprising water and chloroform. After concentrating the chloroform phase, crude crystals were obtained. These crude crystals were recrystallized from a solvent mixture of ethanol with diethyl ether.

Thus 7.5 g of the aimed α-(1-cyclobutyl-3-methyl-pyrazole-5-yl-carboxylamino)-(2-thienyl)acetamidoxime was obtained in the form of crystals.

EXAMPLE 11

Synthesis of compound No. 158

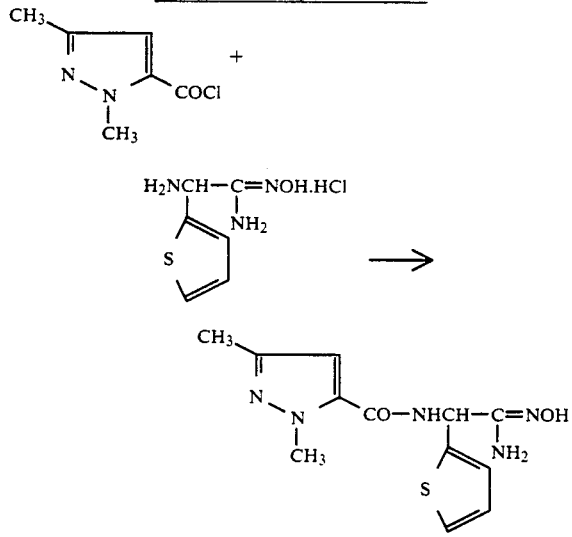

6.3 g (0.03 mol) of the α-(2-thienyl)aminoacetamidoxime hydrochloride obtained in Example 2 was neutralized in 80 ml of acetonitrile with 6.7 g (0.066 mol) of triethylamine. Then the solution was ice-cooled and 4.8 g (0.03 mol) of 1,3-dimethyl-(1H)-pyrazole-5-carboxylic acid chloride was added thereto dropwise. After stirring under ice-cooling for two hours, the mixture was further stirred at room temperature for three hours.

After the completion of the reaction, the reaction mixture was concentrated and the residue was dispersed in a solution comprising water and chloroform. After concentrating the chloroform phase, crude crystals were obtained. These crude crystals were recrystallized from a solvent mixture of ethanol with diethyl ether.

Thus 6.5 g of the aimed α-(1,3-dimethyl-pyrazole-5-yl-carboxylamino)-(2-thienyl)acetamidoxime was obtained in the form of crystals.

EXAMPLE 12

Synthesis of compound No. 1023

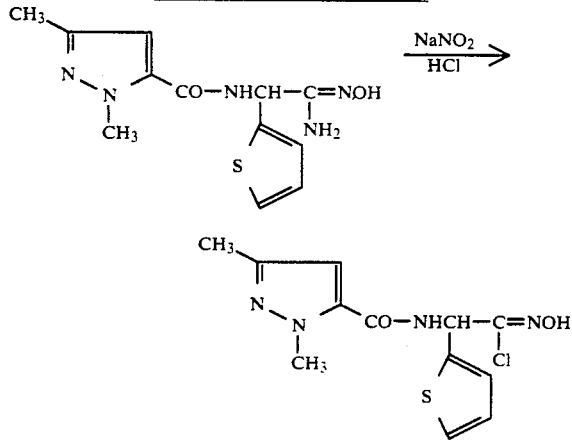

5.86 g (0.02 mol) of the α-(1,3-dimethyl-pyrazole-5-yl-carbonylamino)-(2-thienyl)acetamidoxime obtained in Example 11 was added to 70 ml of 4 N hydrochloric acid under ice-cooling and stirred. Then 1.66 g (0.024 mol) of sodium nitrite dissolved in 10 ml of water was added thereto dropwise.

The obtained mixture was stirred for additional three hours under ice-cooling.

Next, sodium hydrogencarbonate was slowly added thereto to thereby adjust the pH value of the mixture to 3 to 4. Thus the mixture crystallized.

The obtained crystals were filtered, washed with water and dried.

The crystals were purified by column chromatography to thereby give 3.44 g of the aimed α-(1,3-dimethyl-pyrazole-5-yl-carbonylamino)-(2-thienyl)-β-chloroacetoxime.

The following Tables 3 and 4 show the compounds of the present invention each synthesized in a manner similar to the one described above. In Tables 3 and 4, n represents normal, i represents iso, t represents tertiary and p represents para.

TABLE 3

In a compound represented by the general formula:

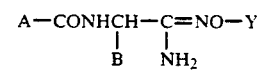

$$A-CONHCH-C=NO-Y$$
$$\quad\quad\quad | \quad\quad |$$
$$\quad\quad\quad B \quad\quad NH_2$$

| Compound No. | A | $R^1$ | $R^2$ | B | Y |
|---|---|---|---|---|---|
| 1 | A1 | H | H | B1 | H |
| 2 | A1 | H | H | B2 | H |
| 3 | A1 | H | H | B3 | H |
| 4 | A1 | H | H | B4 | H |
| 5 | A1 | H | H | B5 | H |
| 6 | A1 | H | H | B6 | H |
| 7 | A1 | 3-F | H | B3 | H |
| 8 | A1 | 4-Cl | H | B3 | H |
| 9 | A1 | 2-Cl | 4-Cl | B3 | H |
| 10 | A1 | 3-Cl | H | B3 | H |
| 11 | A1 | 3-Cl | 5-Cl | B1 | H |
| 12 | A1 | 3-Cl | 5-Cl | B2 | H |
| 13 | A1 | 3-Cl | 5-Cl | B3 | H |
| 14 | A1 | 3-Cl | 5-Cl | B4 | H |
| 15 | A1 | 3-Cl | 5-Cl | B5 | H |
| 16 | A1 | 3-Cl | 5-Cl | B6 | H |
| 17 | A1 | 3-Cl | 5-Cl | CH=C(CH$_3$)$_2$ | H |
| 18 | A1 | 3-Cl | 5-Cl | CH=CClCH$_3$ | H |
| 19 | A1 | 3-Cl | 5-Cl | OCH$_2$CH$_3$ | H |
| 20 | A1 | 3-Cl | 5-Cl | SCH$_2$CH$_3$ | H |
| 21 | A1 | 3-Cl | 5-Cl | OCH(CH$_3$)$_2$ | H |
| 22 | A1 | 3-Cl | 5-Cl | CH$_2$CH=CH$_2$ | H |
| 23 | A1 | 3-Cl | 5-Cl | CH$_2$C≡CH | H |
| 24 | A1 | 3-Cl | 5-Cl | O-Q1 | H |
| 25 | A2 | H | H | B1 | H |
| 26 | A2 | H | H | B2 | H |
| 27 | A2 | H | H | B3 | H |
| 28 | A2 | H | H | B4 | H |
| 29 | A2 | H | H | B5 | H |
| 30 | A2 | H | H | B6 | H |
| 31 | A2 | H | H | CH=C(CH$_3$)$_2$ | H |
| 32 | A2 | H | H | CH=CClCH$_3$ | H |
| 33 | A2 | H | H | OCH$_2$CH$_3$ | H |
| 34 | A2 | H | H | SCH$_2$CH$_3$ | H |
| 35 | A2 | H | H | OCH(CH$_3$)$_2$ | H |
| 36 | A2 | H | H | CH$_2$CH=CH$_2$ | H |
| 37 | A2 | H | H | CH$_2$C≡CH | H |
| 38 | A2 | H | H | O-Q1 | H |
| 39 | A2 | 5-Br | H | B3 | H |
| 40 | A3 | H | H | B3 | H |
| 41 | A3 | 4-CH$_3$ | H | B3 | H |
| 42 | A3 | 5-CH$_3$ | H | B3 | H |
| 43 | A4 | H | H | B1 | H |
| 44 | A4 | H | H | B2 | H |
| 45 | A4 | H | H | B3 | H |
| 46 | A4 | H | H | B4 | H |

TABLE 3-continued

In a compound represented by the general formula:

$$A-CONHCH-C=NO-Y$$
$$\phantom{A-CONHCH-}|\phantom{-C}|$$
$$\phantom{A-CONHCH-}B\phantom{-}NH_2$$

| Compound No. | A | R$^1$ | R$^2$ | B | Y |
|---|---|---|---|---|---|
| 47 | A4 | H | H | B5 | H |
| 48 | A4 | H | H | B6 | H |
| 49 | A4 | H | H | CH=C(CH$_3$)$_2$ | H |
| 50 | A4 | H | H | CH=CClCH$_3$ | H |
| 51 | A4 | H | H | OCH$_2$CH$_3$ | H |
| 52 | A4 | H | H | SCH$_2$CH$_3$ | H |
| 53 | A4 | H | H | O-Q1 | H |
| 54 | A4 | 2-CH$_3$ | 5-CH$_3$ | B3 | H |
| 55 | A5 | H | H | B3 | H |
| 56 | A5 | H | H | B5 | H |
| 57 | A6 | H | H | B3 | H |
| 58 | A6 | 4-CH$_3$ | H | B3 | H |
| 59 | A6 | CH$_3$ | H | B5 | H |
| 60 | A7 | CH$_3$ | H | B3 | H |
| 61 | A7 | CH$_3$ | H | B5 | H |
| 62 | A8 | CH$_3$ | H | B3 | H |
| 63 | A8 | CH$_3$ | H | B5 | H |
| 64 | A8 | CH$_3$ | H | B3 | H |
| 65 | A8 | CH$_3$ | H | B5 | H |
| 66 | A9 | CH$_3$ | H | B1 | H |
| 67 | A9 | CH$_3$ | H | B2 | H |
| 68 | A9 | CH$_3$ | H | B3 | H |
| 69 | A9 | CH$_3$ | H | B4 | H |
| 70 | A9 | CH$_3$ | H | B5 | H |
| 71 | A9 | CH$_3$ | H | B6 | H |
| 72 | A9 | CH$_3$ | H | CH=C(CH$_3$)$_2$ | H |
| 73 | A9 | CH$_3$ | H | CH=CClCH$_3$ | H |
| 74 | A9 | CH$_3$ | H | OCH$_2$CH$_3$ | H |
| 75 | A9 | CH$_3$ | H | SCH$_2$CH$_3$ | H |
| 76 | A9 | CH$_3$ | H | OCH(CH$_3$)$_2$ | H |
| 77 | A9 | CH$_3$ | H | CH$_2$CH=CH$_2$ | H |
| 78 | A9 | CH$_3$ | H | CH$_2$C≡CH | H |
| 79 | A9 | CH$_3$ | H | O-Q1 | H |
| 80 | A9 | C$_2$H$_5$ | H | B1 | H |
| 81 | A9 | C$_2$H$_5$ | H | B2 | H |
| 82 | A9 | C$_2$H$_5$ | H | B3 | H |
| 83 | A9 | C$_2$H$_5$ | H | B4 | H |
| 84 | A9 | C$_2$H$_5$ | H | B5 | H |
| 85 | A9 | C$_2$H$_5$ | H | B6 | H |
| 86 | A9 | C$_3$H$_7$-i | H | B1 | H |
| 87 | A9 | C$_3$H$_7$-i | H | B2 | H |
| 88 | A9 | C$_3$H$_7$-i | H | B3 | H |
| 89 | A9 | C$_3$H$_7$-i | H | B4 | H |
| 90 | A9 | C$_3$H$_7$-i | H | B5 | H |
| 91 | A9 | C$_3$H$_7$-i | H | B6 | H |
| 92 | A9 | C$_4$H$_9$-t | H | B1 | H |
| 93 | A9 | C$_4$H$_9$-t | H | B2 | H |
| 94 | A9 | C$_4$H$_9$-t | H | B3 | H |
| 95 | A9 | C$_4$H$_9$-t | H | B4 | H |
| 96 | A9 | C$_4$H$_9$-t | H | B5 | H |
| 97 | A9 | C$_4$H$_9$-t | H | B6 | H |
| 98 | A9 | CH$_3$ | CH$_3$ | B1 | H |
| 99 | A9 | CH$_3$ | CH$_3$ | B2 | H |
| 100 | A9 | CH$_3$ | CH$_3$ | B3 | H |
| 101 | A9 | CH$_3$ | CH$_3$ | B4 | H |
| 102 | A9 | CH$_3$ | CH$_3$ | B5 | H |
| 103 | A9 | CH$_3$ | CH$_3$ | B6 | H |
| 104 | A9 | CH$_3$ | CH$_3$ | CH=C(CH$_3$)$_2$ | H |
| 105 | A9 | CH$_3$ | CH$_3$ | CH=CClCH$_3$ | H |
| 106 | A9 | CH$_3$ | CH$_3$ | OCH$_2$CH$_3$ | H |
| 107 | A9 | CH$_3$ | CH$_3$ | SCH$_2$CH$_3$ | H |
| 108 | A9 | CH$_3$ | CH$_3$ | OCH(CH$_3$)$_2$ | H |
| 109 | A9 | CH$_3$ | CH$_3$ | CH$_2$CH=CH$_2$ | H |
| 110 | A9 | CH$_3$ | CH$_3$ | CH$_2$C≡CH | H |
| 111 | A9 | CH$_3$ | CH$_3$ | O-Q1 | H |
| 112 | A9 | CH$_3$ | C$_2$H$_5$ | B1 | H |
| 113 | A9 | CH$_3$ | C$_2$H$_5$ | B2 | H |
| 114 | A9 | CH$_3$ | C$_2$H$_5$ | B3 | H |
| 115 | A9 | CH$_3$ | C$_2$H$_5$ | B4 | H |
| 116 | A9 | CH$_3$ | C$_2$H$_5$ | B5 | H |
| 117 | A9 | CH$_3$ | C$_2$H$_5$ | B6 | H |
| 118 | A9 | CH$_3$ | C$_3$H$_7$-i | B1 | H |
| 119 | A9 | CH$_3$ | C$_3$H$_7$-i | B2 | H |
| 120 | A9 | CH$_3$ | C$_3$H$_7$-i | B3 | H |
| 121 | A9 | CH$_3$ | C$_3$H$_7$-i | B4 | H |
| 122 | A9 | CH$_3$ | C$_3$H$_7$-i | B5 | H |
| 123 | A9 | CH$_3$ | C$_3$H$_7$-i | B6 | H |
| 124 | A9 | CH$_3$ | C$_4$H$_9$-t | B1 | H |
| 125 | A9 | CH$_3$ | C$_4$H$_9$-t | B2 | H |
| 126 | A9 | CH$_3$ | C$_4$H$_9$-t | B3 | H |
| 127 | A9 | CH$_3$ | C$_4$H$_9$-t | B4 | H |
| 128 | A9 | CH$_3$ | C$_4$H$_9$-t | B5 | H |
| 129 | A9 | CH$_3$ | C$_4$H$_9$-t | B6 | H |
| 130 | A9 | CH$_3$ | H | B1 | CH$_3$ |
| 131 | A9 | CH$_3$ | H | B2 | CH$_3$ |
| 132 | A9 | CH$_3$ | H | B3 | CH$_3$ |
| 133 | A9 | CH$_3$ | H | B4 | CH$_3$ |
| 134 | A9 | CH$_3$ | H | B5 | CH$_3$ |
| 135 | A9 | CH$_3$ | H | B6 | CH$_3$ |
| 136 | A9 | CH$_3$ | H | B3 | Q4 |
| 137 | A9 | CH$_3$ | H | B3 | Q55 |
| 138 | A9 | C$_2$H$_5$ | CH$_3$ | B1 | H |
| 139 | A9 | C$_2$H$_5$ | CH$_3$ | B2 | H |
| 140 | A9 | C$_2$H$_5$ | CH$_3$ | B3 | H |
| 141 | A9 | C$_2$H$_5$ | CH$_3$ | B4 | H |
| 142 | A9 | C$_2$H$_5$ | CH$_3$ | B5 | H |
| 143 | A9 | C$_2$H$_5$ | CH$_3$ | B6 | H |
| 144 | A9 | C$_3$H$_7$-i | CH$_3$ | B1 | H |
| 145 | A9 | C$_3$H$_7$-i | CH$_3$ | B2 | H |
| 146 | A9 | C$_3$H$_7$-i | CH$_3$ | B3 | H |
| 147 | A9 | C$_3$H$_7$-i | CH$_3$ | B4 | H |
| 148 | A9 | C$_3$H$_7$-i | CH$_3$ | B5 | H |
| 149 | A9 | C$_3$H$_7$-i | CH$_3$ | B6 | H |
| 150 | A10 | CH$_3$ | H | B1 | H |
| 151 | A10 | CH$_3$ | H | B2 | H |
| 152 | A10 | CH$_3$ | H | B3 | H |
| 153 | A10 | CH$_3$ | H | B4 | H |
| 154 | A10 | CH$_3$ | H | B5 | H |
| 155 | A10 | CH$_3$ | H | B6 | H |
| 156 | A10 | CH$_3$ | CH$_3$ | B1 | H |
| 157 | A10 | CH$_3$ | CH$_3$ | B2 | H |
| 158 | A10 | CH$_3$ | CH$_3$ | B3 | H |
| 159 | A10 | CH$_3$ | CH$_3$ | B4 | H |
| 160 | A10 | CH$_3$ | CH$_3$ | B5 | H |
| 161 | A10 | CH$_3$ | CH$_3$ | B6 | H |
| 162 | A10 | CH$_3$ | CH$_3$ | CH=C(CH$_3$)$_2$ | H |
| 163 | A10 | CH$_3$ | CH$_3$ | CH=CClCH$_3$ | H |
| 164 | A10 | CH$_3$ | CH$_3$ | OCH$_2$CH$_3$ | H |
| 165 | A10 | CH$_3$ | CH$_3$ | SCH$_2$CH$_3$ | H |
| 166 | A10 | CH$_3$ | CH$_3$ | OCH(CH$_3$)$_2$ | H |
| 167 | A10 | CH$_3$ | CH$_3$ | CH$_2$CH=CH$_2$ | H |
| 168 | A10 | CH$_3$ | CH$_3$ | CH$_2$C≡CH | H |
| 169 | A10 | CH$_3$ | CH$_3$ | B3 | CH$_3$ |
| 170 | A10 | CH$_3$ | CH$_3$ | B3 | CH$_3$ |
| 171 | A10 | CH$_3$ | CH$_3$ | B3 | Q4 |
| 172 | A10 | CH$_3$ | CH$_3$ | B3 | Q55 |
| 173 | A10 | C$_2$H$_5$ | CH$_3$ | B1 | H |
| 174 | A10 | C$_2$H$_5$ | CH$_3$ | B2 | H |
| 175 | A10 | C$_2$H$_5$ | CH$_3$ | B3 | H |
| 176 | A10 | C$_2$H$_5$ | CH$_3$ | B4 | H |
| 177 | A10 | C$_2$H$_5$ | CH$_3$ | B5 | H |
| 178 | A10 | C$_2$H$_5$ | CH$_3$ | B6 | H |
| 179 | A10 | C$_3$H$_7$-i | CH$_3$ | B1 | H |
| 180 | A10 | C$_3$H$_7$-i | CH$_3$ | B2 | H |
| 181 | A10 | C$_3$H$_7$-i | CH$_3$ | B3 | H |
| 182 | A10 | C$_3$H$_7$-i | CH$_3$ | B4 | H |
| 183 | A10 | C$_3$H$_7$-i | CH$_3$ | B5 | H |
| 184 | A10 | C$_3$H$_7$-i | CH$_3$ | B6 | H |
| 185 | A10 | C$_4$H$_9$-t | CH$_3$ | B1 | H |
| 186 | A10 | C$_4$H$_9$-t | CH$_3$ | B2 | H |
| 187 | A10 | C$_4$H$_9$-t | CH$_3$ | B3 | H |
| 188 | A10 | C$_4$H$_9$-t | CH$_3$ | B4 | H |
| 189 | A10 | C$_4$H$_9$-t | CH$_3$ | B5 | H |
| 190 | A10 | C$_4$H$_9$-t | CH$_3$ | B6 | H |

TABLE 3-continued

In a compound represented by the general formula:

$$A-CONHCH-C=NO-Y$$
$$\phantom{A-CONHCH-}|\phantom{-C=}|$$
$$\phantom{A-CONHCH-}B\phantom{-C}NH_2$$

| Compound No. | A | $R^1$ | $R^2$ | B | Y |
|---|---|---|---|---|---|
| 191 | A10 | $C_3H_7$-i | F | B3 | H |
| 192 | A10 | $C_3H_7$-i | Cl | B3 | H |
| 193 | A10 | $C_3H_7$-i | Br | B3 | H |
| 194 | A10 | $C_3H_7$-i | $CH_3SO$ | B3 | H |
| 195 | A10 | $C_3H_7$-i | $CH_3SO_2$ | B3 | H |
| 196 | A10 | $C_3H_7$-i | $NH_2$ | B3 | H |
| 197 | A10 | $C_3H_7$-i | $N(CH_3)_2$ | B3 | H |
| 198 | A10 | $C_3H_7$-i | $CF_3$ | B3 | H |
| 199 | A10 | $C_3H_7$-i | OH | B3 | H |
| 200 | A10 | $C_3H_7$-i | $OCH_3$ | B3 | H |
| 201 | A10 | $C_3H_7$-i | $C_3H_7$-i | B3 | H |
| 202 | A10 | $C_3H_7$-i | $C_4H_9$-t | B3 | H |
| 203 | A10 | $C_3H_7$-i | $C_2H_5$ | B3 | H |
| 204 | A10 | $C_3H_7$-i | Q1 | B3 | H |
| 205 | A10 | $C_3H_7$-i | Q2 | B3 | H |
| 206 | A10 | $C_3H_7$-i | Q3 | B3 | H |
| 207 | A10 | $C_3H_7$-i | Q4 | B3 | H |
| 208 | A10 | $C_3H_7$-i | $CH_3$ | $CH=C(CH_3)_2$ | H |
| 209 | A10 | $C_3H_7$-i | $CH_3$ | $CH=CClCH_3$ | H |
| 210 | A10 | $C_3H_7$-i | $CH_3$ | $OCH_2CH_3$ | H |
| 211 | A10 | $C_3H_7$-i | $CH_3$ | $SCH_2CH_3$ | H |
| 212 | A10 | $C_3H_7$-i | $CH_3$ | $OCH(CH_3)_2$ | H |
| 213 | A10 | $C_3H_7$-i | $CH_3$ | $CH_2CH=CH_2$ | H |
| 214 | A10 | $C_3H_7$-i | $CH_3$ | $CH_2C\equiv CH$ | H |
| 215 | A10 | $C_3H_7$-i | $CH_3$ | O-Q1 | H |
| 216 | A10 | $C_3H_7$-i | $CH_3$ | O-Q2 | H |
| 217 | A10 | $C_3H_7$-i | $CH_3$ | O-Q3 | H |
| 218 | A10 | $C_3H_7$-i | $CH_3$ | O-Q4 | H |
| 219 | A10 | $C_3H_7$-i | Q1 | B1 | H |
| 220 | A10 | $C_3H_7$-i | Q1 | B2 | H |
| 221 | A10 | $C_3H_7$-i | Q2 | B1 | H |
| 222 | A10 | $C_3H_7$-i | Q2 | B2 | H |
| 223 | A10 | $C_3H_7$-i | $CH_3$ | B1 | $CH_3$ |
| 224 | A10 | $C_3H_7$-i | $CH_3$ | B2 | $CH_3$ |
| 225 | A10 | $C_3H_7$-i | $CH_3$ | B3 | $CH_3$ |
| 226 | A10 | $C_3H_7$-i | $CH_3$ | B4 | $CH_3$ |
| 227 | A10 | $C_3H_7$-i | $CH_3$ | B5 | $CH_3$ |
| 228 | A10 | $C_3H_7$-i | $CH_3$ | B6 | $CH_3$ |
| 229 | A10 | $C_3H_7$-i | $CH_3$ | B1 | Q1 |
| 230 | A10 | $C_3H_7$-i | $CH_3$ | B1 | Q2 |
| 231 | A10 | $C_3H_7$-i | $CH_3$ | B1 | Q3 |
| 232 | A10 | $C_3H_7$-i | $CH_3$ | B1 | Q4 |
| 233 | A10 | $C_3H_7$-i | $CH_3$ | B1 | Q55 |
| 234 | A10 | $C_3H_7$-i | $CH_3$ | B2 | Q1 |
| 235 | A10 | $C_3H_7$-i | $CH_3$ | B2 | Q2 |
| 236 | A10 | $C_3H_7$-i | $CH_3$ | B2 | Q3 |
| 237 | A10 | $C_3H_7$-i | $CH_3$ | B2 | Q4 |
| 238 | A10 | $C_3H_7$-i | $CH_3$ | B2 | Q55 |
| 239 | A10 | $C_3H_7$-i | $CH_3$ | B3 | Q1 |
| 240 | A10 | $C_3H_7$-i | $CH_3$ | B3 | Q2 |
| 241 | A10 | $C_3H_7$-i | $CH_3$ | B3 | Q3 |
| 242 | A10 | $C_3H_7$-i | $CH_3$ | B3 | Q4 |
| 243 | A10 | $C_3H_7$-i | $CH_3$ | B3 | Q55 |
| 244 | A10 | $C_3H_7$-i | $CH_3$ | B4 | Q1 |
| 245 | A10 | $C_3H_7$-i | $CH_3$ | B4 | Q2 |
| 246 | A10 | $C_3H_7$-i | $CH_3$ | B4 | Q3 |
| 247 | A10 | $C_3H_7$-i | $CH_3$ | B4 | Q4 |
| 248 | A10 | $C_3H_7$-i | $CH_3$ | B4 | Q55 |
| 249 | A10 | $C_3H_7$-i | $CH_3$ | B5 | Q2 |
| 250 | A10 | $C_3H_7$-i | $CH_3$ | B5 | Q3 |
| 251 | A10 | $C_3H_7$-i | $CH_3$ | B5 | Q4 |
| 252 | A10 | $C_3H_7$-i | $CH_3$ | B5 | Q55 |
| 253 | A10 | $C_3H_7$-i | $CH_3$ | B6 | Q1 |
| 254 | A10 | $C_3H_7$-i | $CH_3$ | B6 | Q2 |
| 255 | A10 | $C_3H_7$-i | $CH_3$ | B6 | Q3 |
| 256 | A10 | $C_3H_7$-i | $CH_3$ | B6 | Q4 |
| 257 | A10 | $C_3H_7$-i | $CH_3$ | B6 | Q55 |
| 258 | A10 | $C_4H_9$-t | $CH_3$ | B1 | Q1 |
| 259 | A10 | $C_4H_9$-t | $CH_3$ | B1 | Q2 |
| 260 | A10 | $C_4H_9$-t | $CH_3$ | B1 | Q3 |
| 261 | A10 | $C_4H_9$-t | $CH_3$ | B1 | Q4 |
| 262 | A10 | $C_4H_9$-t | $CH_3$ | B1 | Q55 |
| 263 | A10 | $C_4H_9$-t | $CH_3$ | B2 | Q1 |
| 264 | A10 | $C_4H_9$-t | $CH_3$ | B2 | Q2 |
| 265 | A10 | $C_4H_9$-t | $CH_3$ | B2 | Q3 |
| 266 | A10 | $C_4H_9$-t | $CH_3$ | B2 | Q4 |
| 267 | A10 | $C_4H_9$-t | $CH_3$ | B2 | Q55 |
| 268 | A10 | $C_4H_9$-t | $CH_3$ | B3 | Q1 |
| 269 | A10 | $C_4H_9$-t | $CH_3$ | B3 | Q2 |
| 270 | A10 | $C_4H_9$-t | $CH_3$ | B3 | Q3 |
| 271 | A10 | $C_4H_9$-t | $CH_3$ | B3 | Q4 |
| 272 | A10 | $C_4H_9$-t | $CH_3$ | B3 | Q55 |
| 273 | A10 | $C_4H_9$-t | $CH_3$ | B4 | Q1 |
| 274 | A10 | $C_4H_9$-t | $CH_3$ | B4 | Q2 |
| 275 | A10 | $C_4H_9$-t | $CH_3$ | B4 | Q3 |
| 276 | A10 | $C_4H_9$-t | $CH_3$ | B4 | Q4 |
| 277 | A10 | $C_4H_9$-t | $CH_3$ | B4 | Q55 |
| 278 | A10 | $C_4H_9$-t | $CH_3$ | B5 | Q1 |
| 279 | A10 | $C_4H_9$-t | $CH_3$ | B5 | Q2 |
| 280 | A10 | $C_4H_9$-t | $CH_3$ | B5 | Q3 |
| 281 | A10 | $C_4H_9$-t | $CH_3$ | B5 | Q4 |
| 282 | A10 | $C_4H_9$-t | $CH_3$ | B5 | Q55 |
| 283 | A10 | $C_4H_9$-t | $CH_3$ | B6 | Q1 |
| 284 | A10 | $C_4H_9$-t | $CH_3$ | B6 | Q2 |
| 285 | A10 | $C_4H_9$-t | $CH_3$ | B6 | Q3 |
| 286 | A10 | $C_4H_9$-t | $CH_3$ | B6 | Q4 |
| 287 | A10 | $C_4H_9$-t | $CH_3$ | B6 | Q55 |
| 288 | A10 | $C_4H_9$-t | $CH_3$ | B4 | H |
| 289 | A10 | $C_4H_9$-t | $CH_3$ | B4 | H |
| 290 | A10 | Q1 | $CH_3$ | B3 | $CH_3$ |
| 291 | A10 | Q2 | $CH_3$ | B3 | $CH_3$ |
| 292 | A10 | Q3 | $CH_3$ | B3 | $CH_3$ |
| 293 | A10 | Q4 | $CH_3$ | B3 | $CH_3$ |
| 294 | A10 | Q55 | $CH_3$ | B3 | $CH_3$ |
| 295 | A10 | Q1 | $CH_3$ | B3 | Q1 |
| 296 | A10 | Q2 | $CH_3$ | B3 | Q1 |
| 297 | A10 | Q3 | $CH_3$ | B3 | Q1 |
| 298 | A10 | Q4 | $CH_3$ | B3 | Q1 |
| 299 | A10 | Q55 | $CH_3$ | B3 | Q1 |
| 300 | A10 | Q1 | $CH_3$ | B3 | Q55 |
| 301 | A10 | Q2 | $CH_3$ | B3 | Q55 |
| 302 | A10 | Q3 | $CH_3$ | B3 | Q55 |
| 303 | A10 | Q4 | $CH_3$ | B3 | Q55 |
| 304 | A10 | Q55 | $CH_3$ | B3 | Q55 |
| 305 | A10 | Q1 | $CH_3$ | B1 | H |
| 306 | A10 | Q2 | $CH_3$ | B1 | H |
| 307 | A10 | Q3 | $CH_3$ | B1 | H |
| 308 | A10 | Q4 | $CH_3$ | B1 | H |
| 309 | A10 | Q55 | $CH_3$ | B1 | H |
| 310 | A10 | Q1 | $CH_3$ | B2 | H |
| 311 | A10 | Q2 | $CH_3$ | B2 | H |
| 312 | A10 | Q3 | $CH_3$ | B2 | H |
| 313 | A10 | Q4 | $CH_3$ | B2 | H |
| 314 | A10 | Q55 | $CH_3$ | B2 | H |
| 315 | A10 | Q1 | $CH_3$ | B3 | H |
| 316 | A10 | Q2 | $CH_3$ | B3 | H |
| 317 | A10 | Q3 | $CH_3$ | B3 | H |
| 318 | A10 | Q4 | $CH_3$ | B3 | H |
| 319 | A10 | Q55 | $CH_3$ | B3 | H |
| 320 | A10 | Q1 | $CH_3$ | B4 | H |
| 321 | A10 | Q2 | $CH_3$ | B4 | H |
| 322 | A10 | Q3 | $CH_3$ | B4 | H |
| 323 | A10 | Q4 | $CH_3$ | B4 | H |
| 324 | A10 | Q55 | $CH_3$ | B4 | H |
| 325 | A10 | Q1 | $CH_3$ | B5 | H |
| 326 | A10 | Q2 | $CH_3$ | B5 | H |
| 327 | A10 | Q3 | $CH_3$ | B5 | H |
| 328 | A10 | Q4 | $CH_3$ | B5 | H |
| 329 | A10 | Q55 | $CH_3$ | B5 | H |
| 330 | A10 | Q1 | $CH_3$ | B6 | H |
| 331 | A10 | Q2 | $CH_3$ | B6 | H |
| 332 | A10 | Q3 | $CH_3$ | B6 | H |
| 333 | A10 | Q4 | $CH_3$ | B6 | H |
| 334 | A10 | Q55 | $CH_3$ | B6 | H |

TABLE 3-continued

In a compound represented by the general formula:

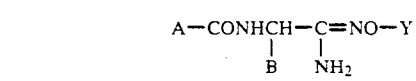

| Compound No. | A | R$^1$ | R$^2$ | B | Y |
|---|---|---|---|---|---|
| 335 | A10 | C$_3$H$_7$-n | CH$_3$ | B1 | H |
| 336 | A10 | C$_3$H$_7$-n | CH$_3$ | B2 | H |
| 337 | A10 | C$_3$H$_7$-n | CH$_3$ | B3 | H |
| 338 | A10 | C$_3$H$_7$-n | CH$_3$ | B4 | H |
| 339 | A10 | C$_3$H$_7$-n | CH$_3$ | B5 | H |
| 340 | A10 | C$_3$H$_7$-n | CH$_3$ | B6 | H |
| 341 | A10 | C$_4$H$_9$-s | CH$_3$ | B1 | H |
| 342 | A10 | C$_4$H$_9$-s | CH$_3$ | B2 | H |
| 343 | A10 | C$_4$H$_9$-s | CH$_3$ | B3 | H |
| 344 | A10 | C$_4$H$_9$-s | CH$_3$ | B4 | H |
| 345 | A10 | C$_4$H$_9$-s | CH$_3$ | B5 | H |
| 346 | A10 | CH$_2$F | CH$_3$ | B3 | H |
| 347 | A10 | CHF$_2$ | CH$_3$ | B3 | H |
| 348 | A10 | CF$_3$ | CH$_3$ | B3 | H |
| 349 | A10 | CH$_2$CH$_2$F | CH$_3$ | B3 | H |
| 350 | A10 | CH$_2$CHF$_2$ | CH$_3$ | B3 | H |
| 351 | A10 | CH$_2$CF$_3$ | CH$_3$ | B3 | H |
| 352 | A10 | CF=CF$_2$ | CH$_3$ | B3 | H |
| 353 | A10 | CH$_2$CN | CH$_3$ | B3 | H |
| 354 | A10 | COCH$_3$ | CH$_3$ | B3 | H |
| 355 | A10 | CON(CH$_3$)$_2$ | CH$_3$ | B3 | H |
| 356 | A10 | COCH$_2$OCH$_3$ | CH$_3$ | B3 | H |
| 357 | A10 | CH$_2$OH | CH$_3$ | B3 | H |
| 358 | A10 | CH$_2$COOCH$_3$ | CH$_3$ | B3 | H |
| 359 | A10 | Q56 | CH$_3$ | B3 | H |
| 360 | A10 | CH=CH$_2$ | CH$_3$ | B3 | H |
| 361 | A10 | CH=C=CH$_2$ | CH$_3$ | B3 | H |
| 362 | A10 | CH$_2$CH=CH$_2$ | CH$_3$ | B3 | H |
| 363 | A10 | CH$_2$C≡CH | CH$_3$ | B3 | H |
| 364 | A10 | CH$_2$Cl | CH$_3$ | B3 | H |
| 365 | A10 | CHClCH$_3$ | CH$_3$ | B3 | H |
| 366 | A11 | CH$_3$ | H | B3 | H |
| 367 | A11 | CH$_3$ | CH$_3$ | B3 | H |
| 368 | A11 | C$_2$H$_5$ | H | B3 | H |
| 369 | A11 | C$_2$H$_5$ | CH$_3$ | B3 | H |
| 370 | A12 | H | H | B3 | H |
| 371 | A12 | CH$_3$ | H | B3 | H |
| 372 | A12 | H | CH$_3$ | B3 | H |
| 373 | A12 | CH$_3$ | CH$_3$ | B3 | H |
| 374 | A13 | H | H | B3 | H |
| 375 | A13 | CH$_3$ | H | B3 | H |
| 376 | A13 | H | CH$_3$ | B3 | H |
| 377 | A13 | CH$_3$ | CH$_3$ | B3 | H |
| 378 | A14 | H | H | B3 | H |
| 379 | A14 | CH$_3$ | H | B3 | H |
| 380 | A14 | H | CH$_3$ | B3 | H |
| 381 | A14 | CH$_3$ | CH$_3$ | B3 | H |
| 382 | A15 | H | H | B3 | H |
| 383 | A15 | CH$_3$ | H | B3 | H |
| 384 | A15 | H | CH$_3$ | B3 | H |
| 385 | A15 | CH$_3$ | CH$_3$ | B3 | H |
| 386 | A15 | H | C$_3$H$_7$-i | B3 | H |
| 387 | A15 | H | C$_2$H$_5$ | B3 | H |
| 388 | A15 | CH$_3$ | C$_3$H$_7$-i | B3 | H |
| 389 | A15 | CH$_3$ | C$_2$H$_5$ | B3 | H |
| 390 | A16 | CH$_3$ | H | B3 | H |
| 391 | A16 | CH$_3$ | CH$_3$ | B3 | H |
| 392 | A17 | CH$_3$ | H | B1 | H |
| 393 | A17 | CH$_3$ | CH$_3$ | B1 | H |
| 394 | A17 | CH$_3$ | H | B2 | H |
| 395 | A17 | CH$_3$ | CH$_3$ | B2 | H |
| 396 | A17 | CH$_3$ | H | B3 | H |
| 397 | A17 | CH$_3$ | CH$_3$ | B3 | H |
| 398 | A17 | CH$_3$ | H | B4 | H |
| 399 | A17 | CH$_3$ | CH$_3$ | B4 | H |
| 400 | A17 | CH$_3$ | H | B5 | H |
| 401 | A17 | CH$_3$ | CH$_3$ | B5 | H |
| 402 | A17 | CH$_3$ | H | B6 | H |
| 403 | A17 | CH$_3$ | CH$_3$ | B6 | H |
| 404 | A17 | CH$_2$CH$_3$ | H | B3 | H |
| 405 | A17 | C$_3$H$_7$-i | CH$_3$ | B3 | H |
| 406 | A17 | C$_4$H$_9$-t | CH$_3$ | B3 | H |
| 407 | A17 | CH$_3$ | H | B3 | CH$_3$ |
| 408 | A17 | CH$_3$ | CH$_3$ | B3 | CH$_3$ |
| 409 | A17 | CH$_3$ | H | B3 | Q55 |
| 410 | A17 | CH$_3$ | CH$_3$ | B3 | Q55 |
| 411 | A18 | CH$_3$ | H | B3 | H |
| 412 | A18 | CH$_3$ | CH$_3$ | B3 | H |
| 413 | A19 | H | — | B3 | H |
| 414 | A19 | CH$_3$ | — | B3 | H |
| 415 | A20 | H | — | B3 | H |
| 416 | A20 | CH$_3$ | — | B3 | H |
| 417 | A21 | H | — | B3 | H |
| 418 | A21 | CH$_3$ | — | B3 | H |
| 419 | A22 | H | — | B3 | H |
| 420 | A22 | CH$_3$ | — | B3 | H |
| 421 | A23 | H | H | B1 | H |
| 422 | A23 | H | H | B2 | H |
| 423 | A23 | H | H | B3 | H |
| 424 | A23 | H | H | B4 | H |
| 425 | A23 | H | H | B5 | H |
| 426 | A23 | H | H | B6 | H |
| 427 | A24 | H | H | B1 | H |
| 428 | A24 | H | H | B2 | H |
| 429 | A24 | H | H | B3 | H |
| 430 | A24 | H | H | B4 | H |
| 431 | A24 | H | H | B5 | H |
| 432 | A24 | H | H | B6 | H |
| 433 | A25 | H | H | B1 | H |
| 434 | A25 | H | H | B2 | H |
| 435 | A25 | H | H | B3 | H |
| 436 | A25 | H | H | B4 | H |
| 437 | A25 | H | H | B5 | H |
| 438 | A25 | H | H | B6 | H |
| 439 | A9 | CH$_2$F | H | B5 | H |
| 440 | A10 | CH$_2$CH$_3$ | H | B1 | H |
| 441 | A10 | CH$_2$CH$_3$ | H | B2 | H |
| 442 | A10 | CH$_2$CH$_3$ | H | B3 | H |
| 443 | A10 | CH$_2$CH$_3$ | H | B4 | H |
| 444 | A10 | CH$_2$CH$_3$ | H | B5 | H |
| 445 | A10 | CH$_2$CH$_3$ | H | B6 | H |
| 446 | A10 | C$_3$H$_7$-i | H | B1 | H |
| 447 | A10 | C$_3$H$_7$-i | H | B2 | H |
| 448 | A10 | C$_3$H$_7$-i | H | B3 | H |
| 449 | A10 | C$_3$H$_7$-i | H | B4 | H |
| 450 | A10 | C$_3$H$_7$-i | H | B5 | H |
| 451 | A10 | C$_3$H$_7$-i | H | B6 | H |
| 452 | A10 | C$_4$H$_9$-t | H | B1 | H |
| 453 | A10 | C$_4$H$_9$-t | H | B2 | H |
| 454 | A10 | C$_4$H$_9$-t | H | B3 | H |
| 455 | A10 | C$_4$H$_9$-t | H | B4 | H |
| 456 | A10 | C$_4$H$_9$-t | H | B5 | H |
| 457 | A10 | C$_4$H$_9$-t | H | B6 | H |

TABLE 4

In a compound represented by the general formula:

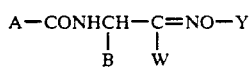

$$A-CONHCH-C=NO-Y$$
$$\quad\quad\quad\quad\;\; | \quad\;\; |$$
$$\quad\quad\quad\quad\;\; B \quad W$$

| Compound No. | A | R¹ | R² | B | W | Y |
|---|---|---|---|---|---|---|
| 1005 | A10 | Q5 | $CH_3$ | B1 | $NH_2$ | H |
| 1006 | A10 | Q5 | $CH_3$ | B2 | $NH_2$ | H |
| 1007 | A10 | Q5 | $CH_3$ | B3 | $NH_2$ | H |
| 1008 | A10 | Q5 | $CH_3$ | B4 | $NH_2$ | H |
| 1009 | A10 | Q5 | $CH_3$ | B5 | $NH_2$ | H |
| 1010 | A10 | Q5 | $CH_3$ | B6 | $NH_2$ | H |
| 1011 | A10 | $C_4H_9$-i | $CH_3$ | B1 | $NH_2$ | H |
| 1012 | A10 | $C_4H_9$-i | $CH_3$ | B2 | $NH_2$ | H |
| 1013 | A10 | $C_4H_9$-i | $CH_3$ | B3 | $NH_2$ | H |
| 1014 | A10 | $C_4H_9$-i | $CH_3$ | B4 | $NH_2$ | H |
| 1015 | A10 | $C_4H_9$-i | $CH_3$ | B5 | $NH_2$ | H |
| 1016 | A10 | $C_4H_9$-i | $CH_3$ | B6 | $NH_2$ | H |
| 1017 | A10 | $CH_3$ | $CH_3$ | B1 | F | H |
| 1018 | A10 | $CH_3$ | $CH_3$ | B2 | F | H |
| 1019 | A10 | $CH_3$ | $CH_3$ | B3 | F | H |
| 1020 | A10 | $CH_3$ | $CH_3$ | B4 | F | H |
| 1021 | A10 | $CH_3$ | $CH_3$ | B1 | Cl | H |
| 1022 | A10 | $CH_3$ | $CH_3$ | B2 | Cl | H |
| 1023 | A10 | $CH_3$ | $CH_3$ | B3 | Cl | H |
| 1024 | A10 | $CH_3$ | $CH_3$ | B4 | Cl | H |
| 1025 | A10 | $CH_3$ | $CH_3$ | B1 | Br | H |
| 1026 | A10 | $CH_3$ | $CH_3$ | B2 | Br | H |
| 1027 | A10 | $CH_3$ | $CH_3$ | B3 | Br | H |
| 1028 | A10 | $CH_3$ | $CH_3$ | B4 | Br | H |
| 1029 | A10 | $CH_3$ | $CH_3$ | B1 | I | H |
| 1030 | A10 | $CH_3$ | $CH_3$ | B2 | I | H |
| 1031 | A10 | $CH_3$ | $CH_3$ | B3 | I | H |
| 1032 | A10 | $CH_3$ | $CH_3$ | B4 | I | H |
| 1033 | A10 | $CH_3$ | $CH_3$ | B4 | $NH_2$ | $CH_3$ |
| 1034 | A10 | $CH_3$ | $CH_3$ | B4 | $NH_2$ | $CH_2CH=CH_2$ |
| 1035 | A10 | $CH_3$ | $CH_3$ | B4 | $NH_2$ | $C_4H_9$n |
| 1036 | A10 | $CH_3$ | $CH_3$ | B4 | $NH_2$ | $COCH_3$ |
| 1037 | A10 | $CH_3$ | $CH_3$ | B4 | $NH_2$ | $COC_6H_5$ |
| 1038 | A10 | $CH_3$ | $CH_3$ | B4 | $NH_2$ | $CONHCH_3$ |
| 1039 | A10 | $CH_3$ | $CH_3$ | B4 | $NH_2$ | $CONHCH(CH_3)_2$ |
| 1040 | A10 | $CH_3$ | $CH_3$ | B4 | $NH_2$ | $CONHC_6H_5$ |
| 1041 | A10 | $CH_3$ | $CH_3$ | B4 | $NH_2$ | $CONHC_6H_4Cl$-p |
| 1042 | A10 | $CH_3$ | $CH_3$ | B4 | $NH_2$ | $CSNHCH_3$ |
| 1043 | A10 | $CH_3$ | $CH_3$ | B4 | $NH_2$ | $CO_2C_2H_5$ |
| 1044 | A10 | $CH_3$ | $CH_3$ | B4 | $NHCH_3$ | H |
| 1045 | A10 | $CH_3$ | $CH_3$ | B4 | $NHC_6H_5$ | H |
| 1046 | A10 | $CH_3$ | $CH_3$ | B4 | NHQ6 | H |
| 1047 | A10 | $CH_3$ | $CH_3$ | B4 | $NH_2$ | H |
| 1048 | A10 | $CH_3$ | $CH_3$ | B4 | $SO_2CH_3$ | H |
| 1049 | A10 | $CH_3$ | $CH_3$ | B4 | $SO_2C_6H_5CH_3$-p | H |
| 1050 | A10 | $CH_3$ | $CH_3$ | B4 | $SO_2N(CH_3)_2$ | H |
| 1051 | A1 | H | H | B1 | H | H |
| 1052 | A1 | H | H | B2 | H | H |
| 1053 | A1 | H | H | B3 | H | H |
| 1054 | A1 | H | H | B4 | H | H |
| 1055 | A1 | 3-Cl | 5-Cl | B1 | H | H |
| 1056 | A1 | 3-Cl | 5-Cl | B2 | H | H |
| 1057 | A1 | 3-Cl | 5-Cl | B3 | H | H |
| 1058 | A1 | 3-Cl | 5-Cl | B4 | H | H |
| 1059 | A2 | H | H | B1 | H | H |
| 1060 | A2 | H | H | B2 | H | H |
| 1061 | A2 | H | H | B3 | H | H |
| 1062 | A2 | H | H | B4 | H | H |
| 1063 | A3 | H | H | B1 | H | H |
| 1064 | A3 | H | H | B2 | H | H |
| 1065 | A3 | H | H | B3 | H | H |
| 1066 | A3 | H | H | B4 | H | H |
| 1067 | A4 | H | H | B1 | H | H |
| 1068 | A4 | H | H | B2 | H | H |
| 1069 | A4 | H | H | B3 | H | H |
| 1070 | A4 | H | H | B4 | H | H |
| 1071 | A5 | H | H | B1 | H | H |
| 1072 | A5 | H | H | B2 | H | H |
| 1073 | A5 | H | H | B3 | H | H |
| 1074 | A5 | H | H | B4 | H | H |
| 1075 | A6 | H | H | B1 | H | H |
| 1076 | A6 | H | H | B2 | H | H |
| 1077 | A6 | H | H | B3 | H | H |
| 1078 | A6 | H | H | B4 | H | H |

TABLE 4-continued

In a compound represented by the general formula:

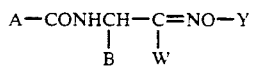

| Compound No. | A | R$^1$ | R$^2$ | B | W | Y |
|---|---|---|---|---|---|---|
| 1079 | A7 | CH$_3$ | H | B1 | H | H |
| 1080 | A7 | CH$_3$ | H | B2 | H | H |
| 1081 | A7 | CH$_3$ | H | B3 | H | H |
| 1082 | A7 | CH$_3$ | H | B4 | H | H |
| 1083 | A8 | CH$_3$ | H | B1 | H | H |
| 1084 | A8 | CH$_3$ | H | B2 | H | H |
| 1085 | A8 | CH$_3$ | H | B3 | H | H |
| 1086 | A8 | CH$_3$ | H | B4 | H | H |
| 1087 | A9 | CH$_3$ | H | B1 | H | H |
| 1088 | A9 | CH$_3$ | H | B2 | H | H |
| 1089 | A9 | CH$_3$ | H | B3 | H | H |
| 1090 | A9 | CH$_3$ | H | B4 | H | H |
| 1091 | A9 | CH$_3$ | H | B5 | H | H |
| 1092 | A9 | CH$_3$ | H | B6 | H | H |
| 1093 | A9 | CH$_3$ | H | CH=C(CH$_3$)$_2$ | H | H |
| 1094 | A9 | CH$_3$ | H | CH=CClCH$_3$ | H | H |
| 1095 | A9 | CH$_3$ | H | OCH$_2$CH$_3$ | H | H |
| 1096 | A9 | CH$_3$ | H | SCH$_2$CH$_3$ | H | H |
| 1097 | A9 | CH$_3$ | H | OCH(CH$_3$)$_2$ | H | H |
| 1098 | A9 | CH$_3$ | H | CH$_2$CH=CH$_2$ | H | H |
| 1099 | A9 | CH$_3$ | H | CH$_2$C≡CH | H | H |
| 1100 | A9 | CH$_3$ | H | OQ1 | H | H |
| 1101 | A9 | CH$_3$ | H | OQ2 | H | H |
| 1102 | A9 | CH$_3$ | H | OQ3 | H | H |
| 1103 | A9 | CH$_3$ | H | OQ4 | H | H |
| 1104 | A9 | CH$_3$ | CH$_3$ | B1 | H | H |
| 1105 | A9 | CH$_3$ | CH$_3$ | B2 | H | H |
| 1106 | A9 | CH$_3$ | CH$_3$ | B3 | H | H |
| 1107 | A9 | CH$_3$ | CH$_3$ | B4 | H | H |
| 1108 | A9 | CH$_3$ | CH$_3$ | B5 | H | H |
| 1109 | A9 | CH$_3$ | CH$_3$ | B6 | H | H |
| 1110 | A9 | CH$_3$ | CH$_3$ | CH=C(CH$_3$)$_2$ | H | H |
| 1111 | A9 | CH$_3$ | CH$_3$ | CH=CClCH$_3$ | H | H |
| 1112 | A9 | CH$_3$ | CH$_3$ | OCH$_2$CH$_3$ | H | H |
| 1113 | A9 | CH$_3$ | CH$_3$ | SCH$_2$CH$_3$ | H | H |
| 1114 | A9 | CH$_3$ | CH$_3$ | OCH(CH$_3$)$_2$ | H | H |
| 1115 | A9 | CH$_3$ | CH$_3$ | CH$_2$CH=CH$_2$ | H | H |
| 1116 | A9 | CH$_3$ | CH$_3$ | CH$_2$C≡CH | H | H |
| 1117 | A9 | CH$_3$ | CH$_3$ | OQ1 | H | H |
| 1118 | A9 | CH$_3$ | CH$_3$ | OQ2 | H | H |
| 1119 | A9 | CH$_3$ | CH$_3$ | OQ3 | H | H |
| 1120 | A9 | CH$_3$ | CH$_3$ | OQ4 | H | H |
| 1121 | A10 | CH$_3$ | CH$_3$ | B1 | H | H |
| 1122 | A10 | CH$_3$ | CH$_3$ | B2 | H | H |
| 1123 | A10 | CH$_3$ | CH$_3$ | B3 | H | H |
| 1124 | A10 | CH$_3$ | CH$_3$ | B4 | H | H |
| 1125 | A10 | CH$_3$ | CH$_3$ | B5 | H | H |
| 1126 | A10 | CH$_3$ | CH$_3$ | B6 | H | H |
| 1127 | A10 | CH$_3$ | CH$_3$ | CH=C(CH$_3$)$_2$ | H | H |
| 1128 | A10 | CH$_3$ | CH$_3$ | CH=CClCH$_3$ | H | H |
| 1129 | A10 | CH$_3$ | CH$_3$ | OCH$_2$CH$_3$ | H | H |
| 1130 | A10 | CH$_3$ | CH$_3$ | SCH$_2$CH$_3$ | H | H |
| 1131 | A10 | CH$_3$ | CH$_3$ | OCH(CH$_3$)$_2$ | H | H |
| 1132 | A10 | CH$_3$ | CH$_3$ | CH$_2$CH=CH$_2$ | H | H |
| 1133 | A10 | CH$_3$ | CH$_3$ | CH$_2$C≡CH | H | H |
| 1134 | A10 | CH$_3$ | CH$_3$ | OQ1 | H | H |
| 1135 | A10 | CH$_3$ | CH$_3$ | OQ2 | H | H |
| 1136 | A10 | CH$_3$ | CH$_3$ | OQ3 | H | H |
| 1137 | A10 | CH$_3$ | CH$_3$ | OQ4 | H | H |
| 1138 | A10 | C$_2$H$_5$ | CH$_3$ | B1 | H | H |
| 1139 | A10 | C$_2$H$_5$ | CH$_3$ | B2 | H | H |
| 1140 | A10 | C$_2$H$_5$ | CH$_3$ | B3 | H | H |
| 1141 | A10 | C$_2$H$_5$ | CH$_3$ | B4 | H | H |
| 1142 | A10 | C$_2$H$_5$ | CH$_3$ | B5 | H | H |
| 1143 | A10 | C$_2$H$_5$ | CH$_3$ | B6 | H | H |
| 1144 | A10 | C$_2$H$_5$ | CH$_3$ | CH=C(CH$_3$)$_2$ | H | H |
| 1145 | A10 | C$_2$H$_5$ | CH$_3$ | CH=CClCH$_3$ | H | H |
| 1146 | A10 | C$_2$H$_5$ | CH$_3$ | OCH$_2$CH$_3$ | H | H |
| 1147 | A10 | C$_2$H$_5$ | CH$_3$ | SCH$_2$CH$_3$ | H | H |
| 1148 | A10 | C$_2$H$_5$ | CH$_3$ | OCH(CH$_3$)$_2$ | H | H |
| 1149 | A10 | C$_2$H$_5$ | CH$_3$ | CH$_2$CH=CH$_2$ | H | H |
| 1150 | A10 | C$_2$H$_5$ | CH$_3$ | CH$_2$C≡CH | H | H |
| 1151 | A10 | C$_2$H$_5$ | CH$_3$ | OQ1 | H | H |
| 1152 | A10 | C$_2$H$_5$ | CH$_3$ | OQ2 | H | H |

TABLE 4-continued

In a compound represented by the general formula:

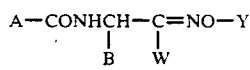

A—CONHCH—C=NO—Y
　　　　　|　　|
　　　　　B　 W

| Compound No. | A | R¹ | R² | B | W | Y |
|---|---|---|---|---|---|---|
| 1153 | A10 | $C_2H_5$ | $CH_3$ | OQ3 | H | H |
| 1154 | A10 | $C_2H_5$ | $CH_3$ | OQ4 | H | H |
| 1155 | A10 | $C_3H_7$-i | $CH_3$ | B1 | H | H |
| 1156 | A10 | $C_3H_7$-i | $CH_3$ | B2 | H | H |
| 1157 | A10 | $C_3H_7$-i | $CH_3$ | B3 | H | H |
| 1158 | A10 | $C_3H_7$-i | $CH_3$ | B4 | H | H |
| 1159 | A10 | $C_3H_7$-i | $CH_3$ | B5 | H | H |
| 1160 | A10 | $C_3H_7$-i | $CH_3$ | B6 | H | H |
| 1161 | A10 | $C_3H_7$-i | $CH_3$ | $CH=C(CH_3)_2$ | H | H |
| 1162 | A10 | $C_3H_7$-i | $CH_3$ | $CH=CClCH_3$ | H | H |
| 1163 | A10 | $C_3H_7$-i | $CH_3$ | $OCH_2CH_3$ | H | H |
| 1164 | A10 | $C_3H_7$-i | $CH_3$ | $SCH_2CH_3$ | H | H |
| 1165 | A10 | $C_3H_7$-i | $CH_3$ | $OCH(CH_3)_2$ | H | H |
| 1166 | A10 | $C_3H_7$-i | $CH_3$ | $CH_2CH=CH_2$ | H | H |
| 1167 | A10 | $C_3H_7$-i | $CH_3$ | $CH_2C\equiv CH$ | H | H |
| 1168 | A10 | $C_3H_7$-i | $CH_3$ | OQ1 | H | H |
| 1169 | A10 | $C_3H_7$-i | $CH_3$ | OQ2 | H | H |
| 1170 | A10 | $C_3H_7$-i | $CH_3$ | OQ3 | H | H |
| 1171 | A10 | $C_3H_7$-i | $CH_3$ | OQ4 | H | H |
| 1172 | A10 | Q1 | $CH_3$ | B1 | H | H |
| 1173 | A10 | Q1 | $CH_3$ | B2 | H | H |
| 1174 | A10 | Q1 | $CH_3$ | B3 | H | H |
| 1175 | A10 | Q1 | $CH_3$ | B4 | H | H |
| 1176 | A10 | Q1 | $CH_3$ | B5 | H | H |
| 1177 | A10 | Q1 | $CH_3$ | B6 | H | H |
| 1178 | A10 | Q1 | $CH_3$ | $CH=C(CH_3)_2$ | H | H |
| 1179 | A10 | Q1 | $CH_3$ | $CH=CClCH_3$ | H | H |
| 1180 | A10 | Q1 | $CH_3$ | $OCH_2CH_3$ | H | H |
| 1181 | A10 | Q1 | $CH_3$ | $SCH_2CH_3$ | H | H |
| 1182 | A10 | Q1 | $CH_3$ | $OCH(CH_3)_2$ | H | H |
| 1183 | A10 | Q1 | $CH_3$ | $CH_2CH=CH_2$ | H | H |
| 1184 | A10 | Q1 | $CH_3$ | $CH_2C\equiv CH$ | H | H |
| 1185 | A10 | Q1 | $CH_3$ | OQ1 | H | H |
| 1186 | A10 | Q1 | $CH_3$ | OQ2 | H | H |
| 1187 | A10 | Q1 | $CH_3$ | OQ3 | H | H |
| 1188 | A10 | Q1 | $CH_3$ | OQ4 | H | H |
| 1189 | A10 | Q2 | $CH_3$ | B1 | H | H |
| 1190 | A10 | Q2 | $CH_3$ | B2 | H | H |
| 1191 | A10 | Q2 | $CH_3$ | B3 | H | H |
| 1192 | A10 | Q2 | $CH_3$ | B4 | H | H |
| 1193 | A10 | Q2 | $CH_3$ | B5 | H | H |
| 1194 | A10 | Q2 | $CH_3$ | B6 | H | H |
| 1195 | A10 | Q2 | $CH_3$ | $CH=C(CH_3)_2$ | H | H |
| 1196 | A10 | Q2 | $CH_3$ | $CH=CClCH_3$ | H | H |
| 1197 | A10 | Q2 | $CH_3$ | $OCH_2CH_3$ | H | H |
| 1198 | A10 | Q2 | $CH_3$ | $SCH_2CH_3$ | H | H |
| 1199 | A10 | Q2 | $CH_3$ | $OCH(CH_3)_2$ | H | H |
| 1200 | A10 | Q2 | $CH_3$ | $CH_2CH=CH_2$ | H | H |
| 1201 | A10 | Q2 | $CH_3$ | $CH_2C\equiv CH$ | H | H |
| 1202 | A10 | Q2 | $CH_3$ | OQ1 | H | H |
| 1203 | A10 | Q2 | $CH_3$ | OQ2 | H | H |
| 1204 | A10 | Q2 | $CH_3$ | OQ3 | H | H |
| 1205 | A10 | Q2 | $CH_3$ | OQ4 | H | H |
| 1206 | A10 | Q3 | $CH_3$ | B1 | H | H |
| 1207 | A10 | Q3 | $CH_3$ | B2 | H | H |
| 1208 | A10 | Q3 | $CH_3$ | B3 | H | H |
| 1209 | A10 | Q3 | $CH_3$ | B4 | H | H |
| 1210 | A10 | Q3 | $CH_3$ | B5 | H | H |
| 1211 | A10 | Q3 | $CH_3$ | B6 | H | H |
| 1212 | A10 | Q3 | $CH_3$ | $CH=C(CH_3)_2$ | H | H |
| 1213 | A10 | Q3 | $CH_3$ | $CH=CClCH_3$ | H | H |
| 1214 | A10 | Q3 | $CH_3$ | $OCH_2CH_3$ | H | H |
| 1215 | A10 | Q3 | $CH_3$ | $SCH_2CH_3$ | H | H |
| 1216 | A10 | Q3 | $CH_3$ | $OCH(CH_3)_2$ | H | H |
| 1217 | A10 | Q3 | $CH_3$ | $CH_2CH=CH_2$ | H | H |
| 1218 | A10 | Q3 | $CH_3$ | $CH_2C\equiv CH$ | H | H |
| 1219 | A10 | Q3 | $CH_3$ | OQ1 | H | H |
| 1220 | A10 | Q3 | $CH_3$ | OQ2 | H | H |
| 1221 | A10 | Q3 | $CH_3$ | OQ3 | H | H |
| 1222 | A10 | Q3 | $CH_3$ | OQ4 | H | H |
| 1223 | A10 | Q4 | $CH_3$ | B1 | H | H |
| 1224 | A10 | Q4 | $CH_3$ | B2 | H | H |
| 1225 | A10 | Q4 | $CH_3$ | B3 | H | H |
| 1226 | A10 | Q4 | $CH_3$ | B4 | H | H |

TABLE 4-continued

In a compound represented by the general formula:

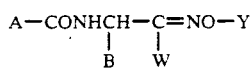

| Compound No. | A | R[1] | R[2] | B | W | Y |
|---|---|---|---|---|---|---|
| 1227 | A10 | Q4 | CH$_3$ | B5 | H | H |
| 1228 | A10 | Q4 | CH$_3$ | B6 | H | H |
| 1229 | A10 | Q4 | CH$_3$ | CH=C(CH$_3$)$_2$ | H | H |
| 1230 | A10 | Q4 | CH$_3$ | CH=CClCH$_3$ | H | H |
| 1231 | A10 | Q4 | CH$_3$ | OCH$_2$CH$_3$ | H | H |
| 1232 | A10 | Q4 | CH$_3$ | SCH$_2$CH$_3$ | H | H |
| 1233 | A10 | Q4 | CH$_3$ | OCH(CH$_3$)$_2$ | H | H |
| 1234 | A10 | Q4 | CH$_3$ | CH$_2$CH=CH$_2$ | H | H |
| 1235 | A10 | Q4 | CH$_3$ | CH$_2$C≡CH | H | H |
| 1236 | A10 | Q4 | CH$_3$ | OQ1 | H | H |
| 1237 | A10 | Q4 | CH$_3$ | OQ2 | H | H |
| 1238 | A10 | Q4 | CH$_3$ | OQ3 | H | H |
| 1239 | A10 | Q4 | CH$_3$ | OQ4 | H | H |
| 1240 | A10 | Q5 | CH$_3$ | B1 | H | H |
| 1241 | A10 | Q5 | CH$_3$ | B2 | H | H |
| 1242 | A10 | Q5 | CH$_3$ | B3 | H | H |
| 1243 | A10 | Q5 | CH$_3$ | B4 | H | H |
| 1244 | A10 | Q5 | CH$_3$ | B5 | H | H |
| 1245 | A10 | Q5 | CH$_3$ | B6 | H | H |
| 1246 | A10 | Q5 | CH$_3$ | CH=C(CH$_3$)$_2$ | H | H |
| 1247 | A10 | Q5 | CH$_3$ | CH=CClCH$_3$ | H | H |
| 1248 | A10 | Q5 | CH$_3$ | OCH$_2$CH$_3$ | H | H |
| 1249 | A10 | Q5 | CH$_3$ | SCH$_2$CH$_3$ | H | H |
| 1250 | A10 | Q5 | CH$_3$ | OCH(CH$_3$)$_2$ | H | H |
| 1251 | A10 | Q5 | CH$_3$ | CH$_2$CH=CH$_2$ | H | H |
| 1252 | A10 | Q5 | CH$_3$ | CH$_2$C≡CH | H | H |
| 1253 | A10 | Q5 | CH$_3$ | OQ1 | H | H |
| 1254 | A10 | Q5 | CH$_3$ | OQ2 | H | H |
| 1255 | A10 | Q5 | CH$_3$ | OQ3 | H | H |
| 1256 | A10 | Q5 | CH$_3$ | OQ4 | H | H |
| 1257 | A10 | Q6 | CH$_3$ | B1 | H | H |
| 1258 | A10 | Q6 | CH$_3$ | B2 | H | H |
| 1259 | A10 | Q6 | CH$_3$ | B3 | H | H |
| 1260 | A10 | Q6 | CH$_3$ | B4 | H | H |
| 1261 | A10 | Q6 | CH$_3$ | B5 | H | H |
| 1262 | A10 | Q6 | CH$_3$ | B6 | H | H |
| 1263 | A10 | Q6 | CH$_3$ | CH=C(CH$_3$)$_2$ | H | H |
| 1264 | A10 | Q6 | CH$_3$ | CH=CClCH$_3$ | H | H |
| 1265 | A10 | Q6 | CH$_3$ | OCH$_2$CH$_3$ | H | H |
| 1266 | A10 | Q6 | CH$_3$ | SCH$_2$CH$_3$ | H | H |
| 1267 | A10 | Q6 | CH$_3$ | OCH(CH$_3$)$_2$ | H | H |
| 1268 | A10 | Q6 | CH$_3$ | CH$_2$CH=CH$_2$ | H | H |
| 1269 | A10 | Q6 | CH$_3$ | CH$_2$C≡CH | H | H |
| 1270 | A10 | Q6 | CH$_3$ | OQ1 | H | H |
| 1271 | A10 | Q6 | CH$_3$ | OQ2 | H | H |
| 1272 | A10 | Q6 | CH$_3$ | OQ3 | H | H |
| 1273 | A10 | Q6 | CH$_3$ | OQ4 | H | H |
| 1274 | A10 | CH$_2$F | CH$_3$ | OQ4 | H. | H |
| 1275 | A10 | CH$_2$OCH$_3$ | CH$_3$ | B3 | H | H |
| 1276 | A10 | Q7 | CH$_3$ | B3 | H | H |
| 1277 | A10 | Q8 | CH$_3$ | B3 | H | H |
| 1278 | A10 | Q9 | CH$_3$ | B3 | H | H |
| 1279 | A10 | Q10 | CH$_3$ | B3 | H | H |
| 1280 | A10 | Q11 | CH$_3$ | B3 | H | H |
| 1281 | A10 | Q12 | CH$_3$ | B3 | H | H |
| 1282 | A10 | Q13 | CH$_3$ | B3 | H | H |
| 1283 | A10 | Q14 | CH$_3$ | B3 | H | H |
| 1284 | A10 | Q15 | CH$_3$ | B3 | H | H |
| 1285 | A10 | Q16 | CH$_3$ | B3 | H | H |
| 1286 | A10 | Q17 | CH$_3$ | B3 | H | H |
| 1287 | A10 | Q18 | CH$_3$ | B3 | H | H |
| 1288 | A10 | Q19 | CH$_3$ | B3 | H | H |
| 1289 | A10 | Q20 | CH$_3$ | B3 | H | H |
| 1290 | A10 | Q21 | CH$_3$ | B3 | H | H |
| 1291 | A10 | Q22 | CH$_3$ | B3 | H | H |
| 1292 | A10 | Q23 | CH$_3$ | B3 | H | H |
| 1293 | A10 | Q24 | CH$_3$ | B3 | H | H |
| 1294 | A10 | Q25 | CH$_3$ | B3 | H | H |
| 1295 | A10 | Q26 | CH$_3$ | B3 | H | H |
| 1296 | A10 | Q27 | CH$_3$ | B3 | H | H |
| 1297 | A10 | Q28 | CH$_3$ | B3 | H | H |
| 1298 | A10 | Q29 | CH$_3$ | B3 | H | H |
| 1299 | A10 | Q30 | CH$_3$ | B3 | H | H |
| 1300 | A10 | Q31 | CH$_3$ | B3 | H | H |

TABLE 4-continued

In a compound represented by the general formula:

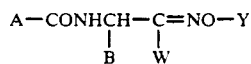

A—CONHCH—C=NO—Y
　　　　　|　　|
　　　　　B　 W

| Compound No. | A | R¹ | R² | B | W | Y |
|---|---|---|---|---|---|---|
| 1301 | A10 | Q32 | CH₃ | B3 | H | H |
| 1302 | A10 | Q33 | CH₃ | B3 | H | H |
| 1303 | A10 | Q34 | CH₃ | B3 | H | H |
| 1304 | A10 | Q35 | CH₃ | B3 | H | H |
| 1305 | A10 | Q36 | CH₃ | B3 | H | H |
| 1306 | A10 | Q37 | CH₃ | B3 | H | H |
| 1307 | A10 | Q38 | CH₃ | B3 | H | H |
| 1308 | A10 | Q39 | CH₃ | B3 | H | H |
| 1309 | A10 | Q40 | CH₃ | B3 | H | H |
| 1310 | A10 | Q41 | CH₃ | B3 | H | H |
| 1311 | A10 | Q42 | CH₃ | B3 | H | H |
| 1312 | A10 | Q43 | CH₃ | B3 | H | H |
| 1313 | A10 | Q44 | CH₃ | B3 | H | H |
| 1314 | A10 | Q45 | CH₃ | B3 | H | H |
| 1315 | A10 | Q46 | CH₃ | B3 | H | H |
| 1316 | A10 | Q47 | CH₃ | B3 | H | H |
| 1317 | A10 | Q48 | CH₃ | B3 | H | H |
| 1318 | A10 | Q49 | CH₃ | B3 | H | H |
| 1319 | A10 | Q50 | CH₃ | B3 | H | H |
| 1320 | A10 | Q51 | CH₃ | B3 | H | H |
| 1321 | A10 | Q52 | CH₃ | B3 | H | H |
| 1322 | A10 | Q53 | CH₃ | B3 | H | H |
| 1323 | A10 | Q54 | CH₃ | B3 | H | H |
| 1324 | A11 | CH₃ | H | B3 | H | H |
| 1325 | A11 | CH₃ | CH₃ | B3 | H | H |
| 1326 | A12 | H | H | B3 | H | H |
| 1327 | A12 | CH₃ | H | B3 | H | H |
| 1328 | A12 | H | CH₃ | B3 | H | H |
| 1329 | A12 | CH₃ | CH₃ | B3 | H | H |
| 1330 | A13 | H | H | B3 | H | H |
| 1331 | A13 | CH₃ | H | B3 | H | H |
| 1332 | A13 | H | CH₃ | B3 | H | H |
| 1333 | A13 | CH₃ | CH₃ | B3 | H | H |
| 1334 | A14 | H | H | B3 | H | H |
| 1335 | A14 | CH₃ | H | B3 | H | H |
| 1336 | A14 | H | CH₃ | B3 | H | H |
| 1337 | A15 | H | H | B3 | H | H |
| 1338 | A15 | CH₃ | H | B3 | H | H |
| 1339 | A15 | H | CH₃ | B3 | H | H |
| 1340 | A15 | CH₃ | CH₃ | B3 | H | H |
| 1341 | A16 | CH₃ | H | B3 | H | H |
| 1342 | A16 | CH₃ | CH₃ | B3 | H | H |
| 1343 | A17 | CH₃ | H | B3 | H | H |
| 1344 | A17 | CH₃ | CH₃ | B3 | H | H |
| 1345 | A18 | CH₃ | CH₃ | B3 | H | H |
| 1346 | A18 | CH₃ | CH₃ | B3 | H | H |
| 1347 | A19 | H | — | B3 | H | H |
| 1348 | A19 | CH₃ | — | B3 | H | H |
| 1349 | A20 | H | — | B3 | H | H |
| 1350 | A20 | CH₃ | — | B3 | H | H |
| 1351 | A21 | H | — | B3 | H | H |
| 1352 | A21 | CH₃ | — | B3 | H | H |
| 1353 | A22 | H | — | B3 | H | H |
| 1354 | A22 | CH₃ | — | B3 | H | H |
| 1355 | A23 | H | H | B3 | H | H |
| 1356 | A24 | H | H | B3 | H | H |
| 1357 | A25 | H | H | B3 | H | H |
| 1364 | A10 | Q1 | CH₃ | CH=C(CH₃)₂ | NH₂ | H |
| 1365 | A10 | Q1 | CH₃ | CH=CClCH₃ | NH₂ | H |
| 1366 | A10 | Q1 | CH₃ | OCH₂CH₃ | NH₂ | H |
| 1367 | A10 | Q1 | CH₃ | SCH₂CH₃ | NH₂ | H |
| 1368 | A10 | Q1 | CH₃ | OCH(CH₃)₂ | NH₂ | H |
| 1369 | A10 | Q1 | CH₃ | CH₂CH=CH₂ | NH₂ | H |
| 1370 | A10 | Q1 | CH₃ | CH₂C≡CH | NH₂ | H |
| 1371 | A10 | Q1 | CH₃ | OQ1 | NH₂ | H |
| 1372 | A10 | Q1 | CH₃ | OQ2 | NH₂ | H |
| 1373 | A10 | Q1 | CH₃ | OQ3 | NH₂ | H |
| 1374 | A10 | Q1 | CH₃ | OQ4 | NH₂ | H |
| 1381 | A10 | Q2 | CH₃ | CH=C(CH₃)₂ | NH₂ | H |
| 1382 | A10 | Q2 | CH₃ | CH=CClCH₃ | NH₂ | H |
| 1383 | A10 | Q2 | CH₃ | OCH₂CH₃ | NH₂ | H |
| 1384 | A10 | Q2 | CH₃ | SCH₂CH₃ | NH₂ | H |
| 1385 | A10 | Q2 | CH₃ | OCH(CH₃)₂ | NH₂ | H |
| 1386 | A10 | Q2 | CH₃ | CH₂CH=CH₂ | NH₂ | H |

TABLE 4-continued

In a compound represented by the general formula:

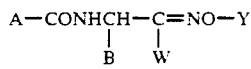

| Compound No. | A | R¹ | R² | B | W | Y |
|---|---|---|---|---|---|---|
| 1387 | A10 | Q2 | $CH_3$ | $CH_2C\equiv CH$ | $NH_2$ | H |
| 1388 | A10 | Q2 | $CH_3$ | OQ1 | $NH_2$ | H |
| 1389 | A10 | Q2 | $CH_3$ | OQ2 | $NH_2$ | H |
| 1390 | A10 | Q2 | $CH_3$ | OQ3 | $NH_2$ | H |
| 1391 | A10 | Q3 | $CH_3$ | OQ4 | $NH_2$ | H |
| 1395 | A10 | Q3 | $CH_3$ | $CH=C(CH_3)_2$ | $NH_2$ | H |
| 1396 | A10 | Q3 | $CH_3$ | $CH=CClCH_3$ | $NH_2$ | H |
| 1397 | A10 | Q3 | $CH_3$ | $OCH_2CH_3$ | $NH_2$ | H |
| 1398 | A10 | Q3 | $CH_3$ | $SCH_2CH_3$ | $NH_2$ | H |
| 1399 | A10 | Q3 | $CH_3$ | $OCH(CH_3)_2$ | $NH_2$ | H |
| 1400 | A10 | Q3 | $CH_3$ | $CH_2CH=CH_2$ | $NH_2$ | H |
| 1401 | A10 | Q3 | $CH_3$ | $CH_2C\equiv CH$ | $NH_2$ | H |
| 1402 | A10 | Q3 | $CH_3$ | OQ1 | $NH_2$ | H |
| 1403 | A10 | Q3 | $CH_3$ | OQ2 | $NH_2$ | H |
| 1409 | A10 | Q4 | $CH_3$ | $CH=C(CH_3)_2$ | $NH_2$ | H |
| 1410 | A10 | Q4 | $CH_3$ | $CH=CClCH_3$ | $NH_2$ | H |
| 1411 | A10 | Q4 | $CH_3$ | $OCH_2CH_3$ | $NH_2$ | H |
| 1412 | A10 | Q4 | $CH_3$ | $SCH_2CH_3$ | $NH_2$ | H |
| 1413 | A10 | Q4 | $CH_3$ | $OCH(CH_3)_2$ | $NH_2$ | H |
| 1414 | A10 | Q4 | $CH_3$ | $CH_2CH=CH_2$ | $NH_2$ | H |
| 1415 | A10 | Q4 | $CH_3$ | $CH_2C\equiv CH$ | $NH_2$ | H |
| 1416 | A10 | Q4 | $CH_3$ | OQ1 | $NH_2$ | H |
| 1417 | A10 | Q4 | $CH_3$ | OQ2 | $NH_2$ | H |
| 1418 | A10 | Q4 | $CH_3$ | OQ3 | $NH_2$ | H |
| 1419 | A10 | Q4 | $CH_3$ | OQ4 | $NH_2$ | H |
| 1420 | A10 | Q6 | $CH_3$ | B1 | $NH_2$ | H |
| 1421 | A10 | Q6 | $CH_3$ | B2 | $NH_2$ | H |
| 1422 | A10 | Q6 | $CH_3$ | B3 | $NH_2$ | H |
| 1423 | A10 | Q6 | $CH_3$ | B4 | $NH_2$ | H |
| 1424 | A10 | Q6 | $CH_3$ | B5 | $NH_2$ | H |
| 1425 | A10 | Q7 | $CH_3$ | B1 | $NH_2$ | H |
| 1426 | A10 | Q7 | $CH_3$ | B2 | $NH_2$ | H |
| 1427 | A10 | Q7 | $CH_3$ | B3 | $NH_2$ | H |
| 1428 | A10 | Q7 | $CH_3$ | B4 | $NH_2$ | H |
| 1429 | A10 | Q7 | $CH_3$ | B5 | $NH_2$ | H |
| 1430 | A10 | Q10 | $CH_3$ | B1 | $NH_2$ | H |
| 1431 | A10 | Q10 | $CH_3$ | B2 | $NH_2$ | H |
| 1432 | A10 | Q10 | $CH_3$ | B3 | $NH_2$ | H |
| 1433 | A10 | Q10 | $CH_3$ | B4 | $NH_2$ | H |
| 1434 | A10 | Q10 | $CH_3$ | B5 | $NH_2$ | H |
| 1435 | A10 | Q11 | $CH_3$ | B1 | $NH_2$ | H |
| 1436 | A10 | Q11 | $CH_3$ | B2 | $NH_2$ | H |
| 1437 | A10 | Q11 | $CH_3$ | B3 | $NH_2$ | H |
| 1438 | A10 | Q11 | $CH_3$ | B4 | $NH_2$ | H |
| 1439 | A10 | Q11 | $CH_3$ | B5 | $NH_2$ | H |
| 1440 | A10 | Q12 | $CH_3$ | B1 | $NH_2$ | H |
| 1441 | A10 | Q12 | $CH_3$ | B2 | $NH_2$ | H |
| 1442 | A10 | Q12 | $CH_3$ | B3 | $NH_2$ | H |
| 1443 | A10 | Q12 | $CH_3$ | B4 | $NH_2$ | H |
| 1444 | A10 | Q12 | $CH_3$ | B5 | $NH_2$ | H |
| 1445 | A10 | Q14 | $CH_3$ | B1 | $NH_2$ | H |
| 1446 | A10 | Q14 | $CH_3$ | B2 | $NH_2$ | H |
| 1447 | A10 | Q14 | $CH_3$ | B3 | $NH_2$ | H |
| 1448 | A10 | Q14 | $CH_3$ | B4 | $NH_2$ | H |
| 1449 | A10 | Q14 | $CH_3$ | B5 | $NH_2$ | H |
| 1450 | A10 | Q8 | $CH_3$ | B1 | $NH_2$ | H |
| 1451 | A10 | Q8 | $CH_3$ | B2 | $NH_2$ | H |
| 1452 | A10 | Q8 | $CH_3$ | B3 | $NH_2$ | H |
| 1453 | A10 | Q8 | $CH_3$ | B4 | $NH_2$ | H |
| 1454 | A10 | Q9 | $CH_3$ | B1 | $NH_2$ | H |
| 1455 | A10 | Q9 | $CH_3$ | B2 | $NH_2$ | H |
| 1456 | A10 | Q9 | $CH_3$ | B3 | $NH_2$ | H |
| 1457 | A10 | Q9 | $CH_3$ | B4 | $NH_2$ | H |
| 1458 | A10 | Q13 | $CH_3$ | B1 | $NH_2$ | H |
| 1459 | A10 | Q13 | $CH_3$ | B2 | $NH_2$ | H |
| 1460 | A10 | Q13 | $CH_3$ | B3 | $NH_2$ | H |
| 1461 | A10 | Q13 | $CH_3$ | B4 | $NH_2$ | H |
| 1462 | A10 | Q15 | $CH_3$ | B1 | $NH_2$ | H |
| 1463 | A10 | Q15 | $CH_3$ | B2 | $NH_2$ | H |
| 1464 | A10 | Q15 | $CH_3$ | B3 | $NH_2$ | H |
| 1465 | A10 | Q15 | $CH_3$ | B4 | $NH_2$ | H |
| 1466 | A10 | Q16 | $CH_3$ | B1 | $NH_2$ | H |
| 1467 | A10 | Q16 | $CH_3$ | B2 | $NH_2$ | H |
| 1468 | A10 | Q16 | $CH_3$ | B3 | $NH_2$ | H |

TABLE 4-continued

In a compound represented by the general formula:

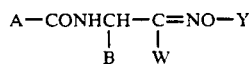

| Compound No. | A | R¹ | R² | B | W | Y |
|---|---|---|---|---|---|---|
| 1469 | A10 | Q16 | $CH_3$ | B4 | $NH_2$ | H |
| 1470 | A10 | Q17 | $CH_3$ | B1 | $NH_2$ | H |
| 1471 | A10 | Q17 | $CH_3$ | B2 | $NH_2$ | H |
| 1472 | A10 | Q17 | $CH_3$ | B3 | $NH_2$ | H |
| 1473 | A10 | Q17 | $CH_3$ | B4 | $NH_2$ | H |
| 1474 | A10 | Q18 | $CH_3$ | B1 | $NH_2$ | H |
| 1475 | A10 | Q18 | $CH_3$ | B2 | $NH_2$ | H |
| 1476 | A10 | Q18 | $CH_3$ | B3 | $NH_2$ | H |
| 1477 | A10 | Q18 | $CH_3$ | B4 | $NH_2$ | H |
| 1478 | A10 | Q19 | $CH_3$ | B1 | $NH_2$ | H |
| 1479 | A10 | Q19 | $CH_3$ | B2 | $NH_2$ | H |
| 1480 | A10 | Q19 | $CH_3$ | B3 | $NH_2$ | H |
| 1481 | A10 | Q19 | $CH_3$ | B4 | $NH_2$ | H |
| 1482 | A10 | Q20 | $CH_3$ | B1 | $NH_2$ | H |
| 1483 | A10 | Q20 | $CH_3$ | B2 | $NH_2$ | H |
| 1484 | A10 | Q20 | $CH_3$ | B3 | $NH_2$ | H |
| 1485 | A10 | Q20 | $CH_3$ | B4 | $NH_2$ | H |
| 1486 | A10 | Q21 | $CH_3$ | B1 | $NH_2$ | H |
| 1487 | A10 | Q21 | $CH_3$ | B2 | $NH_2$ | H |
| 1488 | A10 | Q21 | $CH_3$ | B3 | $NH_2$ | H |
| 1489 | A10 | Q21 | $CH_3$ | B4 | $NH_2$ | H |
| 1490 | A10 | Q22 | $CH_3$ | B1 | $NH_2$ | H |
| 1491 | A10 | Q22 | $CH_3$ | B2 | $NH_2$ | H |
| 1492 | A10 | Q22 | $CH_3$ | B3 | $NH_2$ | H |
| 1493 | A10 | Q22 | $CH_3$ | B4 | $NH_2$ | H |
| 1494 | A10 | Q23 | $CH_3$ | B1 | $NH_2$ | H |
| 1495 | A10 | Q23 | $CH_3$ | B2 | $NH_2$ | H |
| 1496 | A10 | Q23 | $CH_3$ | B3 | $NH_2$ | H |
| 1497 | A10 | Q23 | $CH_3$ | B4 | $NH_2$ | H |
| 1498 | A10 | Q24 | $CH_3$ | B1 | $NH_2$ | H |
| 1499 | A10 | Q24 | $CH_3$ | B2 | $NH_2$ | H |
| 1500 | A10 | Q24 | $CH_3$ | B3 | $NH_2$ | H |
| 1501 | A10 | Q24 | $CH_3$ | B4 | $NH_2$ | H |
| 1502 | A10 | Q26 | $CH_3$ | B1 | $NH_2$ | H |
| 1503 | A10 | Q26 | $CH_3$ | B2 | $NH_2$ | H |
| 1504 | A10 | Q26 | $CH_3$ | B3 | $NH_2$ | H |
| 1505 | A10 | Q26 | $CH_3$ | B4 | $NH_2$ | H |
| 1506 | A10 | Q27 | $CH_3$ | B1 | $NH_2$ | H |
| 1507 | A10 | Q27 | $CH_3$ | B2 | $NH_2$ | H |
| 1508 | A10 | Q27 | $CH_3$ | B3 | $NH_2$ | H |
| 1509 | A10 | Q27 | $CH_3$ | B4 | $NH_2$ | H |
| 1510 | A10 | Q28 | $CH_3$ | B1 | $NH_2$ | H |
| 1511 | A10 | Q28 | $CH_3$ | B2 | $NH_2$ | H |
| 1512 | A10 | Q28 | $CH_3$ | B3 | $NH_2$ | H |
| 1513 | A10 | Q29 | $CH_3$ | B1 | $NH_2$ | H |
| 1514 | A10 | Q29 | $CH_3$ | B2 | $NH_2$ | H |
| 1515 | A10 | Q29 | $CH_3$ | B3 | $NH_2$ | H |
| 1516 | A10 | Q29 | $CH_3$ | B4 | $NH_2$ | H |
| 1517 | A10 | Q30 | $CH_3$ | B1 | $NH_2$ | H |
| 1518 | A10 | Q30 | $CH_3$ | B2 | $NH_2$ | H |
| 1519 | A10 | Q30 | $CH_3$ | B3 | $NH_2$ | H |
| 1510 | A10 | Q30 | $CH_3$ | B4 | $NH_2$ | H |
| 1521 | A10 | Q31 | $CH_3$ | B1 | $NH_2$ | H |
| 1522 | A10 | Q31 | $CH_3$ | B2 | $NH_2$ | H |
| 1523 | A10 | Q31 | $CH_3$ | B3 | $NH_2$ | H |
| 1524 | A10 | Q31 | $CH_3$ | B4 | $NH_2$ | H |
| 1525 | A10 | Q32 | $CH_3$ | B1 | $NH_2$ | H |
| 1526 | A10 | Q33 | $CH_3$ | B2 | $NH_2$ | H |
| 1527 | A10 | Q33 | $CH_3$ | B3 | $NH_2$ | H |
| 1528 | A10 | Q33 | $CH_3$ | B4 | $NH_2$ | H |
| 1529 | A10 | Q34 | $CH_3$ | B1 | $NH_2$ | H |
| 1520 | A10 | Q34 | $CH_3$ | B2 | $NH_2$ | H |
| 1521 | A10 | Q34 | $CH_3$ | B3 | $NH_2$ | H |
| 1532 | A10 | Q34 | $CH_3$ | B4 | $NH_2$ | H |
| 1533 | A10 | Q35 | $CH_3$ | B1 | $NH_2$ | H |
| 1534 | A10 | Q35 | $CH_3$ | B2 | $NH_2$ | H |
| 1535 | A10 | Q35 | $CH_3$ | B3 | $NH_2$ | H |
| 1536 | A10 | Q35 | $CH_3$ | B4 | $NH_2$ | H |
| 1537 | A10 | Q36 | $CH_3$ | B1 | $NH_2$ | H |
| 1538 | A10 | Q36 | $CH_3$ | B2 | $NH_2$ | H |
| 1539 | A10 | Q36 | $CH_3$ | B3 | $NH_2$ | H |
| 1530 | A10 | Q36 | $CH_3$ | B4 | $NH_2$ | H |
| 1531 | A10 | Q37 | $CH_3$ | B1 | $NH_2$ | H |
| 1532 | A10 | Q37 | $CH_3$ | B2 | $NH_2$ | H |

TABLE 4-continued

In a compound represented by the general formula:

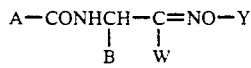

A—CONHCH—C=NO—Y
　　　　　|　　|
　　　　　B　 W

| Compound No. | A | R¹ | R² | B | W | Y |
|---|---|---|---|---|---|---|
| 1543 | A10 | Q37 | $CH_3$ | B3 | $NH_2$ | H |
| 1544 | A10 | Q37 | $CH_3$ | B4 | $NH_2$ | H |
| 1545 | A10 | Q38 | $CH_3$ | B1 | $NH_2$ | H |
| 1546 | A10 | Q38 | $CH_3$ | B2 | $NH_2$ | H |
| 1547 | A10 | Q38 | $CH_3$ | B3 | $NH_2$ | H |
| 1548 | A10 | Q39 | $CH_3$ | B1 | $NH_2$ | H |
| 1549 | A10 | Q39 | $CH_3$ | B2 | $NH_2$ | H |
| 1550 | A10 | Q39 | $CH_3$ | B3 | $NH_2$ | H |
| 1551 | A10 | Q39 | $CH_3$ | B4 | $NH_2$ | H |
| 1552 | A10 | Q40 | $CH_3$ | B1 | $NH_2$ | H |
| 1553 | A10 | Q40 | $CH_3$ | B2 | $NH_2$ | H |
| 1554 | A10 | Q40 | $CH_3$ | B3 | $NH_2$ | H |
| 1555 | A10 | Q40 | $CH_3$ | B4 | $NH_2$ | H |
| 1556 | A10 | Q41 | $CH_3$ | B1 | $NH_2$ | H |
| 1557 | A10 | Q41 | $CH_3$ | B2 | $NH_2$ | H |
| 1558 | A10 | Q41 | $CH_3$ | B3 | $NH_2$ | H |
| 1559 | A10 | Q41 | $CH_3$ | B4 | $NH_2$ | H |
| 1560 | A10 | Q42 | $CH_3$ | B1 | $NH_2$ | H |
| 1561 | A10 | Q43 | $CH_3$ | B2 | $NH_2$ | H |
| 1562 | A10 | Q43 | $CH_3$ | B3 | $NH_2$ | H |
| 1563 | A10 | Q43 | $CH_3$ | B4 | $NH_2$ | H |
| 1564 | A10 | Q44 | $CH_3$ | B1 | $NH_2$ | H |
| 1565 | A10 | Q44 | $CH_3$ | B2 | $NH_2$ | H |
| 1566 | A10 | Q44 | $CH_3$ | B3 | $NH_2$ | H |
| 1567 | A10 | Q44 | $CH_3$ | B4 | $NH_2$ | H |
| 1568 | A10 | Q45 | $CH_3$ | B1 | $NH_2$ | H |
| 1569 | A10 | Q45 | $CH_3$ | B2 | $NH_2$ | H |
| 1570 | A10 | Q45 | $CH_3$ | B3 | $NH_2$ | H |
| 1571 | A10 | Q45 | $CH_3$ | B4 | $NH_2$ | H |
| 1572 | A10 | Q46 | $CH_3$ | B1 | $NH_2$ | H |
| 1573 | A10 | Q46 | $CH_3$ | B2 | $NH_2$ | H |
| 1574 | A10 | Q46 | $CH_3$ | B3 | $NH_2$ | H |
| 1575 | A10 | Q46 | $CH_3$ | B4 | $NH_2$ | H |
| 1576 | A10 | Q47 | $CH_3$ | B1 | $NH_2$ | H |
| 1577 | A10 | Q47 | $CH_3$ | B2 | $NH_2$ | H |
| 1578 | A10 | Q47 | $CH_3$ | B3 | $NH_2$ | H |
| 1579 | A10 | Q47 | $CH_3$ | B4 | $NH_2$ | H |
| 1580 | A10 | Q48 | $CH_3$ | B1 | $NH_2$ | H |
| 1581 | A10 | Q48 | $CH_3$ | B2 | $NH_2$ | H |
| 1582 | A10 | Q48 | $CH_3$ | B3 | $NH_2$ | H |
| 1583 | A10 | Q49 | $CH_3$ | B1 | $NH_2$ | H |
| 1584 | A10 | Q49 | $CH_3$ | B2 | $NH_2$ | H |
| 1585 | A10 | Q49 | $CH_3$ | B3 | $NH_2$ | H |
| 1586 | A10 | Q49 | $CH_3$ | B4 | $NH_2$ | H |
| 1587 | A10 | Q50 | $CH_3$ | B1 | $NH_2$ | H |
| 1588 | A10 | Q50 | $CH_3$ | B2 | $NH_2$ | H |
| 1589 | A10 | Q50 | $CH_3$ | B3 | $NH_2$ | H |
| 1590 | A10 | Q50 | $CH_3$ | B4 | $NH_2$ | H |
| 1591 | A10 | Q51 | $CH_3$ | B1 | $NH_2$ | H |
| 1592 | A10 | Q51 | $CH_3$ | B2 | $NH_2$ | H |
| 1593 | A10 | Q51 | $CH_3$ | B3 | $NH_2$ | H |
| 1594 | A10 | Q51 | $CH_3$ | B4 | $NH_2$ | H |
| 1595 | A10 | Q52 | $CH_3$ | B1 | $NH_2$ | H |
| 1596 | A10 | Q53 | $CH_3$ | B2 | $NH_2$ | H |
| 1597 | A10 | Q53 | $CH_3$ | B3 | $NH_2$ | H |
| 1598 | A10 | Q53 | $CH_3$ | B4 | $NH_2$ | H |
| 1599 | A10 | Q54 | $CH_3$ | B1 | $NH_2$ | H |
| 1600 | A10 | Q54 | $CH_3$ | B2 | $NH_2$ | H |
| 1601 | A10 | Q54 | $CH_3$ | B3 | $NH_2$ | H |
| 1602 | A10 | Q54 | $CH_3$ | B4 | $NH_2$ | H |
| 1603 | A9 | $CH_3$ | Q1 | B1 | $NH_2$ | H |
| 1604 | A9 | $CH_3$ | Q2 | B1 | $NH_2$ | H |
| 1605 | A9 | $CH_3$ | Q3 | B1 | $NH_2$ | H |
| 1606 | A9 | $CH_3$ | Q4 | B1 | $NH_2$ | H |
| 1607 | A9 | $CH_3$ | Q44 | B1 | $NH_2$ | H |
| 1608 | A9 | $CH_3$ | Q46 | B1 | $NH_2$ | H |
| 1609 | A9 | $CH_3$ | Q47 | B1 | $NH_2$ | H |
| 1610 | A9 | $CH_3$ | Q1 | B2 | $NH_2$ | H |
| 1611 | A9 | $CH_3$ | Q2 | B2 | $NH_2$ | H |
| 1612 | A9 | $CH_3$ | Q3 | B2 | $NH_2$ | H |
| 1613 | A9 | $CH_3$ | Q4 | B2 | $NH_2$ | H |
| 1614 | A9 | $CH_3$ | Q44 | B2 | $NH_2$ | H |
| 1615 | A9 | $CH_3$ | Q46 | B2 | $NH_2$ | H |
| 1616 | A9 | $CH_3$ | Q47 | B2 | $NH_2$ | H |

TABLE 4-continued

In a compound represented by the general formula:

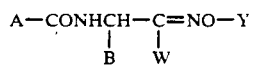

| Compound No. | A | R¹ | R² | B | W | Y |
|---|---|---|---|---|---|---|
| 1617 | A9 | $CH_3$ | Q1 | B3 | $NH_2$ | H |
| 1618 | A9 | $CH_3$ | Q2 | B3 | $NH_2$ | H |
| 1619 | A9 | $CH_3$ | Q3 | B3 | $NH_2$ | H |
| 1620 | A9 | $CH_3$ | Q4 | B3 | $NH_2$ | H |
| 1621 | A9 | $CH_3$ | Q44 | B3 | $NH_2$ | H |
| 1622 | A9 | $CH_3$ | Q46 | B3 | $NH_2$ | H |
| 1623 | A9 | $CH_3$ | Q47 | B3 | $NH_2$ | H |
| 1624 | A9 | $CH_3$ | Q1 | B4 | $NH_2$ | H |
| 1625 | A9 | $CH_3$ | Q2 | B4 | $NH_2$ | H |
| 1626 | A9 | $CH_3$ | Q3 | B4 | $NH_2$ | H |
| 1627 | A9 | $CH_3$ | Q4 | B4 | $NH_2$ | H |
| 1628 | A9 | $CH_3$ | Q44 | B4 | $NH_2$ | H |
| 1629 | A9 | $CH_3$ | Q46 | B4 | $NH_2$ | H |
| 1630 | A9 | $CH_3$ | Q47 | B4 | $NH_2$ | H |
| 1631 | A9 | $C_2H_5$ | Q1 | B1 | $NH_2$ | H |
| 1632 | A9 | $C_2H_5$ | Q2 | B1 | $NH_2$ | H |
| 1633 | A9 | $C_2H_5$ | Q3 | B1 | $NH_2$ | H |
| 1634 | A9 | $C_2H_5$ | Q4 | B1 | $NH_2$ | H |
| 1635 | A9 | $C_2H_5$ | Q44 | B1 | $NH_2$ | H |
| 1636 | A9 | $C_2H_5$ | Q46 | B1 | $NH_2$ | H |
| 1637 | A9 | $C_2H_5$ | Q47 | B1 | $NH_2$ | H |
| 1638 | A9 | $C_2H_5$ | Q1 | B2 | $NH_2$ | H |
| 1639 | A9 | $C_2H_5$ | Q2 | B2 | $NH_2$ | H |
| 1640 | A9 | $C_2H_5$ | Q3 | B2 | $NH_2$ | H |
| 1641 | A9 | $C_2H_5$ | Q4 | B2 | $NH_2$ | H |
| 1642 | A9 | $C_2H_5$ | Q44 | B2 | $NH_2$ | H |
| 1643 | A9 | $C_2H_5$ | Q46 | B2 | $NH_2$ | H |
| 1644 | A9 | $C_2H_5$ | Q47 | B2 | $NH_2$ | H |
| 1645 | A9 | $C_2H_5$ | Q1 | B3 | $NH_2$ | H |
| 1646 | A9 | $C_2H_5$ | Q2 | B3 | $NH_2$ | H |
| 1647 | A9 | $C_2H_5$ | Q3 | B3 | $NH_2$ | H |
| 1648 | A9 | $C_2H_5$ | Q4 | B3 | $NH_2$ | H |
| 1649 | A9 | $C_2H_5$ | Q44 | B3 | $NH_2$ | H |
| 1650 | A9 | $C_2H_5$ | Q46 | B3 | $NH_2$ | H |
| 1651 | A9 | $C_2H_5$ | Q47 | B3 | $NH_2$ | H |
| 1652 | A10 | $C_2H_5$ | Q1 | B4 | $NH_2$ | H |
| 1653 | A10 | $C_2H_5$ | Q2 | B4 | $NH_2$ | H |
| 1654 | A10 | $C_2H_5$ | Q3 | B4 | $NH_2$ | H |
| 1655 | A10 | $C_2H_5$ | Q4 | B4 | $NH_2$ | H |
| 1656 | A10 | $C_2H_5$ | Q44 | B4 | $NH_2$ | H |
| 1657 | A10 | $C_2H_5$ | Q46 | B4 | $NH_2$ | H |
| 1658 | A10 | $C_2H_5$ | Q47 | B4 | $NH_2$ | H |
| 1659 | A9 | $C_3H_7$-i | Q1 | B1 | $NH_2$ | H |
| 1660 | A9 | $C_3H_7$-i | Q2 | B1 | $NH_2$ | H |
| 1661 | A9 | $C_3H_7$-i | Q3 | B1 | $NH_2$ | H |
| 1662 | A9 | $C_3H_7$-i | Q4 | B1 | $NH_2$ | H |
| 1663 | A9 | $C_3H_7$-i | Q44 | B1 | $NH_2$ | H |
| 1664 | A9 | $C_3H_7$-i | Q46 | B1 | $NH_2$ | H |
| 1665 | A9 | $C_3H_7$-i | Q47 | B1 | $NH_2$ | H |
| 1666 | A9 | $C_3H_7$-i | Q1 | B2 | $NH_2$ | H |
| 1667 | A9 | $C_3H_7$-i | Q2 | B2 | $NH_2$ | H |
| 1668 | A9 | $C_3H_7$-i | Q3 | B2 | $NH_2$ | H |
| 1669 | A9 | $C_3H_7$-i | Q4 | B2 | $NH_2$ | H |
| 1670 | A9 | $C_3H_7$-i | Q44 | B2 | $NH_2$ | H |
| 1671 | A9 | $C_3H_7$-i | Q46 | B2 | $NH_2$ | H |
| 1672 | A9 | $C_3H_7$-i | Q47 | B2 | $NH_2$ | H |
| 1673 | A9 | $C_3H_7$-i | Q1 | B3 | $NH_2$ | H |
| 1674 | A9 | $C_3H_7$-i | Q2 | B3 | $NH_2$ | H |
| 1675 | A9 | $C_3H_7$-i | Q3 | B3 | $NH_2$ | H |
| 1676 | A9 | $C_3H_7$-i | Q4 | B3 | $NH_2$ | H |
| 1677 | A9 | $C_3H_7$-i | Q44 | B3 | $NH_2$ | H |
| 1678 | A9 | $C_3H_7$-i | Q46 | B3 | $NH_2$ | H |
| 1679 | A9 | $C_3H_7$-i | Q47 | B3 | $NH_2$ | H |
| 1680 | A9 | $C_3H_7$-i | Q1 | B4 | $NH_2$ | H |
| 1681 | A9 | $C_3H_7$-i | Q2 | B4 | $NH_2$ | H |
| 1682 | A9 | $C_3H_7$-i | Q3 | B4 | $NH_2$ | H |
| 1683 | A9 | $C_3H_7$-i | Q4 | B4 | $NH_2$ | H |
| 1684 | A9 | $C_3H_7$-i | Q44 | B4 | $NH_2$ | H |
| 1685 | A9 | $C_3H_7$-i | Q46 | B4 | $NH_2$ | H |
| 1686 | A9 | $C_3H_7$-i | Q47 | B4 | $NH_2$ | H |
| 1687 | A9 | $C_3H_7$-i | $CH_3$ | B4 | $NH_2$ | H |
| 1688 | A9 | Q1 | H | B1 | $NH_2$ | H |
| 1689 | A9 | Q2 | H | B1 | $NH_2$ | H |
| 1690 | A9 | Q3 | H | B1 | $NH_2$ | H |

TABLE 4-continued

In a compound represented by the general formula:

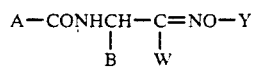

| Compound No. | A | R¹ | R² | B | W | Y |
|---|---|---|---|---|---|---|
| 1691 | A9 | Q4 | H | B1 | NH$_2$ | H |
| 1692 | A9 | Q44 | H | B1 | NH$_2$ | H |
| 1693 | A9 | Q46 | H | B1 | NH$_2$ | H |
| 1694 | A9 | Q47 | H | B1 | NH$_2$ | H |
| 1695 | A9 | Q1 | H | B2 | NH$_2$ | H |
| 1696 | A9 | Q2 | H | B2 | NH$_2$ | H |
| 1697 | A9 | Q3 | H | B2 | NH$_2$ | H |
| 1698 | A9 | Q4 | H | B2 | NH$_2$ | H |
| 1699 | A9 | Q44 | H | B2 | NH$_2$ | H |
| 1700 | A9 | Q46 | H | B2 | NH$_2$ | H |
| 1701 | A9 | Q47 | H | B2 | NH$_2$ | H |
| 1702 | A9 | Q1 | H | B3 | NH$_2$ | H |
| 1703 | A9 | Q2 | H | B3 | NH$_2$ | H |
| 1704 | A9 | Q3 | H | B3 | NH$_2$ | H |
| 1705 | A9 | Q4 | H | B3 | NH$_2$ | H |
| 1706 | A9 | Q44 | H | B3 | NH$_2$ | H |
| 1707 | A9 | Q46 | H | B3 | NH$_2$ | H |
| 1708 | A9 | Q47 | H | B3 | NH$_2$ | H |
| 1709 | A9 | Q1 | H | B4 | NH$_2$ | H |
| 1710 | A9 | Q2 | H | B4 | NH$_2$ | H |
| 1711 | A9 | Q3 | H | B4 | NH$_2$ | H |
| 1712 | A9 | Q4 | H | B4 | NH$_2$ | H |
| 1713 | A9 | Q44 | H | B4 | NH$_2$ | H |
| 1714 | A9 | Q46 | H | B4 | NH$_2$ | H |
| 1715 | A9 | Q47 | H | B4 | NH$_2$ | H |
| 1716 | A10 | Q57 | CH$_3$ | B1 | NH$_2$ | H |
| 1717 | A10 | Q57 | CH$_3$ | B2 | NH$_2$ | H |
| 1718 | A10 | Q57 | CH$_3$ | B3 | NH$_2$ | H |
| 1719 | A10 | Q57 | CH$_3$ | B4 | NH$_2$ | H |
| 1720 | A10 | Q57 | CH$_3$ | B5 | NH$_2$ | H |
| 1721 | A10 | Q57 | CH$_3$ | B6 | NH$_2$ | H |

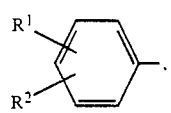 A1

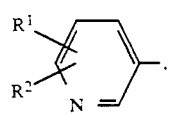 A2

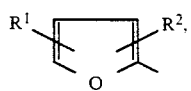 A3

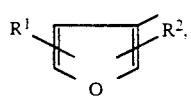 A4

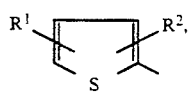 A5

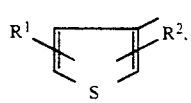 A6

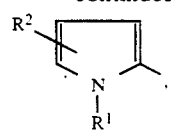 A7

-continued

A8

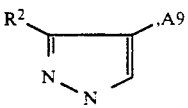 A9

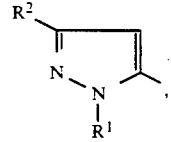 A10

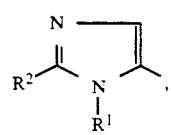 A11

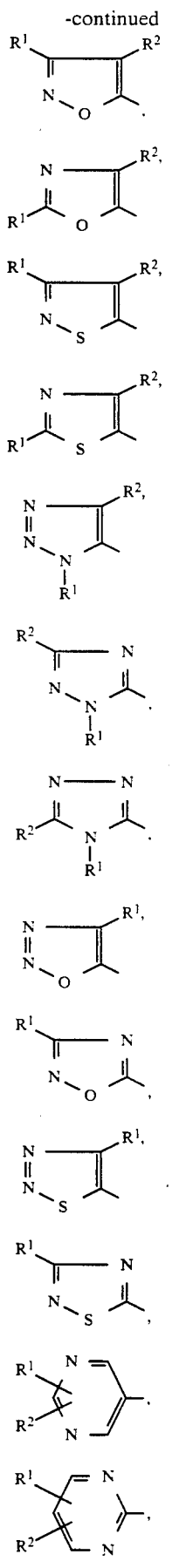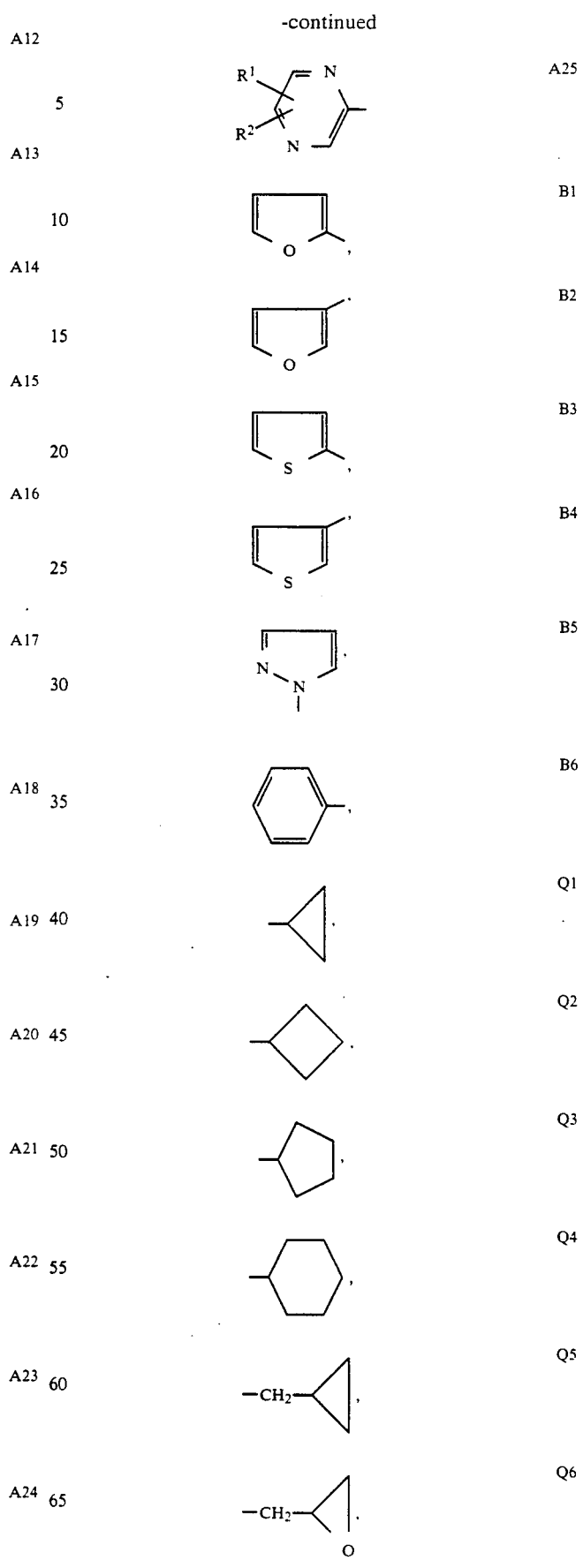

-continued
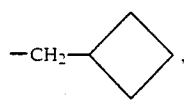 Q7
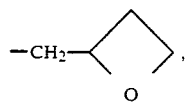 Q8
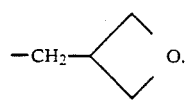 Q9
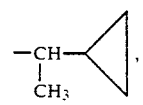 Q10
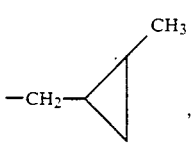 Q11
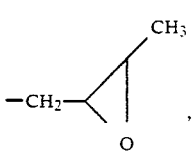 Q12
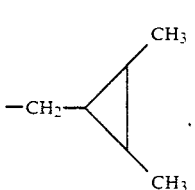 Q13
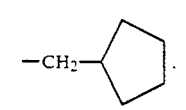 Q14
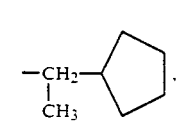 Q15
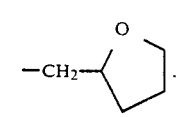 Q16
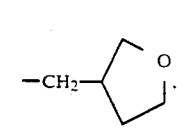 Q17
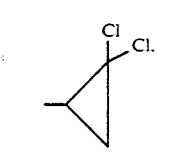 Q18
-continued
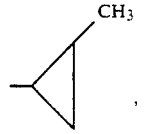 Q19
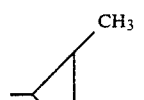 Q20
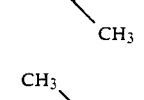 Q21
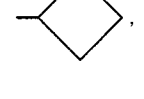 Q22
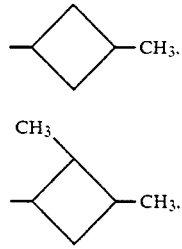 Q23
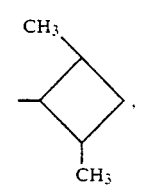 Q24
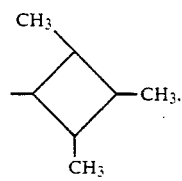 Q25
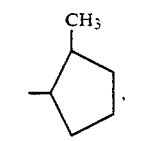 Q26
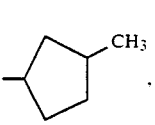 Q27
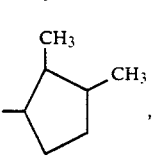 Q28
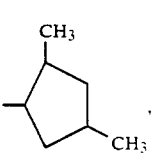 Q29

-continued
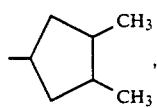 Q30
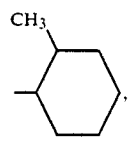 Q31
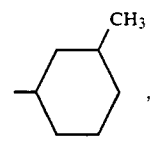 Q32
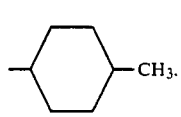 Q33
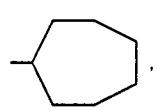 Q34
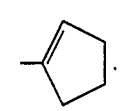 Q35
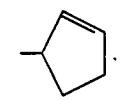 Q36
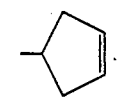 Q37
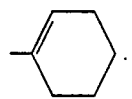 Q38
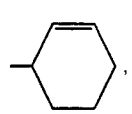 Q39
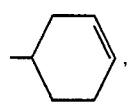 Q40
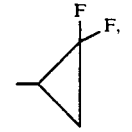 Q41
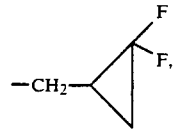 Q42
-continued
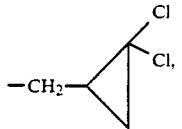 Q43
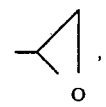 Q44
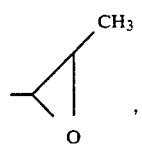 Q45
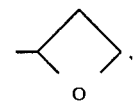 Q46
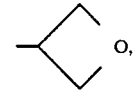 Q47
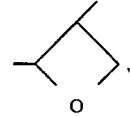 Q48
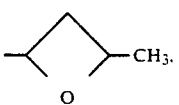 Q49
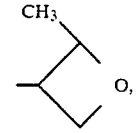 Q50
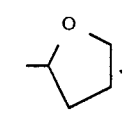 Q51
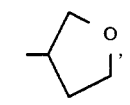 Q52
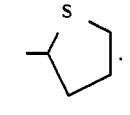 Q53
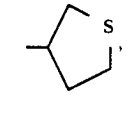 Q54
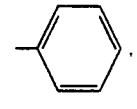 Q55

-continued

—CH(CH₃)COOCH₃,

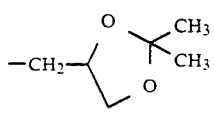

Q56  wherein R¹ and R² of the above formulas represent the same meaning as the aforementioned ones.
Q57  Further, the physical data are shown in Table 5.

TABLE 5

| Compound No. | Solvent | ¹H-NMR δ ppm (Reference substance TMS) | Melting point (°C.) |
|---|---|---|---|
| 13 | CDCl₃ + DMSO d-6 | 5.96(d, 1H, J=8.4Hz), 6.88~8.10(m, 9H), 9.25(d, 1H, J=8.4Hz) | 210~215 |
| 25 | CDCl₃ + DMSO d-6 | 5.41(brs, 2H), 5.83(d, 1H, J=8.4Hz), 6.12~6.45(m, 2H), 7.16~7.55(m, 2H), 7.96~8.44(m, 2H), 8.44~8.70(m, 1H), 8.87(d, 1H, J=8.4Hz), 8.87~9.10(m, 1H) | 169~172 |
| 26 | CDCl₃ + DMSO d-6 | 5.53(brs, 2H), 5.81(d, 1H, J=8.4Hz), 6.55(s, 1H), 7.26~7.70(m, 3H), 8.15~9.53(m, 5H) | 208~209 |
| 27 | CDCl₃ + DMSO d-6 | 5.51(brs, 2H), 5.99(d, 1H, J=8.4Hz), 6.63~7.53(m, 4H), 7.90~8.46(m, 2H), 8.46~8.71(m, 1H), 8.77~9.11(m, 1H), 8.99(d, 1H, J=8.4Hz) | 177~180 (decomposed) |
| 100 | CDCl₃ + DMSO d-6 | 2.35(s, 3H), 3.75(S, 3H), 5.30(brs, 2H), 5.90(d, 1H, J=8.4Hz), 6.70~7.29(m, 3H), 7.89(s, 1H), 7.99(d, 1H, J=8.4Hz), 9.06(brs, 1H) | 184~189 (decomposed) |
| 101 | CDCl₃ + DMSO d-6 | 2.35(s, 3H), 3.73(s, 3H), 5.34(brs, 2H), 5.77(d, 1H, J=8.4Hz), 6.91~7.37 (m, 3H), 7.94(s, 1H), 7.97(d, 1H, J=8.4Hz), 8.27(brs, 1H) | 173~177 (decomp.) |
| 104 | CDCl₃ + DMSO d-6 | 1.19(s, 6H), 2.32(s, 3H), 3.72(s, 3H) 4.83~5.81(m, 2H), 5.29(brs, 2H), 7.59(d, 1H, J=7.2Hz), 7.87(s, 1H) 7.91(brs, 1H) | 160~164 (decomposed) |
| 156 | CDCl₃ + DMSO d-6 | 2.17(s, 3H), 3.98(s, 3H), 5.23(brs, 2H), 5.79(d, 1H, J=8.4Hz), 6.10~6.37 (m, 2H), 6.46(s, 1H), 7.09~7.43(m, 1H), 8.21(d, 1H, J=8.4Hz), 8.97(brs, 1H) | 159~162 |
| 157 | CDCl₃ + DMSO d-6 | 2.22(s, 3H), 4.04(s, 3H), 5.45 (brs, 2H), 5.73(d, 1H, J=8.4Hz) 6.45~6.70(m, 1H), 6.68(S, 1H) 7.35~7.70(m, 2H), 8.55((d, 1H, J=8.4Hz) 9.10(brs, 1H) | 139~141 |
| 158 | CDCl₃ + DMSO d-6 | 2.15(s, 3H), 3.95(s, 3H), 5.38(brs, 2H), 5.86(d, 1H, J=8.4Hz), 6.48(s, 1H), 6.64~7.28(m, 3H), 8.47((d, 1H, J=8.4Hz), 9.08(brs, 1H) | 168~170 |
| 159 | CDCl₃ + DMSO d-6 | 2.24(s, 3H), 4.10(s, 3H), 5.06~5.46 (m, 2H), 5.94(d, 1H, J=8.4Hz), 6.62(s, 1H), 7.11~7.51(m, 3H), 8.37(d, 1H, J=8.4Hz), 9.26(brs, 1H) | 176~178 |
| 173 | CDCl₃ + DMSO d-6 | 1.33(t, 3H, J=6.60Hz), 2.21(S, 3H) 4.45(q, 2H, J=6.60Hz), 5.50(brs, 2H) 5.80(d, 1H, J=9.00Hz), 6.25~6.50 (m, 2H), 6.68(S, 1H), 7.45~7.60(m, 1H), 8.71(d, 1H, J=9.00Hz), 9.38(brs, 1H) | 164~166 |
| 175 | CDCl₃ + DMSO d-6 | 1.33(t, 3H, J=7.20Hz), 2.21(S, 3H) 4.46(q, 2H, J=7.20Hz), 5.60(brs, 2H) 5.97(d, 1H, J=9.00Hz), 6.68(s, 1H) 6.80~7.50(m, 3H), 8.83(d, 1H, J=9.00Hz), 9.47(brs, 1H) | 177~179 |
| 176 | CDCl₃ + DMSO d-6 | 1.30(t, 3H, J=7.20Hz), 2.15(S, 3H) 4.38(q, 2H, J=7.20Hz), 5.38(brs, 2H) 5.71(d, 1H, J=9.00Hz), 6.54(s, 1H) 6.80~7.30(m, 4H), 8.42(d, 1H, J=9.00Hz) | 174~177 |
| 179 | CDCl₃ + DMSO d-6 | 1.42(d, 6H, J=6.60Hz), 2.23(S, 3H) 5.24(bs, 2H), 5.35(qq, 1H, J=6.60Hz), 5.76(d, 1H, J=8.40Hz), 6.15~6.35 (m, 2H), 6.41(S, 1H), 7.15~7.35(m, 1H), 8.00~8.50(m, 2H) | 165~166 |
| 180 | CDCl₃ + DMSO d-6 | 1.42(d, 6H, J=6.60Hz), 2.24(S, 3H) 5.45(brs, 2H), 5.45(qq, 1H, J=6.60Hz), 5.74(d, 1H, J=8.40Hz), 6.45~6.60 (m, 1H), 6.61(S, 1H), 7.45~7.70(m, 2H), 8.47(d, 1H, J=8.40Hz), 9.40(brs, 1H) | 171~173 |
| 181 | CDCl₃ | 1.43(d, 6H, J=6.60Hz), 2.26(S, 3H) | 190~192 |

TABLE 5-continued

| Compound No. | Solvent | $^1$H-NMR δ ppm (Reference substance TMS) | Melting point (°C.) |
|---|---|---|---|
| | + DMSO d-6 | 5.53(brs, 2H), 5.45(qq, 1H, J=6.60Hz), 6.03(d, 1H, J=8.40Hz), 6.61(s, 1H) 6.90~7.50(m, 3H). 8.74(d, 1H, J=8.40Hz), 9.40(brs, 1H) | |
| 182 | CDCl$_3$ + DMSO d-6 | 1.50(d, 6H, J=6.60Hz), 2.23(S, 3H) 5.55(brs, 2H), 5.50(qq, 1H, J=6.60Hz), 5.87(d, 1H, J=9.00Hz), 6.66(s, 1H) 7.10~7.55(m, 3H), 8.71(d, 1H, J=9.00Hz), 9.47(brs, 1H) | 208~209 |
| 306 | CDCl$_3$ + DMSO d-6 | 1.36~2.83(m, 6H), 2.19(s, 3H), 5.38(brs, 2H), 5.51(quint, 1H, J=8.4Hz), 5.71(d, 1H, J=9.0Hz), 6.05~6.35(m, 2H), 6.50(s, 1H), 7.22~7.40(m, 1H), 8.45(d, 1H, J=9.0Hz), 9.07(brs, 1H) | 179~180 |
| 311 | CDCl$_3$ + DMSO d-6 | 1.35~2.82(m, 6H), 2.17(s, 3H), 5.40(brs, 2H), 5.47(quint, 1H, J=8.4Hz), 5.61(d, 1H, J=8.4Hz), 6.30~6.48(m, 1H), 6.53(s, 1H), 7.26~7.60(m, 2H), 8.40(d, 1H, J=8.4Hz), 9.10(brs, 1H) | 178~183 (decomposed) |
| 316 | CDCl$_3$ + DMSO d-6 | 1.45~2.90(m, 6H), 2.21(s, 3H). 5.40(brs, 2H), 5.50(quint, 1H, J=8.4Hz), 5.80(d, 1H, J=9.0Hz), 6.47(s, 1H). 6.71~7.00(m, 2H), 7.02~7.26(m, 1H), 8.50(d, 1H, J=9.0Hz), 9.10(brs, 1H) | 192~196 (decomposed) |
| 317 | CDCl$_3$ + DMSO d-6 | 1.33~2.35(m, 8H), 2.16(s, 3H). 5.50(brs, 2H). 5.10~5.65(m, 1H). 5.79(d, 1H, J=7.8Hz), 6.50(s, 1H), 6.70~7.08(m, 2H), 7.10~7.28(m, 1H), 8.58(d, 1H, J=7.8Hz), 9.11(brs, 1H) | 194~201 (decomposed) |
| 321 | CDCl$_3$ + DMSO d-6 | 1.37~2.96(m, 6H), 2.19(s, 3H). 5.33(brs, 2H), 5.51(quint, 1H, J=8.4Hz), 5.71(d, 1H, J=9.0Hz), 6.45(s, 1H), 6.85~7.33(m, 3H), 8.34(d, 1H, J=9.0Hz), 9.08(brs, 1H) | 193~194 |
| 343 | CDCl$_3$ + DMSO d-6 | 0.80(t, 3H, J=6.6Hz), 1.37(d, 3H, J=6.6Hz), 1.48~2.00(m, 2H), 2.19(s, 3H), 5.13(qt, J=6.6Hz), 5.47(brs, 2H), 5.85(d, 1H, J=9.0Hz), 6.46(s, 1H), 6.70~7.30(m, 3H), 8.55(d, 1H, J=9.0Hz), 9.22(brs, 1H) | 169~173 |
| 439 | CDCl$_3$ + DMSO d-6 | 5.32(bs, 2H), 6.11(d, 2H, J=52.8Hz), 6.10~6.30(m, 1H), 6.70(d, 2H, J=9.0Hz), 7.40~7.55(m, 1H), 7.75~7.90(m, 1H), 7.95~8.25(m, 1H), 8.40~8.70(m, 1H), 9.33(d, 1H, J=9.0Hz), 9.55(bs, 1H) | 113~116 |
| 448 | CDCl$_3$ + DMSO d-6 | 1.40(d, 6H, J=6.6Hz), 5.45(qq, 1H, J=6.6Hz), 5.60(brs, 2H), 5.85~6.15(m, 2H), 6.80~7.60(m, 4H), 8.70(d, 1H, J=8.4Hz), 8.92(brs, 1H) | 133~135 |
| 1007 | CDCl$_3$ + DMSO d-6 | 0.20~0.60(m, 4H), 0.95~1.55(m, 1H), 2.20(s, 3H), 4.24(d, 2H, J=7.8Hz), 5.37(brs, 2H), 5.91(d, 1H, J=9.0Hz), 6.49(s, 1H), 6.72~7.25(m, 3H), 8.48(d, 1H, J=9.0Hz), 8.55(brs, 1H) | 177~180 |
| 1013 | CDCl$_3$ + DMSO d-6 | 0.83(d, 3H, J=6.6Hz), 2.17(s, 3H), 1.75~2.35(m, 1H), 4.22(d, 2H, J=7.8Hz), 5.39(brs, 2H), 5.91(d, 1H, J=9.0Hz), 6.50(s, 1H), 6.70~7.25(m, 3H), 8.45(d, 1H, J=9.0Hz), 8.60(brs, 1H) | 190~193 |
| 1023 | CDCl$_3$ + DMSO d-6 | 2.23(s, 3H), 4.11(s, 3H), 6.18(s, 1H), 6.68(s, 1H). 6.88~7.48(m, 5H) | — |
| 1024 | CDCl$_3$ + DMSO d-6 | 2.26(s, 3H), 4.15(s, 3H), 5.93(s, 1H), 6.68(s, 1H), 7.07~7.53(m, 5H) | 144~145 |
| 1028 | CDCl$_3$ | 2.25(s, 3H), 4.10(s, 3H), 6.64(s, 1H), 7.05~7.70(m, 3H) 8.18~8.32(m, 1H), 9.25(brs, 1H) | — |
| 1033 | CDCl$_3$ | 2.22(s, 3H), 3.83(s, 3H), 4.03(s, 3H), 4.82(brs, 2H), 5.76(d, 1H, J=7.2Hz), 6.39(s, 1H), 7.07~7.67(m, 4H) | — |
| 1034 | CDCl$_3$ + DMSO d-6 | 2.23(s, 3H), 4.07(S, 3H), 4.40(d, 2H, J=6.0Hz), 4.97~6.02(m, 4H), 5.62(brs, 2H), 6.67(S, 1H), 7.07~7.52(m, 3H), 7.99(d, 1H, J=8.4Hz) | — |
| 1035 | CDCl$_3$ | 0.70~1.90(m, 9H), 2.21(s, 3H), 4.02(s, 3H), 4.73(brs, 2H), 5.72(d, 1H, J=7.2Hz), 6.35(s, 1H), 7.03~7.68(m, 4H) | — |
| 1037 | CDCl$_3$ | 2.17(s, 3H), 3.96(s, 3H), | 187~189 |

TABLE 5-continued

| Compound No. | Solvent | $^1$H-NMR δ ppm (Reference substance TMS) | Melting point (°C.) |
|---|---|---|---|
| 1038 | CDCl$_3$ | 5.88(d, 1H, J=9.0Hz), 6.54(brs, 2H), 6.61(s, 1H), 7.00~7.55(m, 6H), 7.85~8.15(m, 2H), 8.57(d, 1H, J=9.0Hz) | 102~104 |
| 1039 | CDCl$_3$ | 2.23(s, 3H), 2.80(d, 3H, J=4.8Hz), 4.08(s, 3H), 5.63~6.58(m, 3H), 6.59(s, 1H), 6.35~6.80(brs, 1H), 7.05~7.45(m, 3H), 7.80(d, 1H, J=9.0Hz) | — |
| 1040 | CDCl$_3$ + DMSO d-6 | 1.14(d, 6H, J=7.2Hz), 2.20(s, 3H), 4.03(s, 3H), 5.60~6.10(m, 3H), 6.38(d, 1H, J=7.8Hz), 6.58(s, 1H), 6.98~7.48(m, 4H), 7.85(d, 1H, J=9.6Hz) | 185~188 |
| 1041 | CDCl$_3$ + DMSO d-6 | 2.25(s, 3H), 4.10(S, 3H), 6.06(d, 1H, J=8.0Hz), 6.31(brs, 2H), 6.71(s, 1H), 6.96~7.71(m, 8H), 8.66(d, 1H, J=8.0Hz), 8.98(s, 1H) | 181~185 |
| | | 2.25(s, 3H), 4.10(s, 3H), 6.09(d, 1H, J=9.6Hz), 6.73(brs, 2H), 6.92(s, 1H), 7.18~7.85(m, 7H), 9.00(d, 1H, J=9.6Hz) | |
| 1042 | CDCl$_3$ | 2.20(s, 3H), 3.12(s, 3H), 4.04(s, 3H), 5.93(brs, 2H), 6.54(s, 1H), 7.04~7.77(m, 6H) | 101~103 |
| 1043 | CDCl$_3$ + DMSO d-6 | 1.31(t, 3H, J=6.6Hz), 2.22(s, 3H), 4.06(s, 3H), 4.24(q, 2H, J=6.6Hz), 5.92(d, 1H, J=9.6Hz), 6.46(brs, 2H), 6.72(s, 1H), 7.23~7.68(m, 3H), 8.69(d, 1H, J=9.6Hz) | — |
| 1539 | CDCl$_3$ + DMSO d-6 | 1.80~2.72(m, 4H), 2.16(s, 3H), 5.28~6.34(m, 6H), 6.51(s, 1H), 6.65~7.03(m, 2H), 7.08~7.26(m, 1H), 8.57(d, 1H, J=9.0Hz), 9.18(brs, 1H) | 187~188 |

The intermediates obtained during the course of the production of the compounds of the present invention are novel compounds. Thus the present invention further involves these compounds.

Accordingly, the present invention provides a compound represented by the general formula:

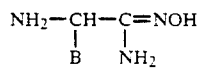

wherein B represents a thienyl or a furyl group; and a salt thereof as well as a compound represented by the general formula:

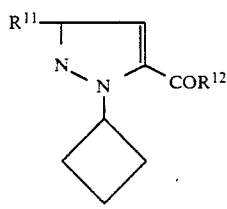

wherein R$^{11}$ represents a hydrogen atom or an alkyl group having 1 to 4 carbon atoms, and R$^{12}$ represents hydroxyl or an alkoxy group having 1 to 8 carbon atoms or a halogen group.

The present invention further provides a fungicide containing an oxime derivative represented by the above general formula [I] as an active ingredient.

The fungicide of the present invention is effective not only on downy mildew and phytophthora rot of various crops but also on other diseases. Examples of major plant diseases include cucumber downy mildew, grape downy mildew, lettuce downy mildew, Chinese cabbage downy mildew, hop downy mildew, potato phytophthora rot, tomato phytophthora rot, cucumber gray phytophthora rot, green pepper phytophthora rot, damping-off of tomato, cucumber and rice caused by Pythium, and beat damping off caused by Aphanomyces.

The fungicide of the present invention may be applied by, for example, seed treatment, foliage application or soil application. The dose and concentration thereof may vary depending on the crop, the disease and its degree and the application method. Generally speaking, it may be applied at a ratio of 2 to 2000 g per ha, preferably 10 to 1000 g per ha, in terms of the active ingredient.

The concentration at the application may range from 1 to 1000 ppm, preferably from 5 to 500 ppm.

Since the agrohorticultural fungicide of the present invention exerts both of preventive and therapeutic effects, it may be applied over a wide range of time. Namely, it may be applied either before or after the occurrence of a disease.

It is needless to say that the fungicide of the present invention may be used together with various other biologically active compounds, for example, agricultural chemicals such as similar or supplementative fungicides, insecticides, herbicides and plant growth regulators, fertilizers and soil conditioners. Furthermore, the fungicide may be formulated into a product together with these materials.

The fungicide of the present invention may be mixed with an appropriate carrier, for example, a solid carrier such as clay, talc, bentonite or diatomaceous earth; or a liquid one such as water, an alcohol such as methanol or ethanol, an aromatic hydrocarbon such as benzene, toluene or xylene, a chlorinated hydrocarbon, an ether, a ketone, an ester such as ethyl acetate or an acid amide such as dimethylformamide. Further, various additives such as emulsifiers, dispersants, suspending agents, penetrating agent spreaders or stabilizers may be added thereto if desired. Thus the fungicide of the present invention may be formulated into any desirable form such as emulsion, oil, wettable powder, dust, granules or flowable.

Now examples of the compositions of these formulations will be given, though the present invention is not restricted thereby. In the following compositions, all parts are by weight.

| (1) Wettable powder | |
| --- | --- |
| compound of the invention | 5 to 75 parts |
| solid carrier | 9 to 86 parts |
| surfactant | 5 to 10 parts |
| other components | 0 to 5 parts |

Examples of the solid carrier include calcium carbonate, kaolinite, Zeeklite A, Zeeklite PEP, diatomaceous earth and talc. Examples of the surfactant include Lunox 1000C, Solpol 5039, Solpol 5050, Solpol 005D, Solpol 5029-0, calcium sulfonate and sodium dodecylsulfonate.

An example of other components is Carplex #80.

| (2) Emulsion | |
| --- | --- |
| compound of the invention | 5 to 50 parts |
| liquid carrier | 35 to 90 parts |
| surfactant | 5 to 15 parts |

Examples of the liquid carrier include xylene, dimethylformamide, methylnaphthalene and isophorone.

Examples of the surfactant include Solpol 2680, Solpol 3005X and Solpol 3346.

| (3) Flowable | |
| --- | --- |
| compound of the invention | 5 to 75 parts |
| liquid carrier | 14.5 to 68 parts |
| surfactant | 5 to 10 parts |
| other components | 1 to 10 parts |

Water is used as the liquid carrier.

Examples of the surfactant include Lunox 1000C, Solpol 3353, Solpol FL, Nippol, Agrisol S-710 and sodium ligninsulfonate.

Examples of other components include ethylene glycol, propylene glycol and xanthan gum.

| (4) Dust | |
| --- | --- |
| compound of the invention | 0.03 to 20 parts |
| solid carrier | 94 to 98.97 parts |
| other components | 0 to 3 parts |

Examples of the solid carrier include calcium carbonate, kaolinite, Zeeklite and talc.

Examples of other components include diisopropyl phosphate and Carplex #80.

| (5) Granules | |
| --- | --- |
| compound of the invention | 0.3 to 10 parts |
| solid carrier | 92 to 98.7 parts |
| other components | 0 to 5 parts |

Examples of the solid carrier include calcium carbonate, kaolinite, bentonite and talc.

Examples of other components include calcium ligninsulfonate and polyvinyl alcohol.

Now, particular examples of the formulation of the fungicide of the present invention containing the oxime derivative of the present invention represented by the general formula [1] as an active ingredient will be given, though the present invention is not restricted thereby. In the following composition, all parts are by weight.

FORMULATION EXAMPLE 1

| Wettable powder | |
| --- | --- |
| compound of the invention | 5 parts |
| Zeeklite PFP | 87 parts |
| (mixture of kaolinite and sericite; mfd. by Zeeklite Kogyo) | |
| Solpol 5039 | 5 parts |
| (mixture of anionic surfactant and white carbon; mfd. by Toho Chemical Industry Co., Ltd.) | |
| Carplex #80 | 3 parts |
| (white carbon; mfd. by Shionogi & Co., Ltd.) | |

The above components were homogeneously mixed together and ground to thereby give a wettable powder. At the use, the product was diluted 100 to 10,000-fold and applied in such a manner as to give a dose of the active ingredient of 10 to 1000 g/ha.

FORMULATION EXAMPLE 2

| Wettable powder | |
| --- | --- |
| compound of the invention | 25 parts |
| Zeeklite PFP | 69 parts |
| (mixture of kaolinite and sericite; mfd. by Zeeklite Kogyo) | |
| Solpol 5039 | 3 parts |
| (mixture of anionic surfactant and white carbon; mfd. by Toho Chemical Industry Co., Ltd.) | |
| Carplex #80 | 3 parts |
| (white carbon; mfd. by Shionogi & Co., Ltd.) | |

The above components were homogeneously mixed together and ground to thereby give a wettable powder. At the use, the product was diluted 500 to 50,000-fold and applied in such a manner as to give a dose of the active ingredient of 10 to 1000 g/ha.

FORMULATION EXAMPLE 3

| Wettable powder | |
| --- | --- |
| compound of the invention | 20 parts |
| calcium carbonate (powder) | 69 parts |
| Solpol 5050 | 10 parts |
| (mixture of anionic surfactant and white carbon; mfd. by Toho Chemical Industry Co., Ltd.) | |
| Carplex #80 | 1 parts |
| (white carbon; mfd. by Shionogi & Co., Ltd.) | |

The above components were homogeneously mixed together and ground to thereby give a wettable powder. At the use, the product was diluted 400 to 40,000-fold and applied in such a manner as to give a dose of the active ingredient of 10 to 1000 g/ha.

FORMULATION EXAMPLE 4

| Emulsion | |
|---|---|
| compound of the invention | 5 parts |
| xylene | 70 parts |
| N,N-dimethylformamide | 20 parts |
| Solpol 2680 | 5 parts |
| (mixture of nonionic surfactant and anionic surfactant; mfd. by Toho Chemical Industry Co., Ltd.) | |

The above components were homogeneously mixed together to thereby give an emulsion. At the use, the product was diluted 100 to 10,000-fold and applied in such a manner as to give a dose of the active ingredient of 10 to 1000 g/ha.

FORMULATION EXAMPLE 5

| Emulsion | |
|---|---|
| compound of the invention | 50 parts |
| xylene | 25 parts |
| N,N-dimethylformamide | 10 parts |
| Solpol 3346 | 15 parts |
| (mixture of nonionic surfactant and anionic surfactant; mfd. by Toho Chemical Industry Co., Ltd.) | |

The above components were homogeneously mixed together to thereby give an emulsion. At the use, the product was diluted 500 to 50,000-fold and applied in such a manner as to give a dose of the active ingredient of 10 to 1000 g/ha.

FORMULATION EXAMPLE 6

| Flowable | |
|---|---|
| compound of the invention | 5 parts |
| Solpol 3353 | 5 parts |
| (nonionic surfactant; mfd. by Toho Chemical Industry Co., Ltd.) | |
| Lunox 1000C | 3 parts |
| (anionic surfactant; mfd. by Toho Chemical Industry Co., Ltd.) | |
| 1% aqueous solution of xanthan gum (natural polymer) | 20 parts |
| water | 57 parts |
| ethylene glycol | 10 parts |

The above components other than the active ingredient, i.e., the compound of the invention, were homogeneously dissolved. Then the compound of the invention was added thereto and the mixture was thoroughly stirred and wet-ground with a sand mill to thereby give a flowable. At the use, the product was diluted 100 to 10,000-fold and applied in such a manner as to give a dose of the active ingredient of 10 to 1000 g/ha.

FORMULATION EXAMPLE 7

| Flowable | |
|---|---|
| compound of the invention | 75 parts |
| Solpol 3353 | 5 parts |
| (nonionic surfactant; mfd. by Toho Chemical Industry Co., Ltd.) | |
| Lunox 1000C | 0.5 parts |
| (anionic surfactant; mfd. by Toho Chemical Lndustry Co., Ltd.) | |
| 1% aqueous solution of xanthan gum (natural polymer) | 10 parts |
| water | 4.5 parts |
| propylene glycol | 5 parts |

The above components other than the active ingredient, i.e., the compound of the invention, were homogeneously dissolved. Then the compound of the invention was added thereto and the mixture was thoroughly stirred and wet-ground with a sand mill to thereby give a flowable. At the use, the product was diluted 1500 to 150,000-fold and applied in such a manner as to give a dose of the active ingredient of 10 to 1000 g/ha.

FORMULATION EXAMPLE 8

| Dust | |
|---|---|
| compound of the invention | 10 parts |
| clay | 90 parts |

The above components were homogeneously mixed together to thereby give a dust. At the use, the product was applied as such to thereby give a dose of the active ingredient of 10 to 1000 g/ha.

FORMULATION EXAMPLE 9

| Granules | |
|---|---|
| compound of the invention | 5 parts |
| bentonite | 25 parts |
| talc | 70 parts |

The above components were homogeneously mixed together and ground. Then a small amount of water was added thereto and the mixture was stirred and granulated with an extruder. After drying, granules were obtained.

At the use, the product was applied as such so as to give a dose of the active ingredient of 10 to 1000 g/ha.

To illustrate the effects of the compounds of the present invention examined by biological tests, the following Test Examples will be given.

TEST EXAMPLE 1

Preventive effect on cucumber downy mildew

Cucumber seedlings (variety: Sagami Hanpaku were grown in pots of 7 cm in diameter. When these seedlings grew into the mono- or difoliate stage, an emulsion of a test compound, which had been prepared according to the method described in Formulation Example 4 or 5 and diluted with water at a concentration of 500 ppm was sprayed with a spray gun in a dose of 20 ml/pot. On the next day of the application, a spore suspension ($2 \times 10^5$/ml) of *Pseudoperonospora cubensis* was sprayed to the seedlings, which were then stored in an inoculation box at 25° C. at a humidity of at least 95% over day and night. Next, these seedlings were placed in a greenhouse. Seven days after the inoculation, the ratio of lesions thus formed on the inoculated leaves was determined and the preventive value was calculated according to the following equation:

$$\text{preventive value} = \left(1 - \frac{\text{lesion area ratio in test lot}}{\text{lesion area ratio in control lot}}\right) \times 100$$

The following Table 6 shows the results.

TABLE 6

(Application conc.: 500 ppm)

| Cpd. No. | Preventive value | Chemical damage |
| --- | --- | --- |
| 25 | 100 | none |
| 26 | 100 | do. |
| 27 | 100 | do. |
| 100 | 100 | do. |
| 101 | 100 | do. |
| 104 | 100 | do. |
| 156 | 100 | do. |
| 157 | 100 | do. |
| 158 | 100 | do. |
| 159 | 100 | do. |
| 173 | 100 | do. |
| 175 | 100 | do. |
| 176 | 100 | do. |
| 179 | 100 | do. |
| 180 | 100 | do. |
| 181 | 100 | do. |
| 182 | 100 | do. |
| 306 | 100 | do. |
| 311 | 100 | do. |
| 316 | 100 | do. |
| 317 | 100 | do. |
| 321 | 100 | do. |
| 343 | 100 | do. |
| 439 | 100 | do. |
| 1007 | 100 | do. |
| 1013 | 100 | do. |
| 1023 | 100 | do. |
| 1024 | 100 | do. |
| 1028 | 100 | do. |
| 1033 | 100 | do. |
| 1037 | 100 | do. |
| 1042 | 100 | do. |
| 1043 | 100 | do. |
| 1539 | 100 | do. |

TEST EXAMPLE 2

Therapeutic effect on cucumber downy mildew

Cucumber seedlings (variety: Sagami Hanpaku) were grown in pots of 7 cm in diameter. When these seedlings grew into the mono- or difoliate stage, a spore suspension ($2 \times 10^5$/ml) of Pseudoperonospora cubensis was sprayed to the seedlings, which were then stored in an inoculation box at 25° C at a humidity of at least 95% over day and night. On the next day, an emulsion of a test compound, which had been prepared according to the method described in Formulation Example 4 or 5 and diluted with water to a concentration of 500 ppm, was sprayed with a spray gun in a dose of 20 ml/pot. Next, these seedlings were placed in a greenhouse. Seven days after the inoculation, the ratio of lesions thus formed on the inoculated leaves was determined and the preventive value was calculated according to the following equation:

$$\text{preventive value} = \left(1 - \frac{\text{lesion area ratio in test lot}}{\text{lesion area ratio in control lot}}\right) \times 100$$

The following Table 7 shows the results.

TABLE 7

(Application conc.: 500 ppm)

| Cpd. No. | Preventive value | Chemical damage |
| --- | --- | --- |
| 25 | 100 | none |
| 26 | 100 | do. |
| 27 | 100 | do. |
| 100 | 100 | do. |
| 101 | 100 | do. |
| 104 | 100 | do. |
| 156 | 100 | do. |
| 157 | 100 | do. |
| 158 | 100 | do. |
| 159 | 100 | do. |
| 173 | 100 | do. |
| 175 | 100 | do. |
| 176 | 100 | do. |
| 179 | 100 | do. |
| 180 | 100 | do. |
| 181 | 100 | do. |
| 182 | 100 | do. |
| 306 | 100 | do. |
| 311 | 100 | do. |
| 316 | 100 | do. |
| 317 | 100 | do. |
| 321 | 100 | do. |
| 439 | 100 | do. |
| 1007 | 100 | do. |
| 1013 | 100 | do. |
| 1023 | 100 | do. |
| 1024 | 100 | do. |
| 1033 | 100 | do. |
| 1037 | 100 | do. |
| 1042 | 100 | do. |
| 1043 | 100 | do. |
| 1539 | 100 | do. |

TEST EXAMPLE 3

Preventive effect on tomato phytophthora rot

Tomato seedlings (variety: Fukuju) were grown in pots of 8 cm in diameter. When these seedlings grew into the trifoliate stage, a wettable powder, which had been prepared according to the method described in Formulation Examples 1 to 3 and diluted with water to a given concentration of the active ingredient was sprayed with a spray gun in a dose of 20 ml/pot. On the next day of the application, a spore suspension ($2 \times 10^5$/ml) of Phytophthora infestans was sprayed to the seedlings, which were then stored in an inoculation box at 20° C. at a humidity of at least 95% for five days. Then the ratio of lesions thus formed on the inoculated leaves was determined and the preventive value was calculated according to the following equation:

$$\text{preventive value} = \left(1 - \frac{\text{lesion area ratio in test lot}}{\text{lesion area ratio in control lot}}\right) \times 100$$

The following Table 8 shows the results.

TABLE 8

| | (Application conc.: 500 ppm) | |
|---|---|---|
| Cpd. No. | Preventive value | Chemical damage |
| 25 | 100 | none |
| 26 | 100 | do. |
| 27 | 100 | do. |
| 100 | 100 | do. |
| 101 | 100 | do. |
| 104 | 100 | do. |
| 156 | 100 | do. |
| 157 | 100 | do. |
| 158 | 100 | do. |
| 159 | 100 | do. |
| 173 | 100 | do. |
| 175 | 100 | do. |
| 176 | 100 | do. |
| 179 | 100 | do. |
| 180 | 100 | do. |
| 181 | 100 | do. |
| 182 | 100 | do. |
| 306 | 100 | do. |
| 311 | 100 | do. |
| 316 | 100 | do. |
| 317 | 100 | do. |
| 321 | 100 | do. |
| 439 | 100 | do. |
| 1007 | 100 | do. |
| 1013 | 100 | do. |
| 1023 | 100 | do. |
| 1024 | 100 | do. |
| 1037 | 100 | do. |
| 1042 | 100 | do. |
| 1043 | 100 | do. |
| 1539 | 100 | do. |

TEST EXAMPLE 4

Therapeutic effect on tomato phytophthora rot

Tomato seedlings (variety: Fukuju) were grown in pots of 8 cm in diameter. When these seedlings grew into the trifoliate stage, a spore suspension ($2 \times 10^5$/ml) of *Phytophthora infestans* was sprayed to the seedlings, which were then stored in an inoculation box at 20° C. at a humidity of at least 95% over day and night. On the next day, a wettable powder, which had been prepared according to the method described in Formulation Examples 1 to 3 and diluted with water to a given concentration of the active ingredient, was sprayed with a spray gun in a dose of 20 ml/pot. After air-drying, these seedlings were placed in the above inoculation box. After five days, the ratio of lesions thus formed on the inoculated leaves was determined and the preventive value was calculated according to the following equation:

$$\text{preventive value} = \left(1 - \frac{\text{lesion area ratio in test lot}}{\text{lesion area ratio in control lot}}\right) \times 100$$

The following Table 9 shows the results.

TABLE 9

| | (Application conc.: 500 ppm) | |
|---|---|---|
| Cpd. No. | Preventive value | Chemical damage |
| 25 | 100 | none |
| 26 | 100 | do. |
| 27 | 100 | do. |
| 100 | 100 | do. |
| 101 | 100 | do. |
| 104 | 100 | do. |
| 156 | 100 | do. |
| 157 | 100 | do. |
| 158 | 100 | do. |
| 159 | 100 | do. |
| 173 | 100 | do. |
| 175 | 100 | do. |
| 176 | 100 | do. |
| 179 | 100 | do. |
| 180 | 100 | do. |
| 181 | 100 | do. |
| 182 | 100 | do. |
| 306 | 100 | do. |
| 311 | 100 | do. |
| 316 | 100 | do. |
| 317 | 100 | do. |
| 321 | 100 | do. |
| 439 | 100 | do. |
| 1013 | 100 | do. |
| 1023 | 100 | do. |
| 1024 | 100 | do. |
| 1028 | 100 | do. |
| 1037 | 100 | do. |
| 1042 | 100 | do. |
| 1043 | 100 | do. |
| 1539 | 100 | do. |

We claim:

1. An oxime derivative represented by the general formula (I):

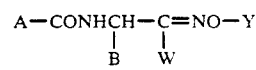

wherein:
A represents an optionally substituted pyrazolyl group,
B represents an optionally substituted furyl group, an unsubstituted or substituted thienyl group, an unsubstituted or substituted phenyl group, an unsubstituted or substituted pyrazolyl group, an alkenyl group having 2 to 10 carbon atoms, a halogenated alkenyl group having 2 to 10 carbon atoms, an alkoxy group having 1 to 10 carbon atoms, an alkenyloxy group having 2 to 10 carbon atoms, an alkynyloxy group having 2 to 10 carbon atoms or an alkylthio group having 1 to 10 carbon atoms,
Y represents a hydrogen atom, and
W represents a hydrogen atom, a halogenated atom, an unsubstituted or substituted phenylamino group, an amino group or an alkylamino group, or an optically active isomer thereof.

2. A derivative as claimed in claim 1, selected from among the following ones:

(1) α-(1-cyclobutyl-3-methylpyrazole-5-yl-carbonylamino)(2-thienyl)acetoamidoxime

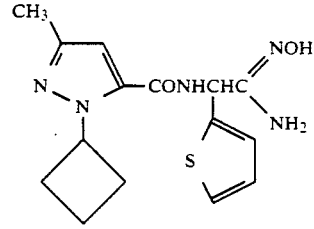

(2) α-(1-cyclobutyl-3-methylpyrazole-5-yl-carbonylamino)(3-furyl)acetoamidoxime (3) α-(1,3-dimethylpyrazol-5-yl-carbonylamino)-(2-thienyl)actoamidoxime (4) α-(1-ethyl-3-methylpyrazole-5-yl-carbonylamino)(2-thienyl)actoamidoxime (5) α-(1-cyclopropylmethyl-3-methylpyrazole-5-yl-carbonylamino)(2-thienyl)actoamidoxime (6) α-(1-cyclobutyl-3-methylpyrazole-5-ylcarbonylamino)(2-furyl)acetoamidoxime (7) α-(1-ethyl-3-methylpyrazole-5-yl-carbonylamino)(2-furyl)actoamidoxime (8) α-(1-cyclobutyl-3-methylpyrazole-5-yl-carbonylamino)(3-thienyl)actoamidoxime (9) α-(1-isopropyl-3-methylpyrazole-5-yl-carbonylamino)(2-thienyl)actoamidoxime

(10) α-(1-isopropyl-3-methylpyrazole-5-yl-carbonylamino)(3-thienyl)actoamidoxime

(11) α-(1-cyclopropyl-3-methylpyrazole-5-yl-carbonylamino)(2-thienyl)acetoamidoxime

(12) α-(1-cyclopropyl-3-methylpyrazole-5-yl-carbonylamino)(3-thienyl)actoamidoxime

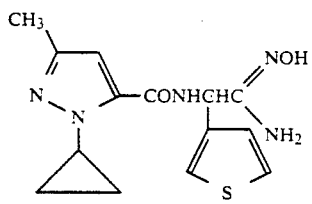

(13) α-(1-cyclopropyl-b 3-methylpyrazole-5-yl-carbonylamino)(2-furyl)actoamidoxime

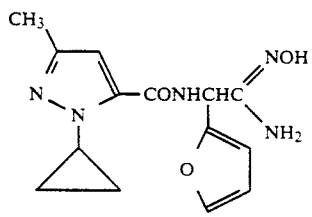

(14) α-(1-cyclopropyl-3-methylpyrazole-5-yl-carbonylamino)(3-furyl)actoamidoxime

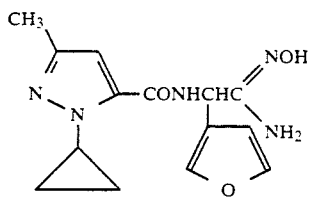

and optically active isomers thereof.

3. A fungicide for agricultural and horticultural use which comprises as an effective ingredient an oxime derivative represented by the general formula (I):

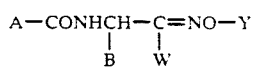

wherein:
A represents an optionally substituted pyrazolyl group.
B represents an optionally substituted furyl group, an unsubstituted or substituted thienyl group, an unsubstituted or substituted phenyl group, an unsubstituted or substituted pyrazolyl group, an alkenyl group having 2 to 10 carbon atoms, a halogenated alkenyl group having 2 to 10 carbon atoms, an alkoxy group having 1 to 10 carbon atoms, an alkenyloxy group having 2 to 10 carbon atoms, an alkynyloxy group having 2 to 10 carbon atoms or an alkylthio group having 1 to 10 carbon atoms,
Y represents a hydrogen atom, and
W represents a hydrogen atom, a halogen atom, an unsubstituted or substituted phenylamino group, an amino group or an alkylamino group, or an optically active isomer thereof.

4. A fungicide as claimed in claim 3, wherein said oxime derivative is selected from among the following ones:

(1) α-(1-cyclobutyl-3-methylpyrazole-5-yl-carbonylamino) (2-thienyl)acetoamidoxime

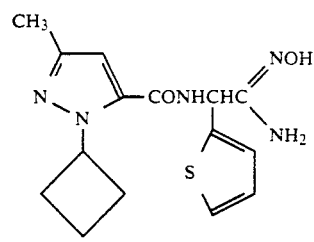

(2) α-(1-cyclobutyl-3-methylpyrazole-5-yl-carbonylamino) (3-furyl)acetoamidoxime

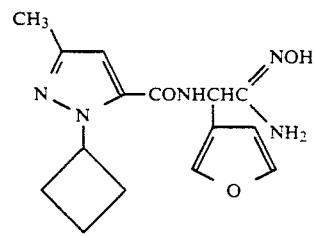

(3) α-(1,3-dimethylpyrazol-5-yl-carbonylamino)-(2-thienyl)actoamidoxime

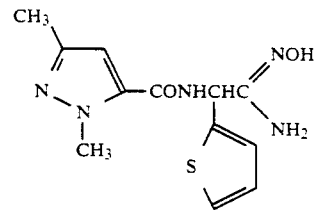

(4) α-(1-ethyl-3-methylpyrazole-5-yl-carbonylamino) (2-thienyl)actoamidoxime

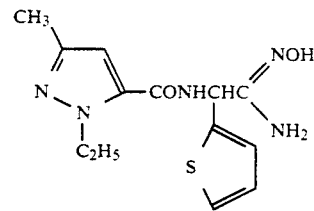

(5) α(1-cyclopropylmethyl-3-methylpyrazole-5-yl-carbonylamino) (2-thienyl)actoamidoxime

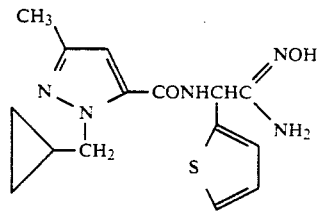

(6) α(1-cyclobutyl-3-methylpyrazole-5-yl-carbonylamino) (2-furyl)acetoamidoxime (7) α-(1-ethyl-3-methylpyrazole-5-yl-carbonylamino) (2-furyl)actoamidoxime)

(8) α-(1-cyclobutyl-3-methylpyrazole-5-yl-carbonylamino) (2-thienyl)actoamidoxime (9) α-(1-isopropyl-3-methylpyrazole-5-yl-carbonylamino) (2-thienyl)actoamidoxime

(10) α-(1-isopropyl-3-methylpyrazole-5-yl-carbonylamino) (3-thienyl)actoamidoxime

(11) α-(1-cyclopropyl-3-methylpyrazole-5-yl-carbonylamino) (2-thienyl)acetoamidoxime

(12) α-(1-cyclopropyl-3-methylpyrazole-5-yl-carbonylamino) (3-thienyl)actoamidoxime

(13) α-(1-cyclopropyl-3-methylpyrazole-5-yl-carbonylamino) (2-furyl)actoamidoxime

(14) α-(1-cyclopropyl-3-methylpyrazole-5-yl-carbonylamino) (3-furyl)actoamidoxime and optically active isomers thereof.

* * * * *